United States Patent
Anand et al.

(10) Patent No.: US 10,792,480 B2
(45) Date of Patent: Oct. 6, 2020

(54) SHUNT FLUSHERS AND RELATED METHODS

(71) Applicant: Anuncia, Inc., Lowell, MA (US)

(72) Inventors: P J Anand, Lowell, MA (US); Deep Arjun Singh, Cambridge, MA (US); Greg Eberl, Acton, MA (US); Andrew East, Arlington, MA (US); Morgan Brophy, Somerville, MA (US); Ayesha Arzumand, North Billerica, MA (US); Stela Moura, Lowell, MA (US); Loredana Guseila, Lowell, MA (US)

(73) Assignee: Anuncia, Inc., Lowell, MA (US)

( * ) Notice: Subject to any disclaimer, the term of this patent is extended or adjusted under 35 U.S.C. 154(b) by 214 days.

(21) Appl. No.: 15/782,247

(22) Filed: Oct. 12, 2017

(65) Prior Publication Data

US 2018/0104459 A1     Apr. 19, 2018

Related U.S. Application Data

(60) Provisional application No. 62/500,547, filed on May 3, 2017, provisional application No. 62/407,810, filed on Oct. 13, 2016.

(51) Int. Cl.
*A61M 27/00* (2006.01)
*A61M 39/22* (2006.01)
(Continued)

(52) U.S. Cl.
CPC ........ *A61M 27/006* (2013.01); *A61M 39/223* (2013.01); *A61M 5/14276* (2013.01);
(Continued)

(58) Field of Classification Search
CPC .............. A61M 27/006; A61M 27/002; A61M 27/008; A61M 39/223; A61M 5/14276;
(Continued)

(56) References Cited

U.S. PATENT DOCUMENTS

| 3,111,125 A | 11/1963 | Schulte |
| 3,452,757 A | 7/1969 | Ames |

(Continued)

FOREIGN PATENT DOCUMENTS

| CN | 202191577 U | 4/2012 |
| JP | S60-68840 A | 4/1985 |

(Continued)

OTHER PUBLICATIONS

International Search Report and Written Opinion for Application No. PCT/US2017/056313 (23 pages).

(Continued)

*Primary Examiner* — Philip R Wiest
(74) *Attorney, Agent, or Firm* — Nutter McClennen & Fish LLP

(57) ABSTRACT

Systems and methods for flushing shunt systems are disclosed herein. In some embodiments, a flusher includes a pinch tube that extends over a flush dome such that a user can simultaneously close the pinch tube and actuate the flush dome with a single motion. Flushing and refill valves of the system can be disposed in a cartridge that is laterally-offset from the flush dome, advantageously reducing the height profile of the flusher. Flushers with integrated shunt valves are also disclosed, as are shunt systems with restricted and unrestricted modes for selectively limiting the instances in which a user can open an auxiliary flow path through the system.

15 Claims, 30 Drawing Sheets

(51) Int. Cl.
*A61M 25/00* (2006.01)
*A61M 5/142* (2006.01)

(52) U.S. Cl.
CPC .............. *A61M 2025/0019* (2013.01); *A61M 2202/0464* (2013.01); *A61M 2210/0693* (2013.01)

(58) Field of Classification Search
CPC .. A61M 2025/0019; A61M 2202/0464; A61M 2210/0693
See application file for complete search history.

(56) References Cited

U.S. PATENT DOCUMENTS

| | | | |
|---|---|---|---|
| 3,492,996 | A | 2/1970 | Fountain |
| 3,595,240 | A | 7/1971 | Mishler |
| 3,827,439 | A | 8/1974 | Schulte et al. |
| 3,886,948 | A | 6/1975 | Hakim |
| 4,464,168 | A | 8/1984 | Redmond et al. |
| 4,474,569 | A | 10/1984 | Newkirk |
| 4,560,375 | A | 12/1985 | Schulte et al. |
| 4,605,395 | A | 8/1986 | Rose et al. |
| 4,698,058 | A | 10/1987 | Greenfeld et al. |
| 4,741,730 | A | 5/1988 | Dormandy |
| 4,850,955 | A | 7/1989 | Newkirk |
| 4,861,331 | A | 8/1989 | East et al. |
| 4,867,740 | A | 9/1989 | East |
| 4,867,741 | A | 9/1989 | Portnoy |
| 5,106,368 | A | 4/1992 | Uldall et al. |
| 5,154,693 | A | 10/1992 | East et al. |
| 5,167,615 | A | 12/1992 | East et al. |
| 5,304,114 | A | 4/1994 | Cosman |
| 5,387,188 | A | 2/1995 | Watson |
| 5,637,083 | A | 6/1997 | Bertrand et al. |
| 5,843,013 | A | 12/1998 | Lecuyer et al. |
| 6,193,682 | B1 | 2/2001 | Ahmed |
| 6,383,159 | B1 | 5/2002 | Saul |
| 6,453,185 | B1 | 9/2002 | O'Keefe |
| 6,875,192 | B1 | 4/2005 | Saul et al. |
| 6,913,589 | B2 | 7/2005 | Dextradeur et al. |
| 6,916,313 | B2 | 7/2005 | Cunningham |
| 7,189,221 | B2 | 3/2007 | Silverberg et al. |
| 7,235,060 | B2 | 6/2007 | Kraus |
| 7,699,800 | B2 | 4/2010 | Dextradeur et al. |
| 7,842,002 | B2 | 11/2010 | Mantle |
| 9,433,764 | B2 | 9/2016 | East et al. |
| 9,629,987 | B2 | 4/2017 | Anand et al. |
| 9,744,338 | B2 | 8/2017 | East et al. |
| 10,493,249 | B2 | 12/2019 | East et al. |
| 10,639,461 | B2 | 5/2020 | Anand et al. |
| 2002/0128588 | A1 | 9/2002 | Borgesen |
| 2004/0068201 | A1 | 4/2004 | Saul |
| 2004/0147871 | A1 | 7/2004 | Burnett |
| 2004/0260249 | A1 | 12/2004 | Kulessa |
| 2005/0277862 | A1 | 12/2005 | Anand |
| 2006/0020239 | A1 | 1/2006 | Geiger et al. |
| 2006/0074388 | A1 | 4/2006 | Dextradeur et al. |
| 2006/0167539 | A1 | 7/2006 | McEwan |
| 2008/0243074 | A1 | 10/2008 | Miesel et al. |
| 2010/0121250 | A1 | 5/2010 | Pizzi |
| 2011/0257593 | A1 | 10/2011 | Kalpin et al. |
| 2012/0078159 | A1 | 3/2012 | Wilson et al. |
| 2012/0095485 | A1 | 4/2012 | Cully et al. |
| 2012/0232461 | A1 | 9/2012 | Seaver et al. |
| 2012/0232462 | A1 | 9/2012 | Miethke |
| 2012/0302938 | A1 | 11/2012 | Browd et al. |
| 2013/0303971 | A1 | 11/2013 | Budgett et al. |
| 2014/0094735 | A1 | 4/2014 | Wilson et al. |
| 2014/0207043 | A1 | 7/2014 | Anand et al. |
| 2014/0207045 | A1 | 7/2014 | Anand et al. |
| 2014/0228734 | A1 | 8/2014 | Wilson et al. |
| 2014/0276341 | A1 | 9/2014 | Ludin et al. |
| 2015/0297874 | A1 | 10/2015 | East et al. |
| 2015/0367110 | A1* | 12/2015 | East ................... A61M 27/006 604/9 |
| 2016/0038724 | A1 | 2/2016 | Madsen et al. |
| 2016/0287111 | A1 | 10/2016 | Jacobsen |
| 2017/0189656 | A1 | 7/2017 | Anand et al. |
| 2018/0064919 | A1 | 3/2018 | East et al. |

FOREIGN PATENT DOCUMENTS

| | | |
|---|---|---|
| JP | 2003-507140 A | 2/2003 |
| JP | 2003-235987 A | 8/2003 |
| JP | 2012-071135 A | 4/2012 |
| WO | 83/001387 A1 | 4/1983 |
| WO | 91/17779 A1 | 11/1991 |
| WO | 01/13984 A2 | 3/2001 |
| WO | 2007/092875 A2 | 8/2007 |
| WO | 2008/027322 A1 | 3/2008 |
| WO | 2011/104712 A1 | 9/2011 |
| WO | 2011/146757 A2 | 11/2011 |
| WO | 2012/055048 A1 | 5/2012 |
| WO | 2014/116640 A1 | 7/2014 |
| WO | 2014/149648 A1 | 9/2014 |

OTHER PUBLICATIONS

U.S. Appl. No. 14/160,695, filed Jan. 22, 2014, Systems and Methods for Shunting Fluid.
U.S. Appl. No. 14/160,768, filed Jan. 22, 2014, Systems and Methods for Shunting Fluid.
U.S. Appl. No. 14/690,389, filed Apr. 18, 2015, Systems and Methods for Shunting Fluid.
U.S. Appl. No. 14/740,478, filed Jun. 16, 2015, Systems and Methods for Shunting Fluid.
U.S. Appl. No. 15/462,599, filed Mar. 17, 2017, Systems for Methods for Shunting Fluid.
U.S. Appl. No. 15/654,749, filed Jul. 20, 2017, Systems and Methods for Shunting Fluid.
Extended European Search Report for Application No. 18199510.1, dated Feb. 11, 2019 (12 pages).
International Preliminary Report on Patentability for Application No. PCT/US2017/05613; dated Apr. 25, 2019 (14 pages).
Japanese Office Action for Application No. 2016-563078, dated Feb. 5, 2019 (8 pages).
[No Author Listed] Integra Neurosciences™, "Integra™ Flow Regulating Valve, Mini," 2010 (12 pages).
[No Author Listed] Integra Neurosciences™ "Ventricular Drainage System," 2002 (20 pages).
Extended European Search Report for Application No. 14743442.7, dated Jun. 1, 2016 (10 pages).
Extended European Search Report for Application No. 14770962.0, dated Aug. 18, 2016 (7 pages).
Extended European Search Report for Application No. 15779584.0, dated Oct. 10, 2017 (7 Pages).
Garton et al., "Hydrocephalus," Ped. Clin. N. Am., 51, pp. 305-325, 2004 (21 pages).
International Invitation to Pay Additional Fees for Application No. PCT/US2014/12449 dated Mar. 27, 2014 (2 Pages).
International Search Report and Written Opinion for PCT/US2014/012449, dated May 27, 2014 (24 pages).
International Search Report and Written Opinion for Application No. PCT/US2014/020082, dated Jun. 6, 2014 (9 pages).
International Preliminary Report on Patentability for Application No. PCT/US2014/020082, dated Sep. 24, 2015 (9 Pages).
International Search Report and Written Opinion for PCT/US2015/026555, dated Jul. 13, 2015 (11 pages).
Japanese Office Action for Application No. 2015-555226, dated Dec. 19, 2017 (7 pages).
U.S. Appl. No. 16/690,875, filed Nov. 21, 2019, Systems and Methods for Shunting Fluid.
U.S. Appl. No. 16/865,779, filed May 4, 2020, Systems and Methods for Shunting Fluid.
Japanese Office Action for Application No. 2019-045655, dated Feb. 25, 2020 (6 pages).

* cited by examiner

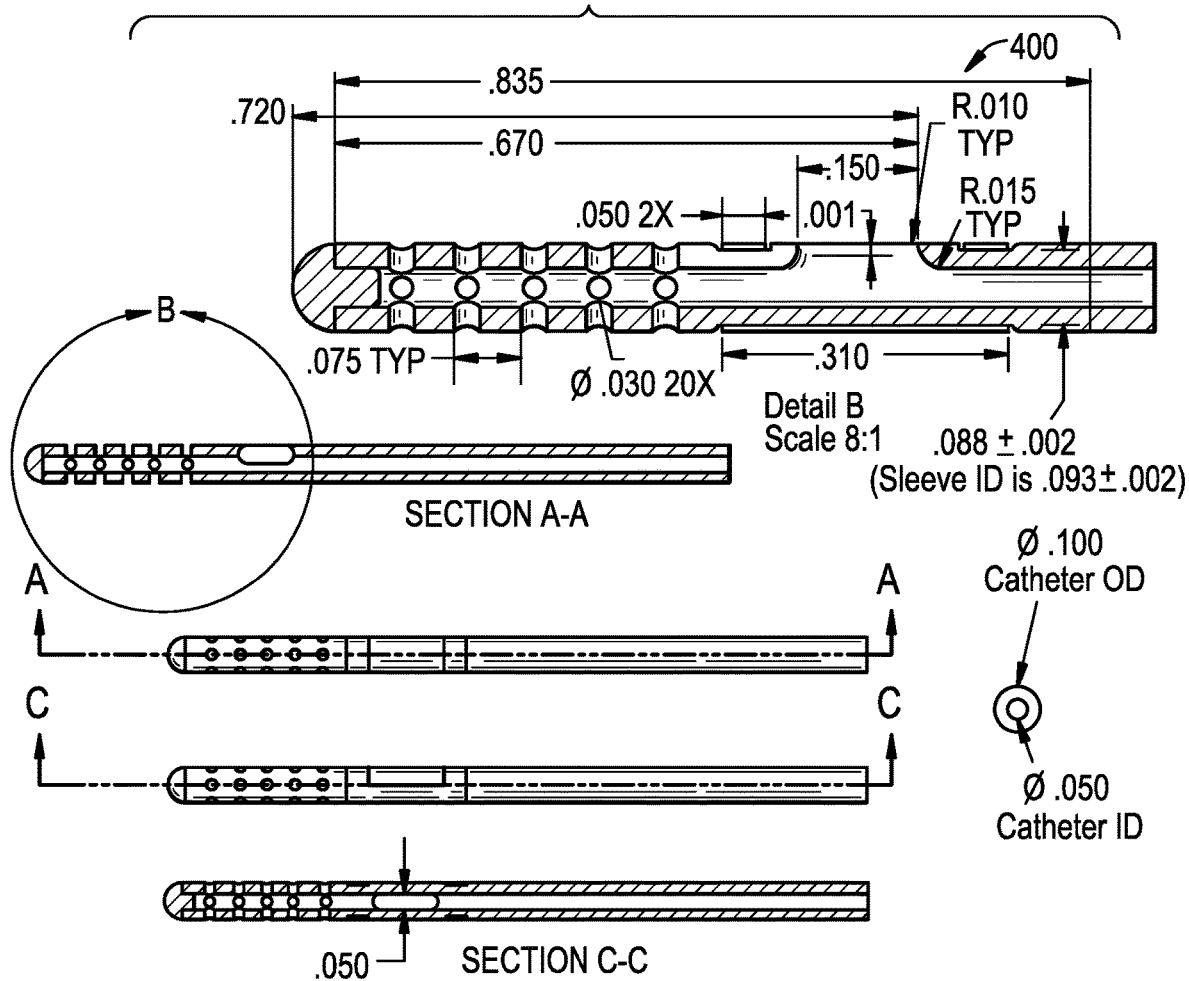
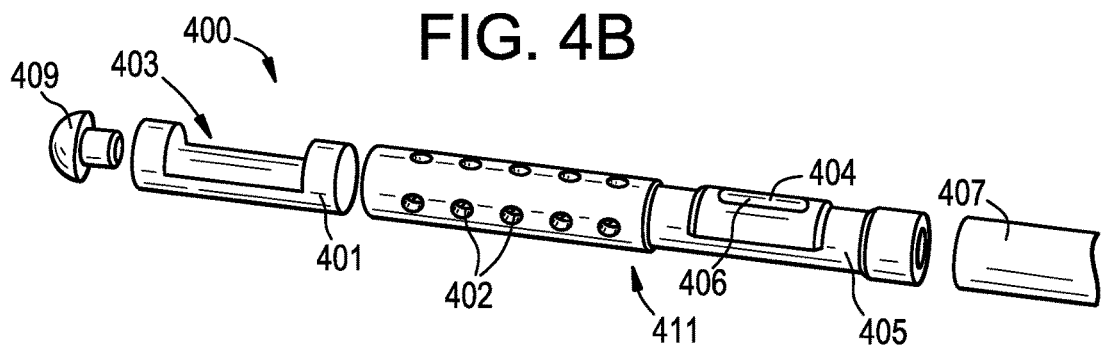

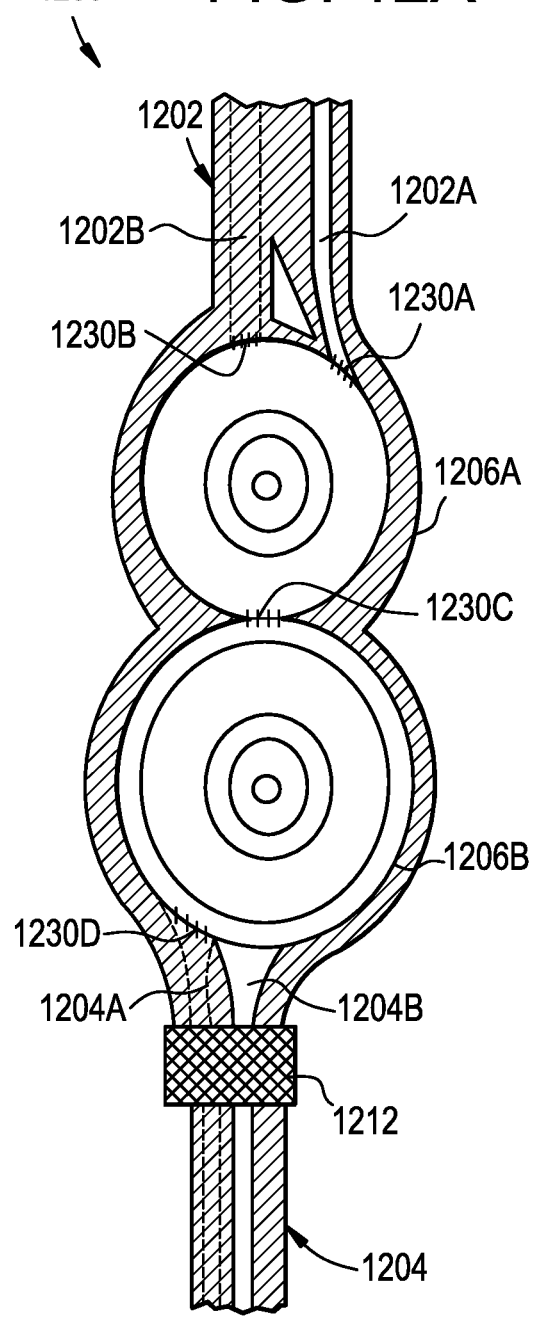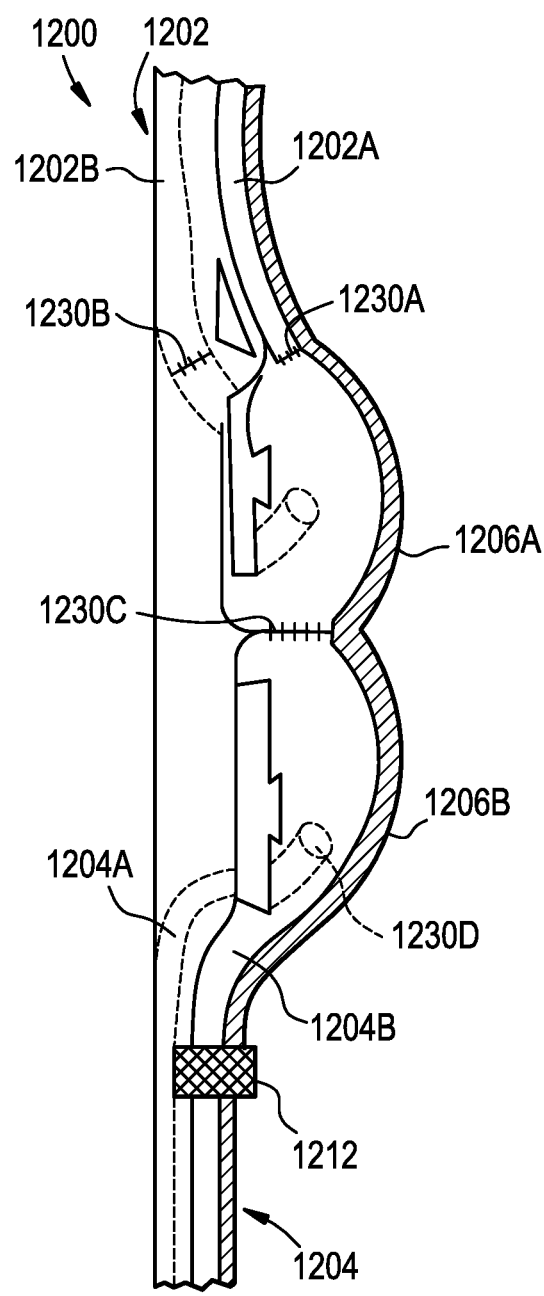

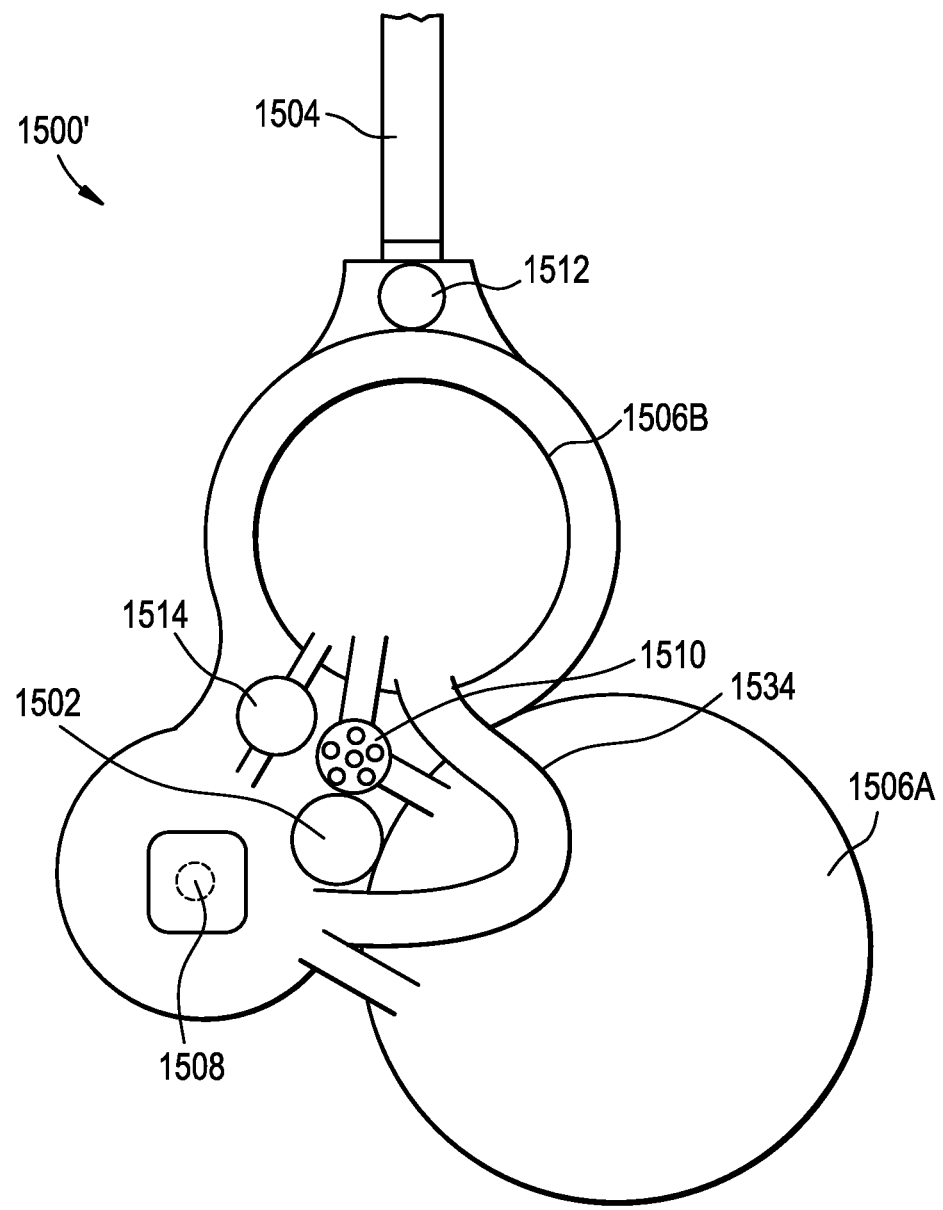

FIG. 17A
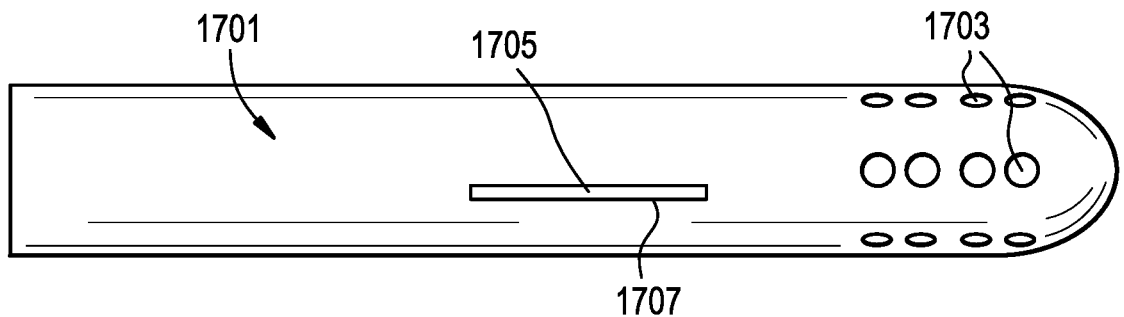
FIG. 17B
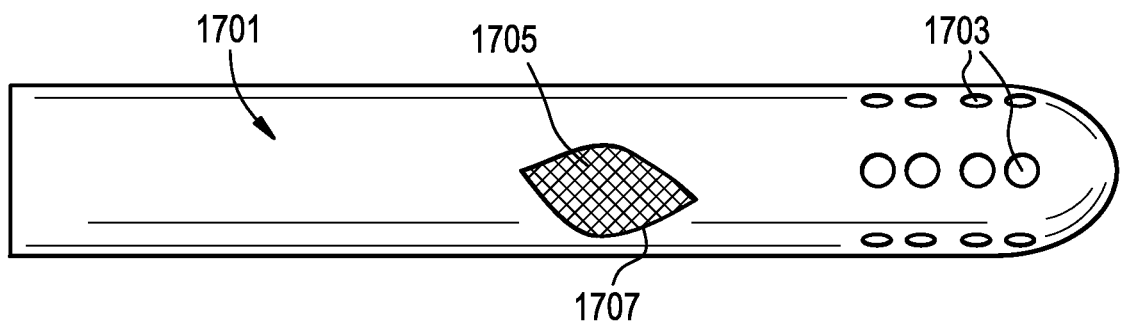
FIG. 18A
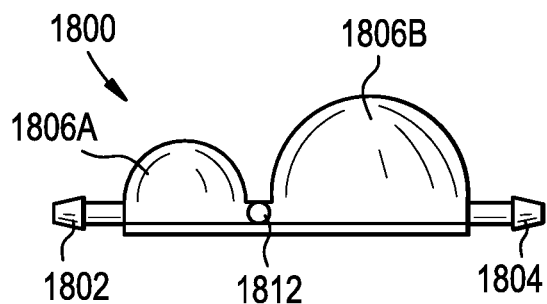
FIG. 18B
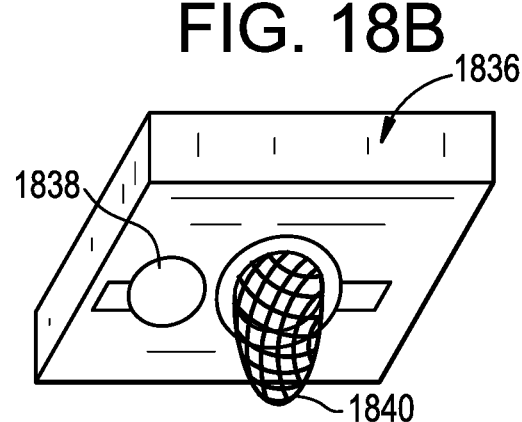
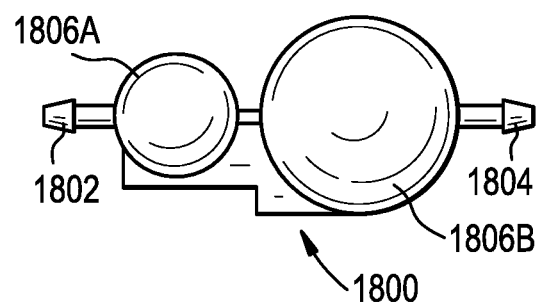

FIG. 23
FIG. 24
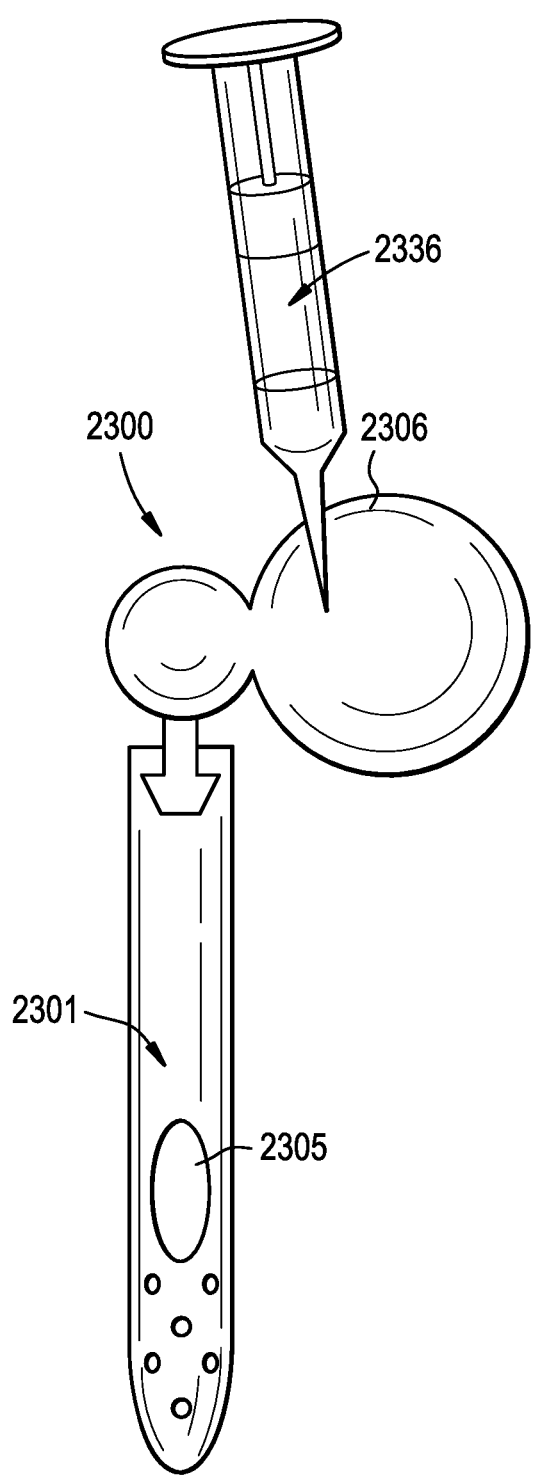
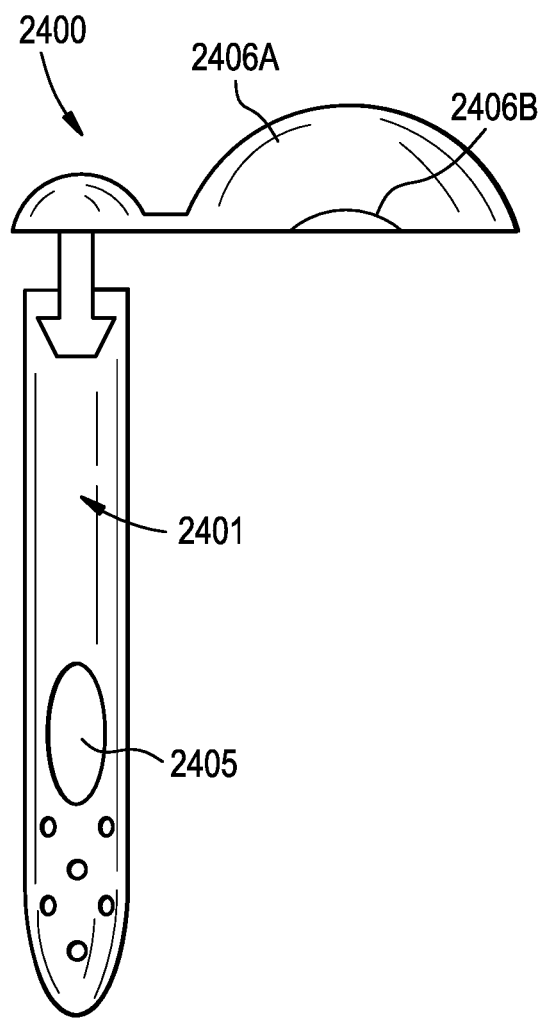

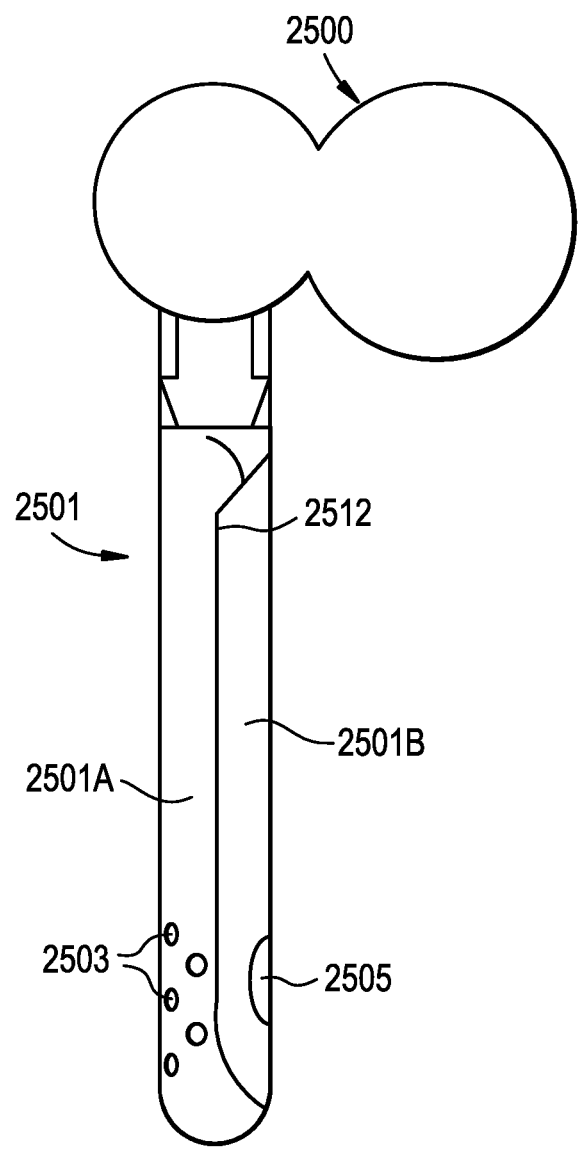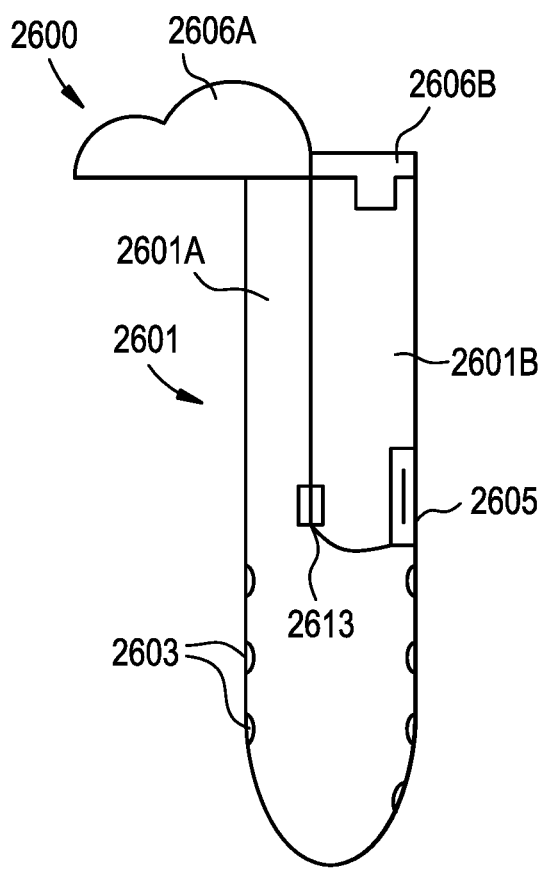

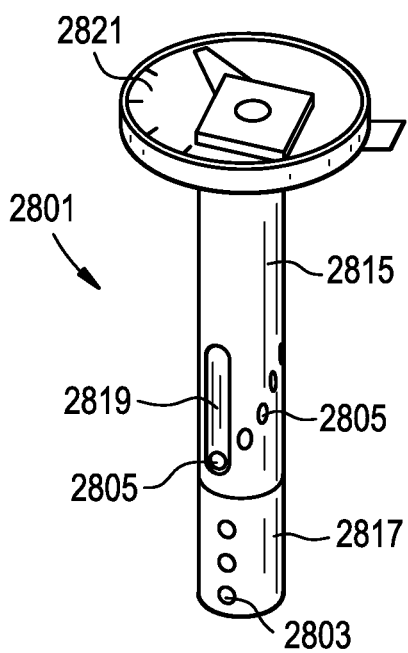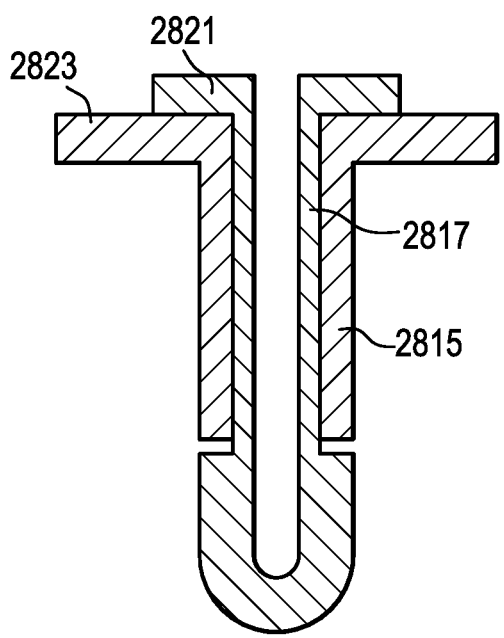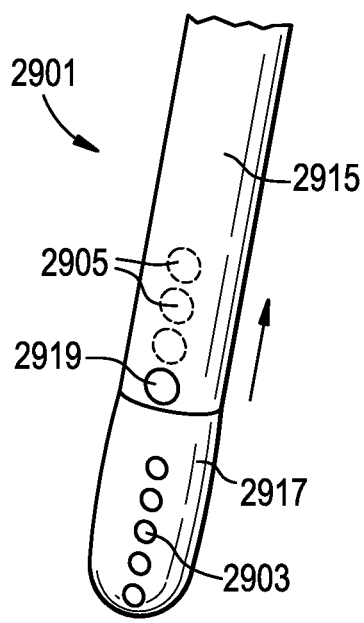

SHUNT FLUSHERS AND RELATED METHODS

CROSS-REFERENCE TO RELATED APPLICATIONS

This application claims priority to U.S. Provisional Application No. 62/407,810 filed on Oct. 13, 2016 and U.S. Provisional Application No. 62/500,547 filed on May 3, 2017, each of which is hereby incorporated by reference herein.

FIELD

Shunt flushers and related methods are disclosed herein, e.g., for use in shunting cerebrospinal fluid in the treatment of hydrocephalus.

BACKGROUND

Shunt systems for transport of body fluids from one region of the body to another region are generally known. For example, shunt systems are often used in the treatment of hydrocephalus to drain excess cerebrospinal fluid (CSF) from the ventricles of the brain. A typical shunt system includes a one-directional, pressure-controlled valve that is implanted beneath the skin. A ventricular catheter extends from one side of the valve to the ventricle. A drain catheter extends from the other side of the valve to a drain site, such as the abdominal cavity.

After implantation and use over extended time periods, shunt systems tend to become clogged in certain individuals. Clogging can occur due to foreign materials which collect in the narrow tubular passageways of the shunt system and in the inlet and outlet openings of such passageways. Consequently, it is often necessary to perform follow-on operations on an individual to remove the clog or replace the entire system. The inconvenience, cost, and risk of complications associated with these follow-on procedures are considerable and undesirable. Accordingly, a need exists for improved systems and methods for shunting fluid.

SUMMARY

Systems and methods for flushing shunt systems are disclosed herein. In some embodiments, a flusher includes a pinch tube that extends over a flush dome such that a user can simultaneously close the pinch tube and actuate the flush dome with a single motion. Flushing and refill valves of the system can be disposed in a cartridge that is laterally-offset from the flush dome, advantageously reducing the height profile of the flusher. Flushers with integrated shunt valves are also disclosed, as are shunt systems with restricted and unrestricted modes for selectively limiting the instances in which a user can open an auxiliary flow path through the system.

In some embodiments, a shunt system can include a catheter having a primary flow port and an auxiliary flow port; and a flusher configured to emit a flushing cough or pulse of fluid through the catheter; wherein the shunt system is operable in a restricted mode in which: (i) a flush generated by the flusher is insufficient to open the auxiliary flow port; or (ii) the flusher is prevented from emitting the flush; wherein the shunt system is operable in an unrestricted mode in which: (i) a flush generated by the flusher is sufficient to open the auxiliary flow port; or (ii) the flusher is not prevented from emitting the flush; and wherein the flusher includes a control operable to switch the flusher between the restricted mode and the unrestricted mode.

The control can be configured such that it locks a flush valve of the flusher in a closed position to operate in the restricted mode and does not lock the flush valve in the closed position to operate in the unrestricted mode. The control can be configured such that it decreases an opening pressure threshold of a flush valve of the flusher to operate in the restricted mode and increases the opening pressure threshold of the flush valve to operate in the unrestricted mode. The control can be configured such that it reduces the pressure of the flush in the restricted mode and increases the pressure of the flush in the unrestricted mode. The control can reduce the pressure of the flush by placing a flush dome of the flusher in communication with a first flush valve having a lower opening pressure. The control can increase the pressure of the flush by placing the flush dome in communication with a second flush valve having a higher opening pressure. The control can reduce the volume of the flush in the restricted mode and increase the volume of the flush in the unrestricted mode. The control can reduce the volume of the flush by limiting refill of a flush dome of the flusher. The control can reduce the volume of the flush by decreasing the effective volume of a flush dome of the flusher. The control can decrease the effective volume by at least one of: moving a divider within the flush dome, moving a volume-occupying object into the flush dome, and expanding a compartment within the flush dome. The control can be configured such that it isolates the auxiliary flow port from the flush in the restricted mode and does not isolate the auxiliary flow port from the flush in the unrestricted mode. The catheter can include a first fluid lumen in communication with the primary flow port and a second fluid lumen in communication with the auxiliary flow port. The control can select which of the first and second fluid lumens of the catheter is in fluid communication with a flush dome of the flusher. The control can be operable to selectively direct the flush to one or more of an upstream port of the flusher and a downstream port of the flusher.

In some embodiments, a shunt system can include a catheter having a primary flow port and an auxiliary flow port; and a flusher configured to selectively emit a first flush of fluid through the catheter or a second flush of fluid through the catheter; wherein the first flush of fluid is not sufficient to open the auxiliary flow port and wherein the second flush of fluid is sufficient to open the auxiliary flow port.

The second flush can have a higher pressure than the first flush. The second flush can have a higher volume than the first flush. The flusher can include first and second flush domes. The first and second flush domes can be actuated simultaneously. The flusher can emit the first flush by allowing fluid to escape from the first flush dome without contributing to the flush. The flusher can emit the second flush by including fluid in the first flush dome in the flush. The flusher can emit the first flush when the first flush dome is collapsed and can emit the second flush when the second flush dome is collapsed. The system can include a control that isolates the second flush dome from an upstream port of the flusher to restrict opening of the auxiliary flow port. The second flush dome can have a greater volume than the first flush dome.

In some embodiments, a shunt system can include a catheter having a primary flow port and an auxiliary flow port; a flusher configured to selectively emit a flush of fluid through the catheter; and a compliance feature in communication with a flush path through the catheter; wherein the shunt system is operable in a first mode in which the compliance feature expands during a flushing operation to a degree sufficient to prevent a flush emitted from the flusher from opening the auxiliary flow port; and wherein the shunt system is operable in a second mode in which the compliance feature does not expand during a flushing operation to a degree sufficient to prevent a flush emitted from the flusher from opening the auxiliary flow port.

The flusher can include a control configured to selectively place the compliance feature in communication with the flush path. The shunt system can operate in the second mode by physically impeding expansion of the compliance feature. The shunt system can include an extracorporeal member positionable over the compliance feature when the compliance feature is implanted in a patient to block expansion of the compliance feature.

In some embodiments, a ventricular shunt catheter can include a primary flow port through which fluid can flow between an exterior of the catheter and an interior of the catheter; and an auxiliary flow port through which fluid can flow between an exterior of the catheter and an interior of the catheter; wherein the auxiliary flow port is initially closed to block fluid flow therethrough and wherein the auxiliary flow port is selectively openable to allow fluid to flow therethrough; wherein the auxiliary flow port is configured to open in response to a non-invasive extracorporeal input.

The catheter can include a clip that holds a shape memory frame of the auxiliary flow port closed, and wherein the input comprises actuating the clip. The clip can be actuated by applying an electric current to the clip to break the clip or by applying a magnetic field to the clip to move the clip.

In some embodiments, a shunt system can include a catheter having: a primary flow port through which fluid can flow between an exterior of the catheter and an interior of the catheter; and an auxiliary flow port through which fluid can flow between an exterior of the catheter and an interior of the catheter; wherein the auxiliary flow port is initially closed to block fluid flow therethrough and wherein the auxiliary flow port is selectively openable to allow fluid to flow therethrough; a flusher configured to emit a flush of fluid through a flush path of the catheter; wherein the catheter has a first configuration in which the flush of fluid is not effective to open the auxiliary flow port and a second configuration in which the flush of fluid is effective to open the auxiliary flow port; wherein the catheter changes from the first configuration to the second configuration in response to an input.

The input can be a non-invasive extracorporeal input. The catheter can include a valve that isolates the auxiliary flow port from the flush path and the input can include opening the valve. The valve can be opened by directing a flush of fluid through the catheter sufficient to open the valve. The input can be effective to rupture a partition formed within the catheter between the auxiliary flow port and the flush path. The input can be effective to change an aperture size of a partition formed within the catheter between the auxiliary flow port and the flush path. The input can inflate a balloon of the catheter to open a flow path between the flush path and the auxiliary fluid port. The input can deflate a balloon of the catheter to open a flow path between the flush path and the auxiliary flow port. The input can rotate a sheath coaxially disposed with the catheter relative to the catheter to uncover an auxiliary flow port. Rotating the sheath by a first degree can align an opening of the sheath with the auxiliary flow port and rotating the sheath by a second degree can align the opening of the sheath with a second auxiliary flow port. The input can translate a sheath coaxially disposed with the catheter longitudinally with respect to the catheter to uncover an auxiliary flow port. The catheter can include a sensor configured to detect when the auxiliary flow port is opened. The catheter can include a wire that reinforces the auxiliary flow port. The input can include severing the wire or retracting the wire proximally relative to the catheter.

In some embodiments, a flusher can include a body that defines a collapsible flush dome; a valve cartridge that houses a refill valve and a flush valve, the valve cartridge being laterally-offset from the flush dome; a passive flow path that extends between an upstream port and a downstream port, at least a portion of the flow path being defined by a collapsible fluid pathway that extends across an exterior surface of the flush dome; wherein the flush valve has a first position in which the flush dome is not in fluid communication with the upstream port or the passive flow path and a second position in which the flush dome is in fluid communication with the upstream port and the passive flow path; wherein application of a force to the collapsible fluid pathway is effective to collapse the collapsible fluid pathway to block the passive flow path and to collapse the dome to move the flush valve to the second position and flush fluid through the upstream port.

The flush valve can include a valve body that is compressed against a valve seat by an adjustment disc such that rotation of the adjustment disc is effective to change a threshold opening pressure of the valve. The adjustment disc can be threadably mounted in the valve cartridge. The adjustment disc can be actuated from a position outside of a patient in which the flusher is implanted. The flush valve can have a predetermined fixed height or positive stop such that the flush valve is compressed to a desired amount of compression to yield a desired opening pressure. The refill valve can have a first position in which the passive flow path is not in fluid communication with the flush dome and a second position in which the passive flow path is in fluid communication with the flush dome. Collapsing the flush dome can be effective to hold the refill valve in the first position. The flusher can include a ventricular catheter in fluid communication with the upstream port. The collapsible fluid pathway can include a pinch tube attached to a trough formed in the exterior surface of the flush dome, the pinch tube and the trough collectively defining an inner lumen of a portion of the passive flow path. The cartridge can include an upper chamber and a lower chamber separated by a dividing wall. The flush valve and the refill valve can each control fluid communication between the upper and lower chambers. The upper chamber can be in fluid communication with the flush dome via a first barbed fitting, the lower chamber can be in fluid communication with the collapsible fluid pathway via a second barbed fitting, and the lower chamber can be in fluid communication with a ventricular catheter via a third barbed fitting. The cartridge can be attached to the body by a first barbed fitting in fluid communication with the flush dome and a second barbed fitting in fluid communication with the collapsible fluid pathway. In some embodiments, fluid can flow in the upstream port, through the collapsible fluid pathway, and out of the downstream port without flowing across any portion of the refill valve, the flush valve, or the flush dome. The flusher can include a shunt valve disposed within the cartridge or the downstream port.

In some embodiments, a shunt system can include a catheter having a primary flow port and an auxiliary flow port; a flusher configured to emit a flushing cough or pulse of fluid through the catheter; wherein the shunt system is operable in a restricted mode in which a flush generated by the flusher is insufficient to open the auxiliary flow port and an unrestricted mode in which a flush generated by the flusher is sufficient to open the auxiliary flow port.

The flusher can include a control operable to switch the flusher between the restricted mode and the unrestricted mode. The control can be actuated non-invasively. The control can be actuated from a position outside of a patient in which the shunt system is implanted. The control can be magnetically-actuated or hydraulically-actuated. The control can include a valve.

The control can adjust a cracking pressure of a flush valve of the flusher. The control can adjust an effective volume of a flush cavity of the flusher. The control can adjust the effective volume by selectively inflating or deflating an inflatable member disposed within the flush cavity. The control can adjust the effective volume by moving at least a portion of a sidewall of the flush cavity. The control can adjust the effective volume by selectively advancing or retracting a movable member into or out of the flush cavity. The catheter can include a plurality of auxiliary flow ports, each having a progressively higher burst requirement. The catheter can include a plurality of auxiliary flow ports, each covered by membranes having progressively higher thicknesses. The control can include a compliant feature movable between a collapsed state and an expanded state. The compliant feature can include a passive flow path therethrough. The compliant feature can be in fluid communication with a flush emitted by the flusher, and the compliant feature can move to the expanded state to absorb at least a portion of the flush when in the restricted mode. The control can include at least one valve that isolates the compliant feature from the flush emitted by the flusher when in the unrestricted mode and that places the compliant feature in fluid communication with the flush when in the restricted mode. The control can be actuated to progressively access a sequence of auxiliary flow ports through the catheter. The control can be actuated to access the next in a series of auxiliary flow ports of the catheter.

In some embodiments, a flusher can include an outer housing; a passive flow path that extends between an upstream port and a downstream port; a flush dome configured to be pressed to expel fluid therefrom to flush fluid through at least one of the upstream port and the downstream port; a flush valve configured to control the pressure at which fluid is expelled from the flush dome; and a shunt valve configured to regulate flow through the passive flow path to control a patient's ventricle pressure; wherein the shunt valve and the flush valve are disposed within the housing of the flusher.

In some embodiments, a method can include actuating a control of a flusher implanted in a patient to progressively access a sequence of auxiliary flow ports through a ventricular catheter in fluid communication with the flusher.

BRIEF DESCRIPTION OF THE DRAWINGS

The invention will be more fully understood from the following detailed description taken in conjunction with the accompanying drawings, in which:

FIG. 4A is a sectional view of a catheter;
FIG. 4B is an exploded view of the catheter of FIG. 4A;
FIG. 12A is a schematic sectional top view of a flusher;
FIG. 12B is a schematic sectional side view of the flusher of FIG. 12A;
FIG. 15C is a schematic sectional top view of a flusher;
FIG. 17A is a side view of a catheter having a closed auxiliary flow port;
FIG. 17B is a side view of the catheter of FIG. 17A with an open auxiliary flow port;
FIG. 18A is a side view of a flusher;
FIG. 18B is a perspective view of the flusher of FIG. 18A with a flush device.

FIG. 23 is a schematic perspective view of a shunt system and a syringe;

FIG. 24 is a schematic sectional side view of a shunt system;

FIG. 25 is a schematic sectional top view of a shunt system;

FIG. 26 is a schematic sectional side view of a shunt system;

FIG. 28A is a perspective view of a catheter;

FIG. 28B is a sectional side view of the catheter of FIG. 28A and an adjustment mechanism;

FIG. 29 is a perspective view of a catheter;

DETAILED DESCRIPTION

Systems and methods for flushing shunt systems are disclosed herein. In some embodiments, a flusher includes a pinch tube that extends over a flush dome such that a user can simultaneously close the pinch tube and actuate the flush dome with a single motion. Flushing and refill valves of the system can be disposed in a cartridge that is laterally-offset from the flush dome, advantageously reducing the height profile of the flusher. Flushers with integrated shunt valves are also disclosed, as are shunt systems with restricted and unrestricted modes for selectively limiting the instances in which a user can open an auxiliary flow path through the system.

Certain exemplary embodiments will now be described to provide an overall understanding of the principles of the structure, function, manufacture, and use of the methods, systems, and devices disclosed herein. One or more examples of these embodiments are illustrated in the accompanying drawings. Those skilled in the art will understand that the methods, systems, and devices specifically described herein and illustrated in the accompanying drawings are non-limiting exemplary embodiments. The features illustrated or described in connection with one exemplary embodiment may be combined with the features of other embodiments.

Figure 1:
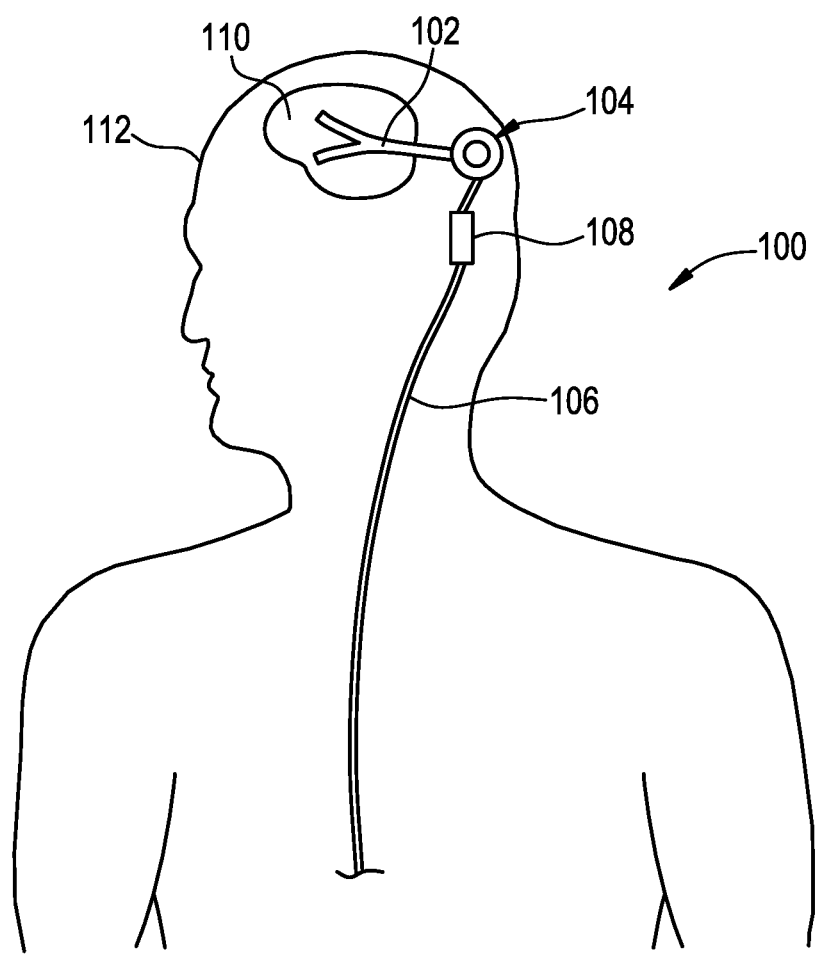
FIG. 1 is a schematic view of a shunt system implanted in a patient.

FIG. 1 illustrates an exemplary embodiment of a shunt system 100. The system generally includes a ventricular catheter 102, an anchor 104, and a drain catheter 106 with an inline valve 108. In some embodiments, the shunt system 100 can be used to treat hydrocephalus by implanting the ventricular catheter 102 such that a distal end of the catheter is disposed within a brain ventricle 110 of a patient 112. The anchor 104 can be mounted to the patient's skull, beneath the skin surface, and the drain catheter 106 can be implanted such that the proximal end of the drain catheter is disposed within a drain site, such as the abdominal cavity. In some embodiments, the anchor 104 can be or can include a Rickham-style reservoir. The valve 108 can be configured to regulate the flow of fluid from the ventricle 110 to the drain site. For example, when fluid pressure in the ventricle exceeds the opening pressure of the valve 108, the valve can be configured to open to allow excess fluid to drain out of the ventricle 110. When the fluid pressure drops to an acceptable level, the valve 108 can be configured to close, thereby stopping further draining of fluid.

It will be appreciated that the arrangement and features of the system 100 shown in FIG. 1 are merely exemplary, and that several other variations are possible. For example, the valve 108 can be disposed distal to the anchor 104 instead of proximal thereto as shown. In other embodiments, the valve 108 can be integral to the anchor 104 or the anchor can be omitted altogether.

The shunt system 100 can include any of a variety of catheters, including single lumen catheters, multi-lumen catheters, and split-tip catheters. Any of a variety of well-known valves 108 can be used, including those of the type described in U.S. Pat. No. 3,886,948, issued on Jun. 3, 1975 and entitled "VENTRICULAR SHUNT HAVING A VARIABLE PRESSURE VALVE," the entire contents of which are incorporated herein by reference.

In use, the shunt system 100 can be used to transfer fluid from one location to another location. When used in a patient's body, the shunt system 100 can be used to treat any of a variety of diseases, conditions, or ailments. Further details on shunt systems and related methods, including catheters and other features that can be used with the systems described herein, can be found in U.S. Pat. No. 9,433,764, issued on Sep. 6, 2016 and entitled "SYSTEMS AND METHODS FOR SHUNTING FLUID," the entire contents of which are incorporated herein by reference.

In some embodiments, the shunt system 100 can include a flusher for clearing obstructions from the shunt system or for opening auxiliary fluid paths through the shunt system (e.g., auxiliary fluid ports in the ventricular catheter). The flusher can be disposed between the ventricular catheter 102 and the anchor 104, between the anchor 104 and the valve 108, or between the valve 108 and the drain catheter 106. The flusher can also be formed integrally with any of the ventricular catheter 102, the anchor 104, the valve 108, and the drain catheter 106.

FIGS. 2A-2J illustrate an exemplary flusher 200 that can be used with a shunt system (e.g., with the shunt system 100 described above). The flusher 200 generally includes an outer shell or body 202 that defines a flush dome 204. The bottom surface of the body 202 is closed by a base plate 206 to which the body is sealed. A flush valve assembly 208 and a refill valve assembly 210 are disposed within a cartridge 214 coupled to the body 202, and a pinch tube 212 or other collapsible fluid pathway extends over the top of the flush dome 204. The cartridge is defined by upper and lower housings 214A, 214B sealed to one another that define an inner chamber 228 having an upper portion 228A and a lower portion 228B.

The valve cartridge 214 includes an upstream port 220 configured to be coupled to or placed in fluid communication with a ventricular catheter, a flush port 222 configured to be placed in fluid communication with the flush dome 204, and a passive flow port 224 configured to be placed in fluid communication with the pinch tube 212. The upstream port 220 and the passive flow port 224 are in fluid communication with the lower chamber 228B. The flush port 222 is in fluid communication with the upper chamber 228A. The ports 220, 222, 224 can be defined by barb-type fittings that extend radially outward from the valve cartridge 214. The barbed fittings can advantageously facilitate coupling of the cartridge 214 with the body 202 (in the case of the flush port 222), with the pinch tube 212 (in the case of the passive flow port 224), or with a ventricular catheter or other shunt system component (in the case of the upstream port 220). High interference barbed fittings can be used to allow high pressure operation without leakage, which allows the flushing pressure to be delivered only to the flush valve and facilitates more precise and repeatable opening pressure thresholds. In some embodiments, the barbed fittings can be configured to withstand up to 120 psi.

The flush valve assembly 208 includes a valve body 216 and an adjustment disc 218. The valve body 216 can be an umbrella-type valve, a Belleville-type valve, or the like. The valve body 216 is sandwiched between the adjustment disc 218 and a dividing wall 226 that separates the upper and lower chambers 228A, 228B and in an interference fit such that the valve body is compressed. The valve body 216 defines a substantially concave upper surface that forms a fluid-tight seal with the dividing wall 226 to seal off the flush port 222 from the upstream port 220 and the passive flow port 224 during normal operation. When sufficient pressure is applied to the upper surface of the valve body 216, the valve body deforms away from the dividing wall 226 to allow fluid communication between the flush port 222 and the upstream port 220 and between the flush port and the passive flow port 224.

The threshold pressure at which the valve body 216 opens can be infinitely adjusted by adjusting the pressure exerted on the valve body by the adjustment disc 218. In the illustrated embodiment, the adjustment disc 218 is threadably mounted in the cartridge 214 such that rotating the disc in a first direction increases the compression of the valve body 216 to increase the threshold pressure, and such that rotating the disc in a second, opposite direction decreases the compression of the valve body to decrease the threshold pressure. It will be appreciated that other means of adjusting the compression of the valve body 216 can be used instead or in addition. A driving interface 230 can be formed in the bottom surface of the adjustment disc 218 to facilitate rotation of the disc by a driving tool. In the illustrated embodiment, the driving interface 230 comprises first and second opposed cylindrical recesses configured to receive corresponding first and second pins of a driving tool. The arrangement of the recesses can allow rotation of the disc 218 to be easily visualized and to be performed in a repeatable and controlled manner. The adjustment disc 218 can be adjusted in-process and locked in a desired position using an adhesive (e.g., medical grade cyanoacrylate or the like). Locking the disc 218 in place, e.g., by freezing the threads using an adhesive, can advantageously allow for the threshold pressure of the valve to be securely maintained at the desired level.

When the valve body 216 is sealed against the dividing wall 226, fluid can flow from the upstream port 220, into the lower portion 228B of the chamber 228, and around the outside of the closed valve body. Fluid can also flow from the upstream port 220 into the passive flow port 224.

The refill valve assembly 210 includes a refill valve 236 and a refill plate 238. The refill plate 238 is defined by a portion of the dividing wall 226 of the cartridge 214. The lower part 228B of the cavity 228 extends beneath the refill plate 238 and is closed by a cover 240. The portion of the cavity 228B formed below the refill plate 238 is in fluid communication with the portion of the cavity 228B formed below the flush valve 216 via a recess 244 formed in the dividing wall 226. The refill valve 236 is operable to selectively place the lower cavity 228B in fluid communication with the upper cavity 228A and, by extension, with the interior of the flush dome 204, for example to refill the flush dome after a flushing operation is performed. In the illustrated embodiment, the refill valve 236 is an umbrella valve that includes a valve stem and a valve head. The stem is mounted within a valve guide formed in the refill plate 238. A plurality of openings 242 are formed in the plate 238 around the circumference of the valve guide. When the refill valve 236 is closed, the valve head covers the plurality of openings 242 and prevents fluid communication between the lower cavity 228B and the upper cavity 228A. When the refill valve 236 is opened, the valve head is lifted off of the openings 242 such that fluid can flow from the lower cavity 228B to the upper cavity 228A and into the flush dome 204.

As shown, the cartridge 214, including the refill valve 236 and the flush valve 216, is laterally offset from the flush dome 204, which can advantageously reduce the height profile of the device 200 as compared with designs in which one or both valves are vertically-aligned with the flush dome.

Figure 2A:
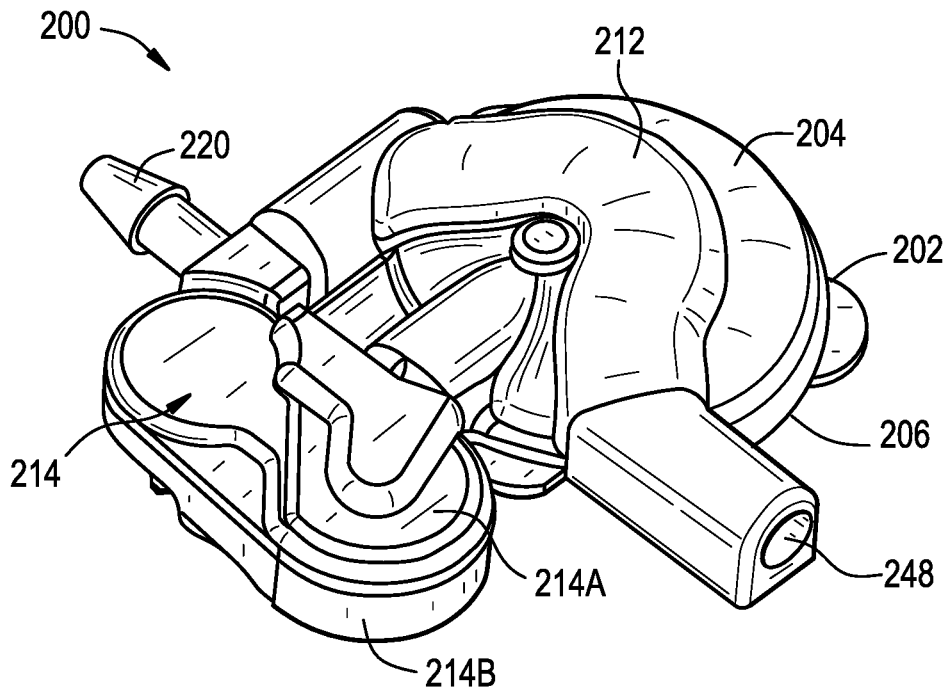
FIG. 2A is a perspective view of a flusher.
Figure 2B:
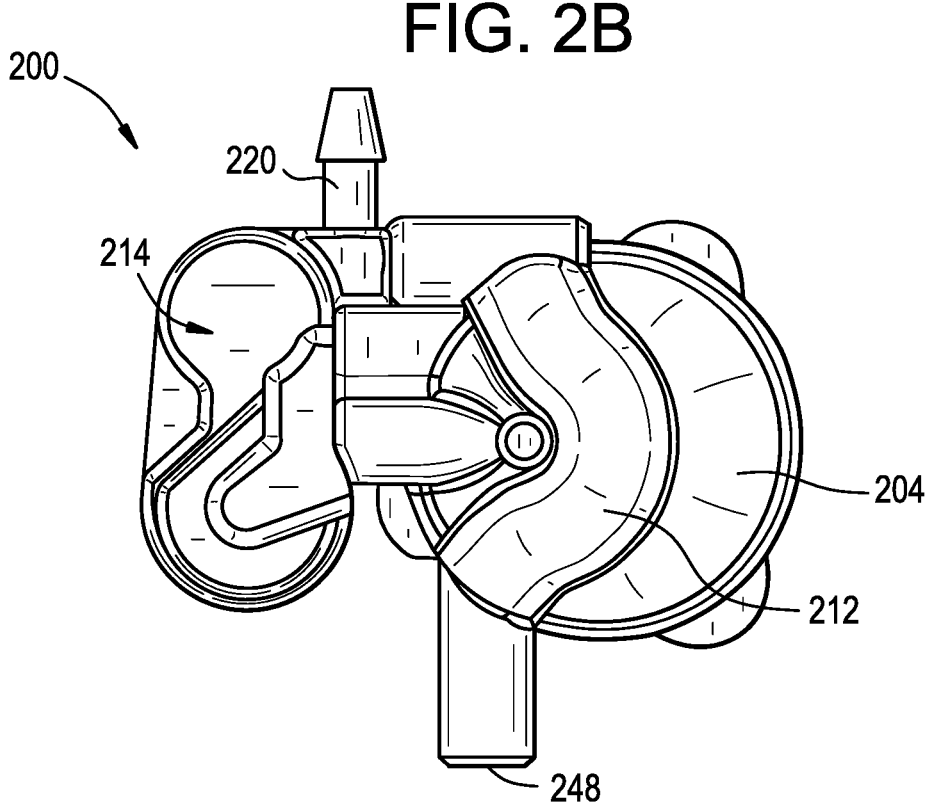
FIG. 2B is a top view of the flusher of FIG. 2A.
Figure 2C:
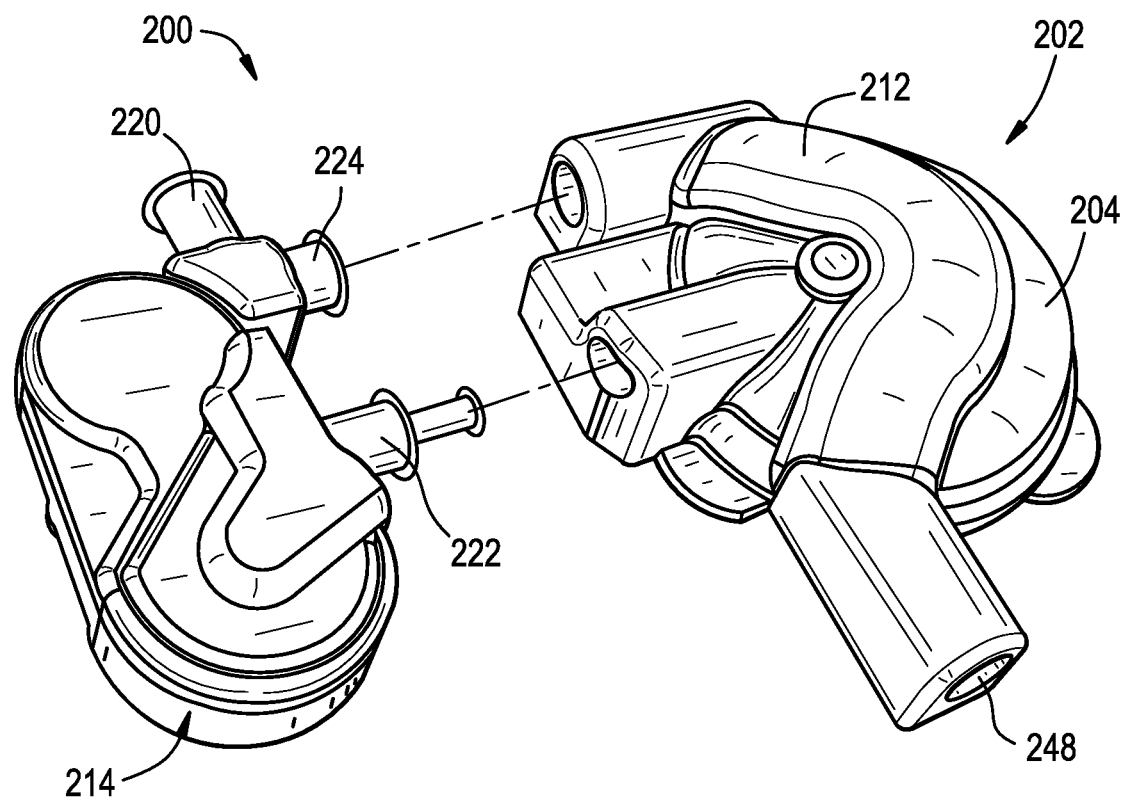
FIG. 2C is an exploded perspective view of the flusher of FIG. 2A.
Figure 2D:
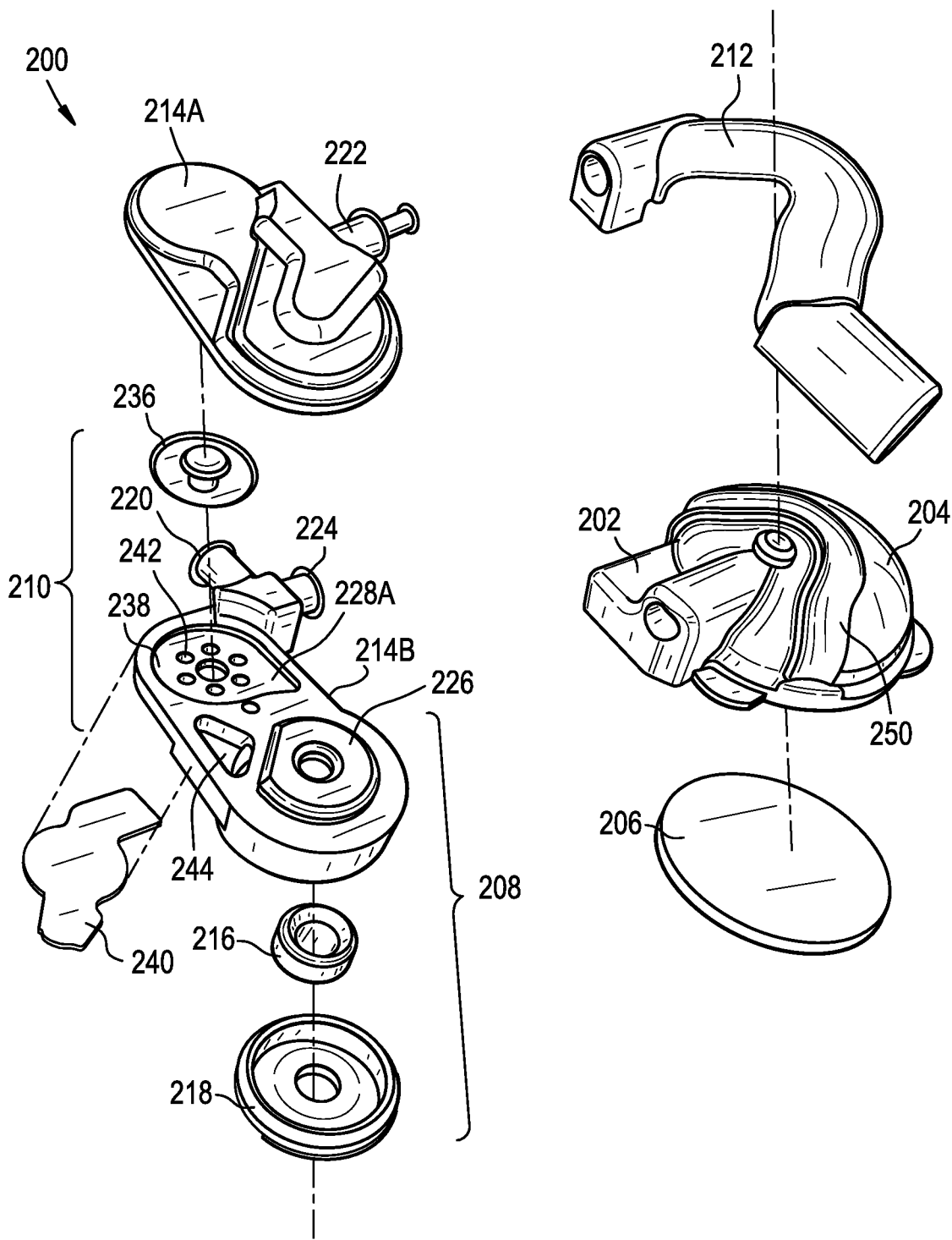
FIG. 2D is another exploded perspective view of the flusher of FIG. 2A.
Figure 2E:
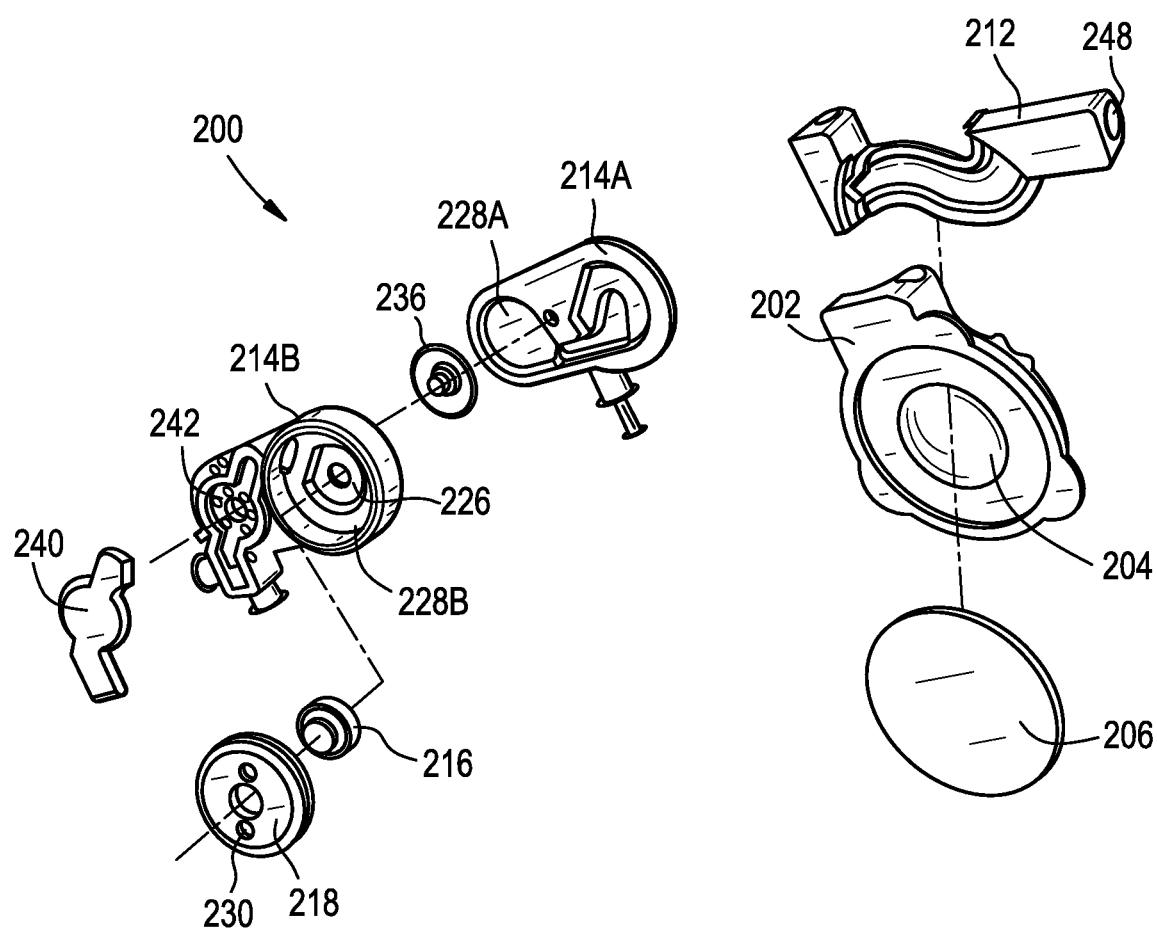
FIG. 2E is another exploded perspective view of the flusher of FIG. 2A.
Figure 2F:
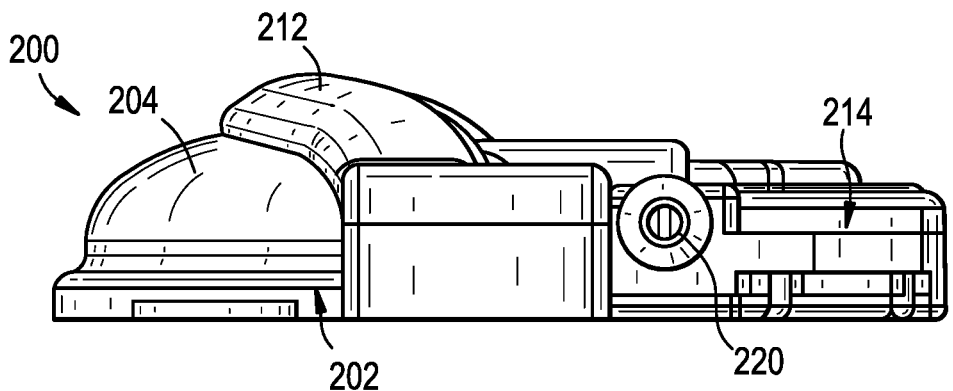
FIG. 2F is a side view of the flusher of FIG. 2A.
Figure 2G:
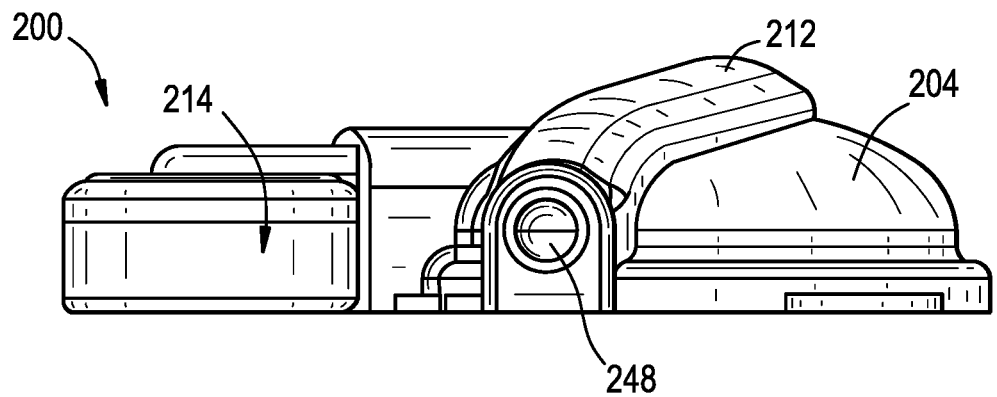
FIG. 2G is another side view of the flusher of FIG. 2A.
Figure 2H:
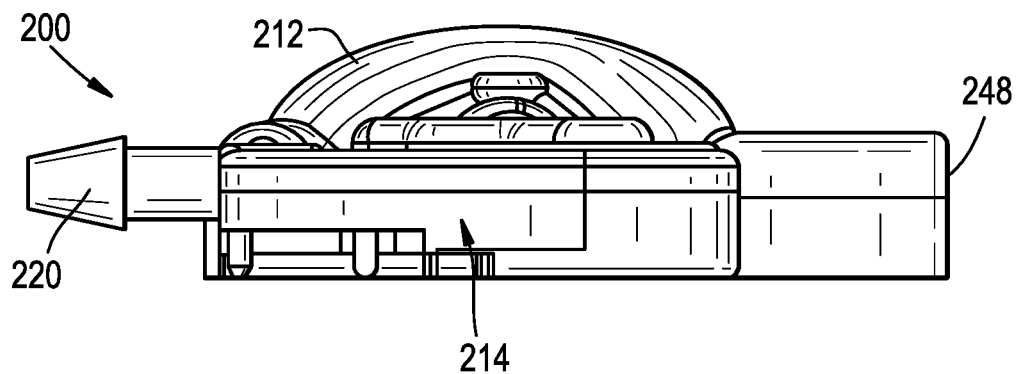
FIG. 2H is another side view of the flusher of FIG. 2A.
Figure 2I:
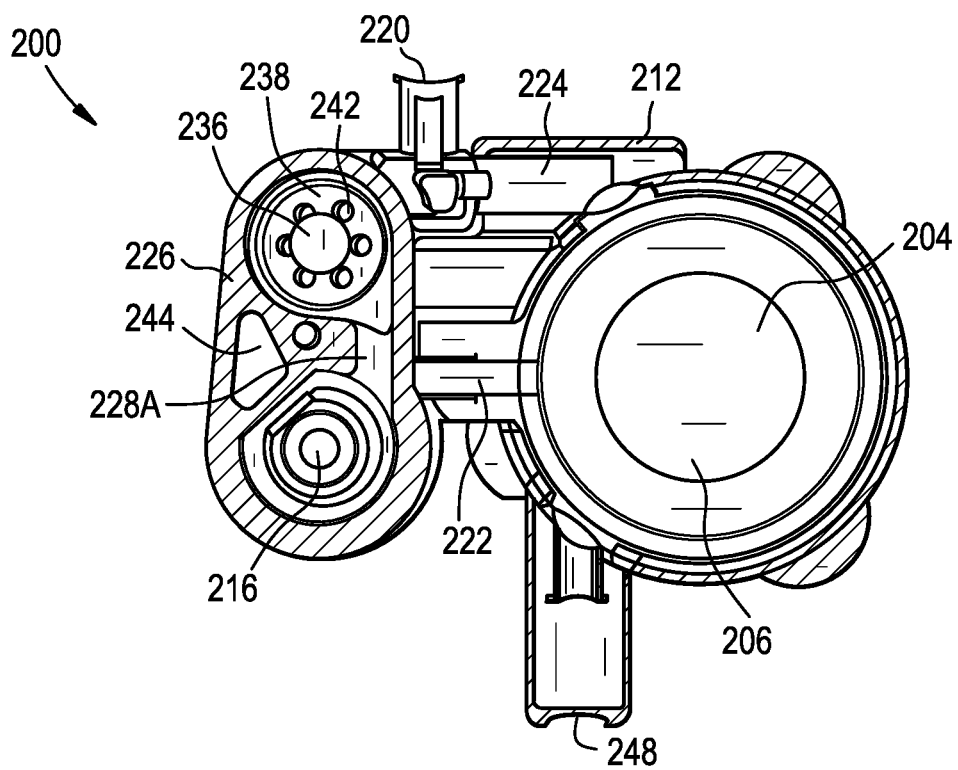
FIG. 2I is a sectional top view of the flusher of FIG. 2A.
Figure 2J:
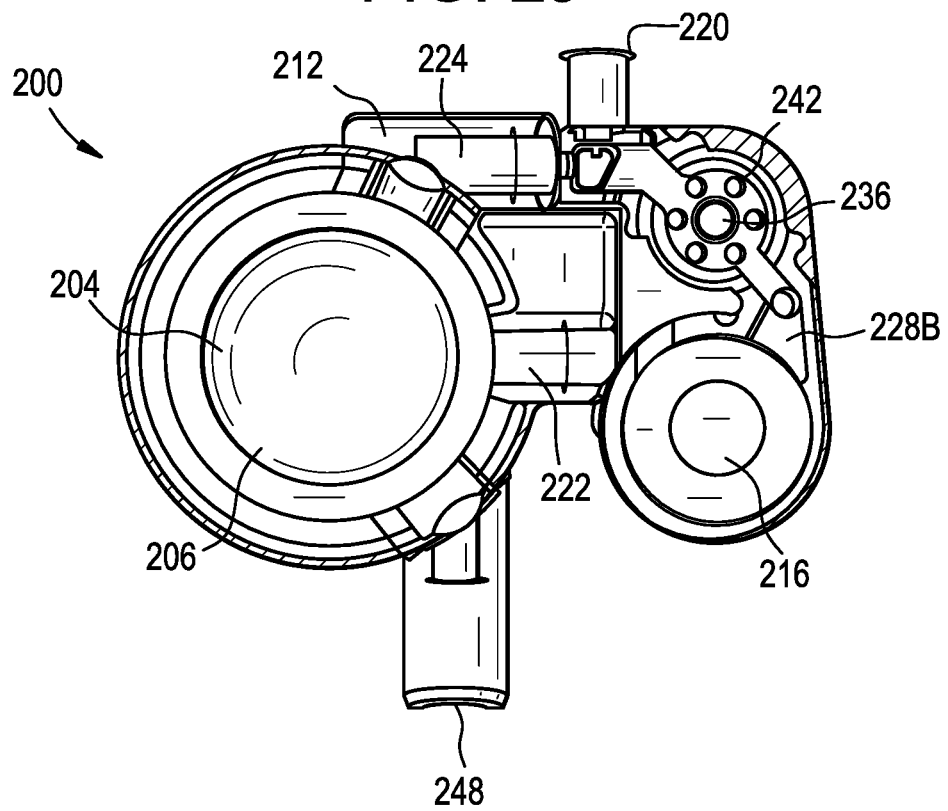
FIG. 2J is a sectional bottom view of the flusher of FIG. 2A.

As shown in FIGS. 2D-2E, the geometry of the various components of the flusher 200 can allow one or more (and in some embodiments, all) of said components to be formed using a straightforward molding process, advantageously reducing the manufacturing cost and complexity of the flusher. In some embodiments, the body 202, base plate 206, and pinch tube 212 are molded from silicone and bonded to one another using silicone RTV or other adhesive. These components can include a polyester reinforcing mesh. In some embodiments, the cartridge 214 and the barbed fittings can be formed from a polymer such as PEEK.

Figure 3A:
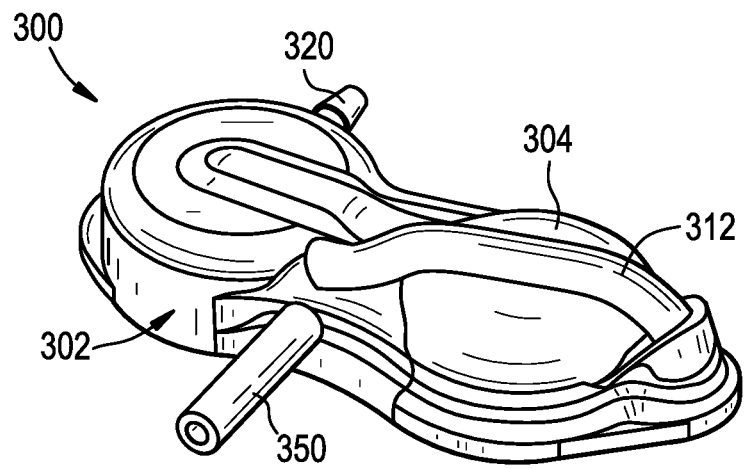
FIG. 3A is a perspective view of a flusher.
Figure 3B:
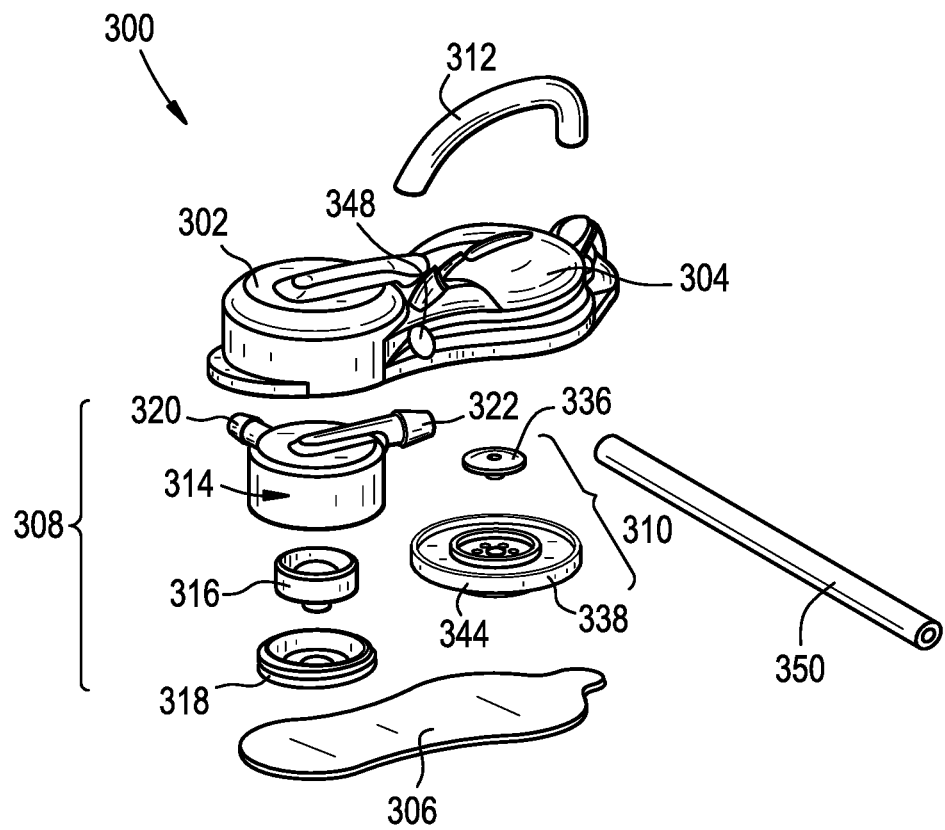
FIG. 3B is an exploded perspective view of the flusher of FIG. 3A.

The pinch tube 212 can be configured to provide a valve-less means of closing off the drain side of the shunt system during a flush operation. The pinch tube 212 extends out of the valve cartridge 214, across the top of the flush dome 204, and into a housing that defines a downstream port 248 configured to be coupled to or placed in fluid communication with a drain catheter, shunt valve, or other downstream device. A drain tube, e.g., of the type shown in FIG. 3B as element 350, can be bonded or otherwise attached or coupled to the downstream port 248. The drain tube and/or the downstream port 248 can be compatible with standard barbs, downstream attachments, valves, drainage catheters, and the like. The pinch tube 212 can be positioned such that it will naturally be compressed by a user when the user actuates the flush dome 204. The flusher 200 thus allows a single user motion, applied at a single contiguous contact area, to both seal off the drain side of the system and actuate the flush dome. In some embodiments, the pinch tube 212 can be more easily deformable than the flush dome 204 to increase the likelihood that the pinch tube is closed off when a flushing operation is performed. For example, the pinch tube 212 can be formed from a material having a lower durometer than the material used to form the flush dome 204. In an exemplary embodiment, the pinch tube 212 is formed from 30 durometer silicone while the flush dome 204 is formed from 70 durometer silicone. Closing off the pinch tube 212 prior to deflecting or actuating the flush dome 204 can advantageously maximize the flush volume and/or make the flush volume more consistent. The pinch tube 212 can be a molded component that defines only a portion of a fluid lumen. The remaining portion of the fluid lumen can be defined by the upper surface of the flush dome 204. For example, as shown, the flush dome 204 includes a trough 250 that, together with the pinch tube 212, defines a closed fluid lumen extending between the passive flow port 224 and the downstream port 248.

The flusher 200 can be operable in a passive flow mode, a flushing mode, and a refill mode.

During the passive flow mode of operation, the flush valve 216 and the refill valve 236 are both closed. Fluid from a ventricular catheter flows into the valve cartridge 214 via the upstream port 220. The fluid flows into the passive flow port 224, through the pinch tube 212, out of the flusher 200 through the downstream port 248, and then into a shunt valve, drain catheter, or other downstream component of the shunt system. Fluid also flows around the closed valve body 216 and fills the lower portion 228B of the chamber 228.

A user can initiate a flushing operation by applying pressure to the top of the flush dome 204 (e.g., by exerting downward finger pressure on the dome through a patient's skin), to collapse or compress the dome. During the flushing mode of operation, the pinch tube 212 collapses under the pressure being applied by the user to cut off fluid communication to the downstream components of the shunt system. As the flush dome 204 is depressed, the pressure in the flush dome increases, holding the refill valve 236 in the closed position. The pressure in the flush dome 204 increases until the threshold pressure of the flush valve 216 is reached, at which point the flush valve opens releasing a cough or burst of fluid into the lower chamber 228B. The collapsed pinch tube 212 prevents the burst of fluid from flowing through the passive flow port 224, and therefore the burst of fluid instead flows through the upstream port 220. This upstream "cough" or flush of fluid can be effective to clear obstructions from a ventricular catheter or other upstream component of the shunt system, or to open auxiliary flow paths in a ventricular catheter. The terms "cough" and "pulse" are used interchangeably herein to refer to the burst of fluid emitted by the flusher. The cough or pulse can be of a compressible fluid or substance or an incompressible fluid or substance. Once the burst of fluid is released, the flush valve 216 returns to the closed position.

When a flushing operation is completed and the flush dome 204 is released, the pinch tube 212 opens to reestablish flow to the downstream port 248 and the flush dome gradually returns to its raised position. During this refill mode of operation, the flush valve 216 is closed. Expansion of the flush dome 204 causes the pressure in the flush dome to drop below the pressure in the lower chamber 228B, which creates a pressure differential that causes the refill valve 236 to open. Fluid in the lower chamber 228B can then flow through the openings 242 formed in the refill plate 238 to refill the flush dome 204. The cross-sectional area of the openings 242 can be made relatively small to limit the rate at which the flush dome 204 is refilled and therefore the rate at which the flush dome expands. This can advantageously prevent debris flushed from the shunt system during the flushing operation from being sucked back in as the flush dome 204 expands. Once the flush dome 204 is refilled, the flusher 200 returns to the passive flow mode of operation.

The flusher 200 thus facilitates generation and application of a high pressure cough of fluid which flushes the ventricle side of the shunt system only. The pinch tube 212 prevents the cough of fluid from travelling through the drain side of the shunt system. In other embodiments, however, the flusher 200 can be configured to flush the drain side of the system instead or in addition.

FIGS. 3A-3G illustrate an exemplary embodiment of a flusher 300. The flusher 300 generally includes an outer shell or body 302 that defines a flush dome 304. The bottom surface of the body 302 is closed by a base plate 306 to which the body is sealed. A flush valve assembly 308 and a refill valve assembly 310 are disposed within the body 302, and a pinch tube 312 extends over the top of the flush dome 304.

The flush valve assembly 308 includes a valve cartridge 314, a valve body 316, and an adjustment disc 318. The valve cartridge 314 includes an upstream port 320 configured to be coupled to or placed in fluid communication with a ventricular catheter, a flush port 322 configured to be placed in fluid communication with the flush dome 304, and a passive flow port 324 configured to be placed in fluid communication with a passive flow lumen 326 defined by the body 302. Each of the ports 320, 322, 324 are in fluid communication with an interior chamber defined 328 by the valve cartridge 314. The upstream port 320 and/or the flush port 322 can be defined by male barbed fittings that extend radially outward from the valve cartridge 314. The barbed fittings can advantageously facilitate coupling of the flush valve assembly 308 with the body 302 (in the case of the flush port 322) or with a ventricular catheter or other shunt system component (in the case of the upstream port 320). The passive flow port 324 can be defined by an opening formed in a sidewall of the valve cartridge 314. The valve cartridge 314 and the barbed fittings can be formed as monolithic, one-piece component which can advantageously provide a high strength unit capable of withstanding high operating pressures and lateral stress on the upstream port fitting 320. High interference barbed fittings can be used to allow high pressure operation without leakage, which allows the flushing pressure to be delivered only to the flush valve and facilitates more precise and repeatable opening pressure thresholds. In some embodiments, the barbed fittings can be configured to withstand up to 120 psi.

The valve body 316 can be an umbrella-type valve, a Belleville-type valve, or the like. The valve body 316 is sandwiched between the upper wall of the chamber 328 and the adjustment disc 318 in an interference fit such that the valve body is compressed. The valve body 316 defines a substantially concave upper surface that forms a fluid-tight seal with the upper wall of the chamber 328 to seal off the flush port 322 from the upstream port 320 and the passive flow port 324 during normal operation. When sufficient pressure is applied to the upper surface of the valve body 316, the valve body deforms away from the upper wall of the chamber 328 to allow fluid communication between the flush port 322 and the upstream port 320 and between the flush port and the passive flow port 324. The threshold pressure at which the valve body 316 opens can be infinitely adjusted by adjusting the pressure exerted on the valve body by the adjustment disc 318. In the illustrated embodiment, the adjustment disc 318 is threadably mounted in the cartridge 314 such that rotating the disc in a first direction increases the compression of the valve body 316 to increase the threshold pressure, and such that rotating the disc in a second, opposite direction decreases the compression of the valve body to decrease the threshold pressure. It will be appreciated that other means of adjusting the compression of the valve body 316 can be used instead or in addition. A driving interface 330 can be formed in the bottom surface of the adjustment disc 318 to facilitate rotation of the disc by a driving tool. In the illustrated embodiment, the driving interface 330 comprises first and second opposed cylindrical recesses configured to receive corresponding first and second pins of a driving tool. The arrangement of the recesses can allow rotation of the disc 318 to be easily visualized and to be performed in a repeatable and controlled manner. The adjustment disc 318 can be adjusted in-process and locked in a desired position using an adhesive (e.g., medical grade cyanoacrylate or the like). Locking the disc 318 in place, e.g., by freezing the threads using an adhesive, can advantageously allow for the threshold pressure of the valve to be securely maintained at the desired level.

When the valve body 316 is sealed against the upper wall of the chamber 328, fluid can flow from the upstream port 320, into the chamber, around the outside of the closed valve body, and into the passive flow port 324.

The flush valve assembly 308 can be positioned within a cavity 332 defined in the body 302 of the flusher 300 such that the upstream port 320 protrudes through a sidewall of the body and such that the flush port 322 extends into a passage 334 that connects the cavity to the flush dome 304. When the flush valve assembly 308 is disposed in the body 302, the passive flow port 324 is aligned with the passive flow channel 326 defined in the body.

The refill valve assembly 310 includes a refill valve 336 and a refill plate 338. The refill plate 338 is mounted in the body 302 beneath the flush dome 304. A passive flow channel 340 extends through the refill plate 338 and is in fluid communication with the passive flow channel 326 of the body 302 at one end and the pinch tube 312 at the other end. The refill valve 336 is operable to selectively place the passive flow channel 340 in fluid communication with the interior of the flush dome 304, for example to refill the flush dome after a flushing operation is performed. In the illustrated embodiment, the refill valve 336 is an umbrella valve that includes a valve stem and a valve head. The stem is mounted within a valve guide formed in the refill plate 338. A plurality of openings 342 are formed in the plate 338 around the circumference of the valve guide. When the refill valve 336 is closed, the valve head covers the plurality of openings 342 and prevents fluid communication between the passive flow channel 340 and the flush dome 304. When the refill valve 336 is opened, the valve head is lifted off of the openings 342 such that fluid can flow between the passive flow channel 340 and the flush dome 304.

Figure 3C:
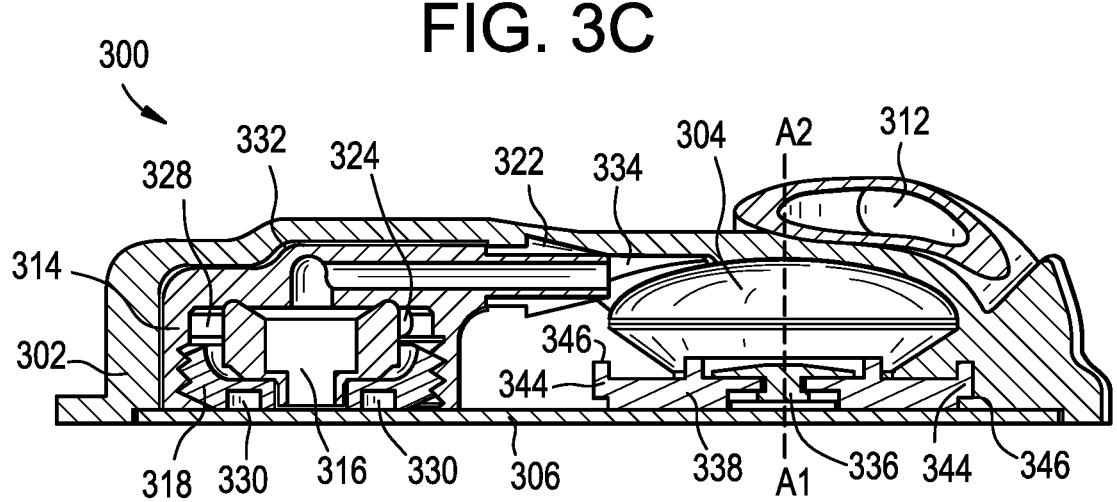
FIG. 3C is a longitudinal sectional view of the flusher of FIG. 3A.
Figure 3D:
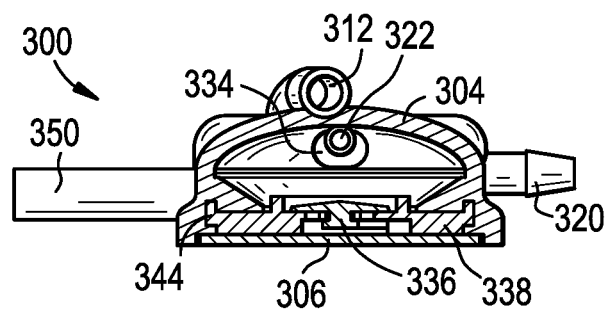
FIG. 3D is a lateral sectional view of the flusher of FIG. 3A.
Figure 3E:
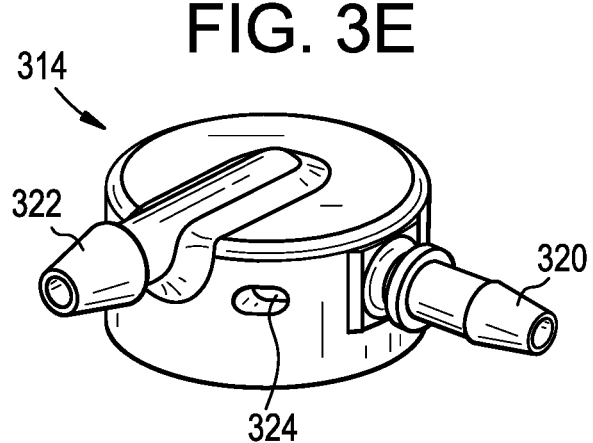
FIG. 3E is a perspective view of a valve cartridge of the flusher of FIG. 3A.

As perhaps best shown in FIG. 3C, the refill valve 336 is disposed beneath the flush dome 304 and oriented such that the axis A1 along which the valve opens and closes is substantially parallel to the axis A2 along which the flush dome is actuated. In other words, when an actuation force is applied to the flush dome 304 during a flushing operation, the primary component of the actuation force acts in the same direction as the valve closing direction. Also, the stacked nature of the refill valve 336 and flush dome 304 allows pressure in the flush dome to act directly on the refill valve, helping ensure that the refill valve is closed when the flush dome is actuated. The stacked arrangement also reduces the overall length and profile of the flusher 300.

The refill plate 338 can be rigid, semi-rigid, or flexible. The refill plate 338 can mechanically interlock with the body 302 to provide a robust connection capable of withstanding high operating pressures. As shown, the refill plate 338 can be disc-shaped and can include a sidewall that extends about a circumference of the plate and protrudes radially-outward and axially upward to define a lip 344 that is received within a corresponding annular recess or undercut 346 formed in the body 302. The body 302 can be formed from a flexible material to allow the body to be stretched over the lip 344 of the refill plate 338 during assembly. In some embodiments, the body 302 is molded from silicone and bonded to the refill plate 338 using silicone RTV or other adhesive. The base plate 306 can likewise be bonded to the body 302 and/or to the refill plate 338 using silicone RTV or the like.

The base plate 306 can be formed from silicone and can include a polyester reinforcing mesh.

The pinch tube 312 can be configured to provide a valve-less means of closing off the drain side of the shunt system during a flush operation. The pinch tube 312 extends out of the body 302, across the top of the flush dome 304, and into a coupling where it is placed in fluid communication with a downstream port 348 configured to be coupled to or placed in fluid communication with a drain catheter, shunt valve, or other downstream device (e.g., via a drain tube 350 as shown). The pinch tube 312 can be positioned such that it will naturally be compressed by a user when the user actuates the flush dome 304. The flusher 300 thus allows a single user motion, applied at a single contiguous contact area, to both seal off the drain side of the system and actuate the flush dome. In some embodiments, the pinch tube 312 can be more easily deformable than the flush dome 304 to increase the likelihood that the pinch tube is closed off when a flushing operation is performed. For example, the pinch tube 312 can be formed from a material having a lower durometer than the material used to form the flush dome 304. In an exemplary embodiment, the pinch tube 312 is formed from 30 durometer silicone while the flush dome 304 is formed from 70 durometer silicone.

Figure 3F:
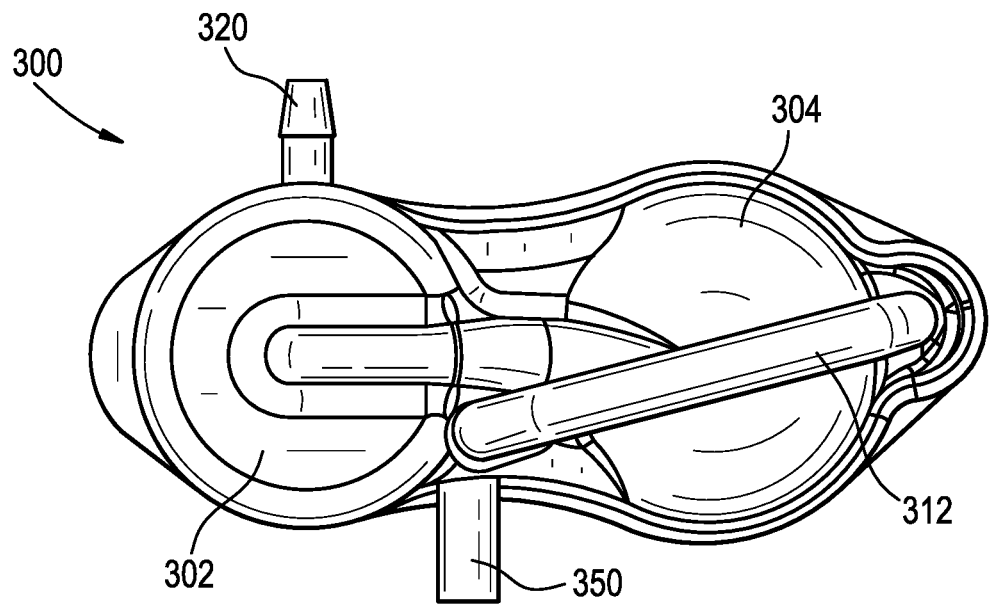
FIG. 3F is a top view of the flusher of FIG. 3A.
Figure 3G:
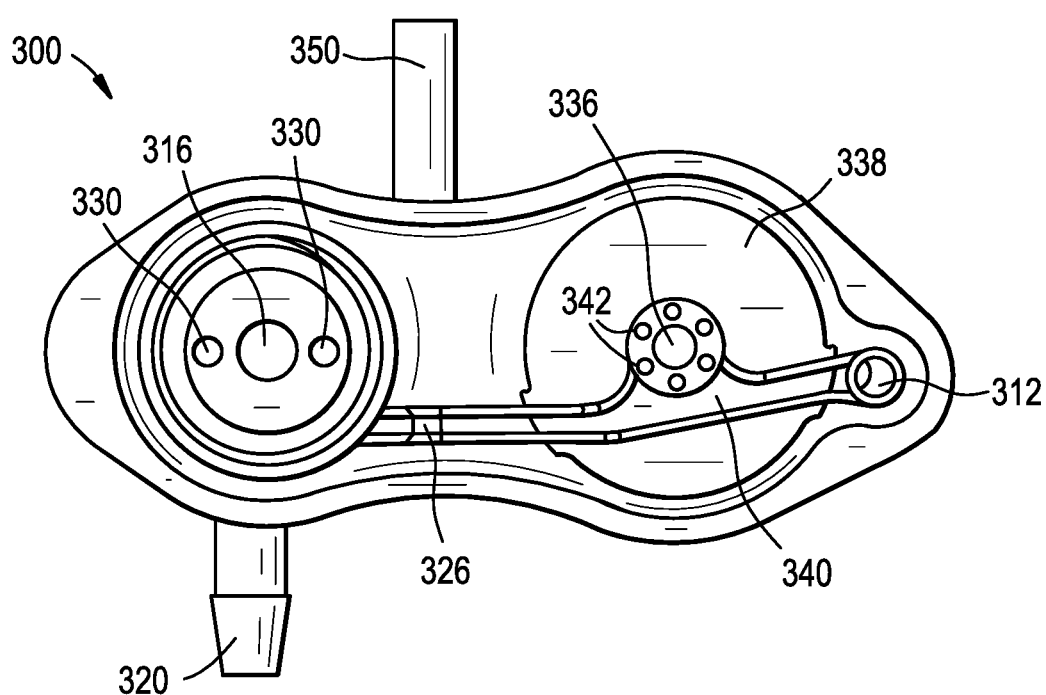
FIG. 3G is a bottom view of the flusher of FIG. 3A with a base plate removed.

As shown in FIGS. 3F and 3G, the flusher 300 employs a substantially T-shaped configuration in which the longitudinal axis of the flusher body 302 extends perpendicular to the longitudinal axis of the upstream port 320 and the longitudinal axis of the drain tube 350. This can advantageously allow the flusher 300 to be used with existing shunt systems without increasing the distance between the anchor and the shunt valve. The T-configuration can thus reduce or eliminate the need to add length to the overall shunt system, and allows the flusher 300 to be positioned more proximate to an incision over the burr hole that is typically used when implanting shunt systems.

The flusher 300 can be operable in a passive flow mode, a flushing mode, and a refill mode.

During the passive flow mode of operation, the flush valve 316 and the refill valve 336 are both closed. Fluid from a ventricular catheter flows into the valve cartridge 314 via the upstream port 320. The fluid flows around the closed valve body 316 and into the passive flow port 324 of the valve cartridge 314. From there, the fluid flows through the passive flow channel 326 of the body 302 and through the passive flow channel 340 of the refill plate 338, past the closed refill valve 336. The fluid then flows through the pinch tube 312, into the drain tube 350, and then into a shunt valve, drain catheter, or other downstream component of the shunt system.

A user can initiate a flushing operation by applying pressure to the top of the flush dome 304 (e.g., by exerting downward finger pressure on the dome through a patient's skin), to collapse or compress the dome. During the flushing mode of operation, the pinch tube 312 collapses under the pressure being applied by the user to cut off fluid communication to the drain tube 350 and the downstream components of the shunt system. As the flush dome 304 is depressed, the pressure in the flush dome increases, holding the refill valve 336 in the closed position. The pressure in the flush dome 304 increases until the threshold pressure of the flush valve 316 is reached, at which point the flush valve opens releasing a cough or burst of fluid into the valve cartridge 314. The collapsed pinch tube 312 prevents the burst of fluid from flowing through the passive flow channels 326, 340, and therefore the burst of fluid instead flows through the upstream port 320. This upstream "cough" or flush of fluid can be effective to clear obstructions from a ventricular catheter or other upstream component of the shunt system, or to open auxiliary flow paths as described further below. Once the burst of fluid is released, the flush valve 316 returns to the closed position.

When a flushing operation is completed and the flush dome 304 is released, the pinch tube 312 opens to reestablish flow to the downstream port 348 and the flush dome gradually returns to its raised position. During this refill mode of operation, the flush valve 316 is closed. Expansion of the flush dome 304 causes the pressure in the flush dome to drop below the pressure in the passive flow channel 340, which creates a pressure differential that causes the refill valve 336 to open. Fluid flowing through the passive flow channel 340 can then flow through the openings 342 formed in the refill plate 338 to refill the flush dome 304. The cross-sectional area of the openings 342 can be made relatively small to limit the rate at which the flush dome 304 is refilled and therefore the rate at which the flush dome expands. This can advantageously prevent debris flushed from the shunt system during the flushing operation from being sucked back in as the flush dome 304 expands. Once the flush dome 304 is refilled, the flusher 300 returns to the passive flow mode of operation.

The flusher 300 thus facilitates generation and application of a high pressure cough of fluid which flushes the ventricle side of the shunt system only. The pinch tube 312 prevents the cough of fluid from travelling through the drain side of the shunt system. In other embodiments, however, the flusher 300 can be configured to flush the drain side of the system instead or in addition.

FIGS. 4A-4E illustrate an exemplary embodiment of a catheter 400 that can be used with a shunt system (e.g., with the shunt system 100 described above). The catheter 400 includes a plurality of inlet holes formed at a distal tip end of the catheter configured to be disposed within a patient's ventricle. While a single-lumen, single-tip catheter is shown, it will be appreciated that the catheter can be a multi-lumen catheter and/or a multi-tip catheter. For example, the catheter can be a dual lumen catheter with two independent lumens that extend the full length of the catheter. By way of further example, the catheter can be a split-tip catheter having first and second tips at the distal end that merge into a single lumen that extends through the remainder of the catheter.

The plurality of inlet holes includes one or more primary holes 402 which form pathways through which fluid external to the catheter 400 can enter an inner lumen of the catheter. The plurality of inlet holes also includes one or more auxiliary holes 404 which are initially blocked such that fluid external to the catheter 400 cannot pass through the auxiliary holes into an inner lumen of the catheter. Rather, fluid can only pass through the auxiliary holes 404 after they are forced open (e.g., by a flushing operation of one of the flushers disclosed herein). The auxiliary holes 404 are initially blocked by a membrane 406. In some embodiments, the membrane 406 can be disposed over the exterior surface of the catheter 400. The membrane 406 can be formed from a variety of implantable and biocompatible materials, such as silicone. The membrane 406 can be stretched across the openings 404 and attached to the catheter 400 under tension, such that penetration of the membrane results in a tear in which opposed sides of the tear move out of the way of the underlying hole. The membrane 406 can be stretched over the auxiliary holes 404 in a variety of directions or orientations, which can allow for the tear produced when the membrane is ruptured to have some directionality (i.e., to define an opening that faces in a particular direction). The stretched membrane 406 can be attached to the catheter 400 in various ways. For example, the membrane 406 can be thermally welded to the catheter 400 using a heat punch, mechanically coupled to the catheter using O-rings disposed around the membrane and the catheter, or molded into or onto the catheter. In some embodiments, a plurality of auxiliary holes can be provided, each having a membrane stretched in a different direction. The thickness of the membrane, the degree of tension applied to the membrane, and the material from which the membrane is formed can be selected to control the force required to tear the membrane. In some embodiments, the membrane can be configured to burst at an opening pressure of about 5 psi to about 15 psi. In some embodiments, the membrane is formed from silicone and has a thickness of about 0.001 inches.

The catheter 400 can include a stiffening sleeve 401 disposed over the membrane. The stiffening sleeve 401 can include an opening 403 that is aligned with the auxiliary hole 404, and can be positioned in a recessed portion 405 of the catheter such that the stiffening sleeve and the catheter define a continuous, smooth outer surface. The stiffening sleeve 401 can advantageously prevent the catheter 400 from bending or ballooning under the pressure of a flushing cough while at the same time focusing the cough pressure on the membrane 406. The catheter 400 can also include a bullet-tip plug 409 that seals the terminal distal end of the catheter.

In some embodiments, the catheter 400 can be manufactured by extruding a silicone tube to form a catheter main body 407 with the desired inside and outside diameters. The tube can then be cut to the desired length. The distal portion 411 of the catheter, including the recess 405 for the stiffening sleeve 401, can then be formed on one end of the tube using a silicone overmolding process. Primary and auxiliary holes 402, 404 can be added to this distal portion 411 later in a separate drilling step. Once the auxiliary hole 404 is formed, a silicone membrane 406 can be molded over the opening. Alternatively, the membrane 406 and the auxiliary hole 404 defined beneath the membrane 406 can be formed simultaneously by molding them as one monolithic, continuous part formed from silicone or other materials. In other words, the auxiliary hole 404 can be initially formed as a non-full-thickness or blind hole, with the remaining thickness defining the membrane 406. The stiffening sleeve 401 can be formed from a PEEK extrusion and a laser cutting process can be used to form the window 403 in the stiffening sleeve. The stiffening sleeve 401 can be positioned over the membrane 406 and bonded in place using RTV silicone or the like. The distal plug 409 can be molded as a separate silicone component and then sealed to the distal end of the catheter using RTV silicone or the like.

Any one or more components of the catheter 400 can be formed from a radiopaque material or can have a radiopaque material embedded or impregnated therein to facilitate visualization using various imaging techniques. In some embodiments, barium sulfate or other radiopaque materials can be molded into the distal portion 411 of the catheter, the main body 407 of the catheter, the stiffening sleeve 401, the membrane 406, and/or the distal tip 409.

The catheter 400 can include various features for facilitating a determination as to whether the membrane 406 has been opened using CT, X-ray, or other imaging techniques. For example, a thin ribbon of radiopaque material can be printed on the membrane. When the membrane opens, radiographic images of the implanted catheter can show the ribbon of material being torn away or separated. The ribbon can be deposited or printed on the membrane in an ultra-thin layer using nanotechnology. The ribbon can extend longitudinally, laterally, diagonally, or in any other direction or directions across the auxiliary opening, and can be formed in a matrix or any other pattern.

Figure 4C:
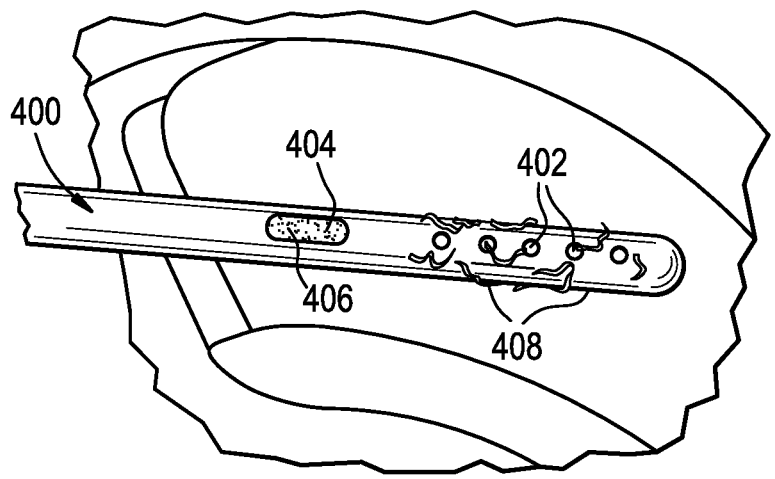
FIG. 4C is a perspective view of an implanted catheter of FIG. 4A with obstructions blocking primary inlet ports of the catheter.
Figure 4D:
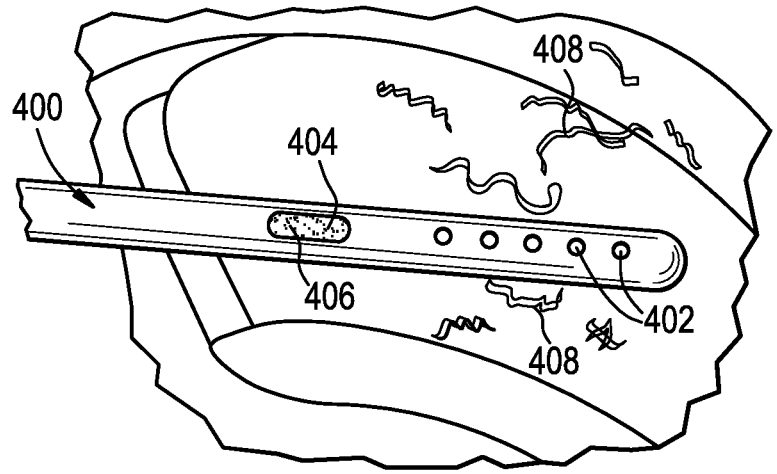
FIG. 4D is a perspective view of the catheter of FIG. 4C with the obstructions cleared by a flushing operation.
Figure 4E:
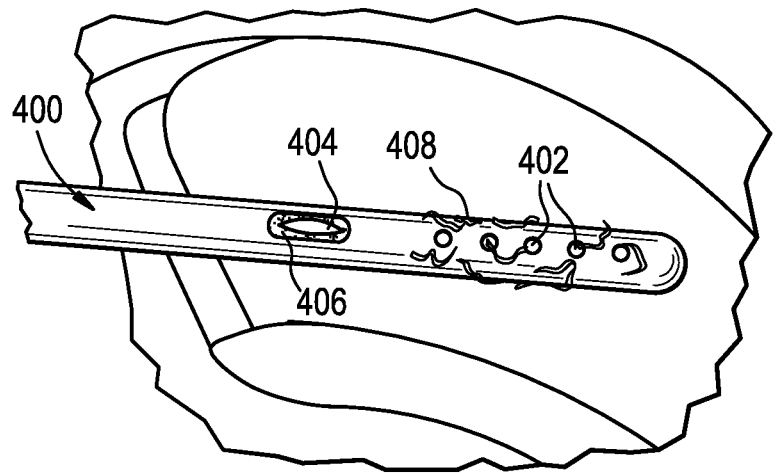
FIG. 4E is a perspective view of the catheter of FIG. 4C with an auxiliary inlet port of the catheter having been opened by a flushing operation.

In use, the catheter 400 is implanted in a patient with the distal tip of the catheter disposed in the patient's ventricle. Fluid enters the primary holes 402 of the catheter and flows through the inner lumen of the catheter to a downstream portion of the shunt system (e.g., a flusher, a valve, and/or a drain catheter). When the primary holes 402 become clogged or obstructed (e.g., as shown in FIG. 4C), or at any other time a user so desires, a flusher can be actuated to deliver a pressurized cough of fluid through the inner lumen of the catheter. The cough of fluid can dislodge obstructions 408 from the clogged primary holes 402 (e.g., as shown in FIG. 4D) and/or cause the membrane 406 covering one or more auxiliary holes 404 to burst (e.g., as shown in FIG. 4E). In other words, flushing the catheter can open the auxiliary inlet ports 404 to provide a secondary fluid pathway into the catheter, e.g., when the primary fluid pathway becomes clogged or obstructed.

Figure 5:
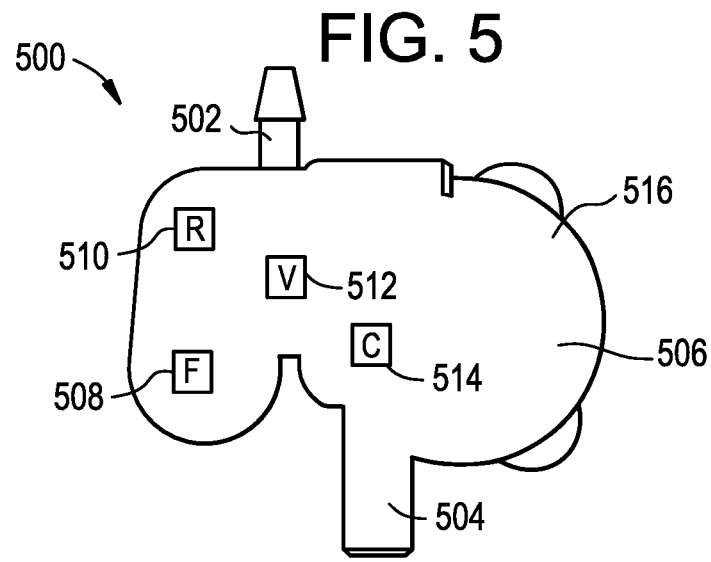
FIG. 5 is a schematic top view of a flusher.

FIG. 5 illustrates an exemplary flusher 500 that can be used with a shunt system (e.g., with the shunt system 100 described above). As shown, the flusher 500 can include an upstream port 502 configured to be coupled to or placed in fluid communication with a ventricular catheter and a downstream port 504 configured to be coupled to or placed in fluid communication with a drain catheter or other downstream device. The flusher 500 can include a flush dome or reservoir 506 that can contain fluid and can be actuated to flush a cough of fluid through the upstream port 502, the downstream port 504, or both. The flusher 500 can include a flush valve 508 that controls the release of the cough of fluid. The flusher 500 can include a refill valve 510 that controls refilling of the flush dome 506 after a flushing operation. The flusher 500 can include a shunt valve 512 that controls draining of fluid through the shunt system, e.g., to control draining of fluid between a brain ventricle and a drain site of a patient. The flusher 500 can include a control 514 that can be used to selectively activate or deactivate one or more functions of the flusher. The components of the flusher 500 can be contained within a housing 516.

While the illustrated flusher 500 includes a flush dome 506, flush valve 508, refill valve 510, shunt valve 512, and control 514 all housed within a single housing 516, it will be appreciated that one or more of said components can be formed in a separate housing or structure, which can be directly assembled with the housing 516 or disposed remotely therefrom. In addition, it will be appreciated that one or more of said components can be omitted altogether.

The illustrated flusher 500 includes an internal shunt valve 512. Integrating the shunt valve with the flusher can advantageously reduce the number of implanted components, reduce the invasiveness of using and installing the shunt system, reduce the cost and complexity of the shunt system, or achieve other advantages that will be appreciated from the description below. The shunt valve 512 can be or can include the features of any of a variety of known or commercially-available shunt valves, including programmable shunt valves and non-invasively adjustable shunt valves.

Incorporating a control 514 that can be used to selectively activate or deactivate one or more functions of the flusher 500 into the system can provide various advantages.

In some embodiments, the control 514 can allow non-invasive activation or deactivation of the flushing function. For example, the control 514 can lock the flush valve 508 in a closed position to disable all flushing through the system. This can be used, for example, to limit use of the flusher to controlled environments or to selected individuals. In one scenario, a patient could be prevented from flushing the system while a clinician would be able to actuate the control 514 to enable flushing.

In some embodiments, the control 514 can allow non-invasive activation or deactivation of the auxiliary flow port function. For example, the control 514 can limit the flushing pressure or volume to an amount that is insufficient to open an auxiliary flow port in a catheter of the system. As another example, the control 514 can use mechanical or hydraulic means to isolate the auxiliary flow port from the flushing pressure. This can be used, for example, to ensure that the auxiliary flow port is only opened when specifically intended, while still allowing flushing operations to be performed in an effort to clear obstructions through the primary flow ports of the catheter. In one scenario, a patient would be free to perform flushing operations to clear debris from the primary flow ports, but would be prevented by the control 514 from performing a flushing operation to open the auxiliary flow port(s). Rather, only a clinician or other individual capable of adjusting the control 514 would be able to open the auxiliary flow ports.

In some embodiments, the catheter can include isolated first and second fluid lumens, with the first fluid lumen being in communication with a primary flow port and the second fluid lumen being in fluid communication with an auxiliary flow port. The control 514 can selectively switch which fluid lumen is placed in fluid communication with the flush dome 506 to control whether a flushing operation will clear a primary flow port or open an auxiliary flow port.

In some embodiments, the control 514 can adjust the opening pressure of the flush valve 508 to control the pressure and force of the resulting cough of fluid. The control 514 can limit the pressure to a value that is insufficient to open an auxiliary flow port.

In some embodiments, the control 514 can limit the volume of the flush, e.g., by controlling the refill valve 510 to limit refill of the flush dome 506, or by moving a physical divider within the flush dome 506, to control the volume of the resulting cough of fluid. The control 514 can limit the volume to a value that is insufficient to open an auxiliary flow port.

In some embodiments, the control 514 can facilitate a flushing operation and/or allow non-invasive control of flushing directionality. For example, the control 514 can close a downstream valve to direct the flush through the upstream port 502 only, or close an upstream valve to direct the flush through the downstream port 504 only. This can allow pinch tubes and other structures for blocking flow in the undesired direction to be omitted from the flusher.

While the control 514 is shown as being formed integrally with the flusher 500, it can alternatively or additionally be formed as a separate component or be formed integrally with the catheter or other component of a shunt system.

In the discussion that follows, a number of flushers, catheters, and other devices are described that include an integrated shunt valve and/or a control of the type described above. The features illustrated or described in connection with one exemplary device or embodiment may be combined with the features of other devices or embodiments.

Figure 6:
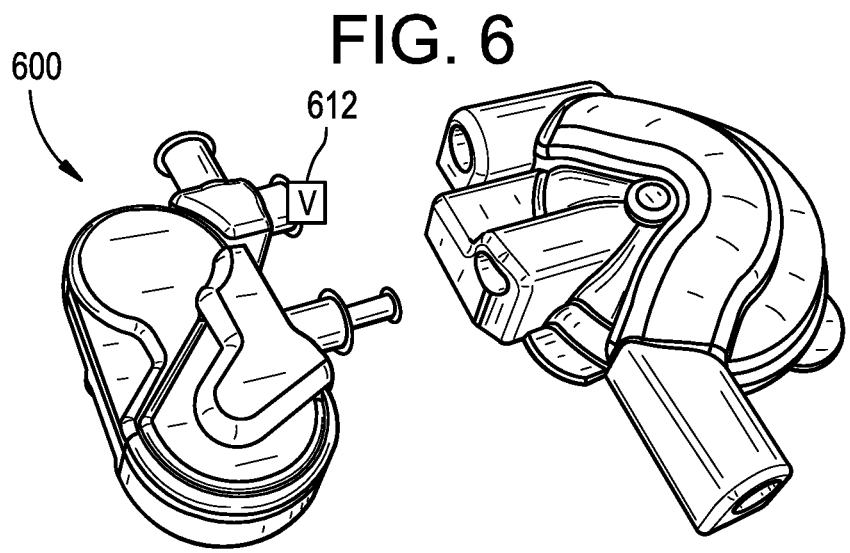
FIG. 6 is a partially-exploded perspective view of a flusher.

FIG. 6 illustrates an exemplary flusher 600. The flusher 600 is similar to the flusher 200 described above, except that it also includes an integrated shunt valve 612 disposed in-line with the passive flow port of the cartridge. The shunt valve 612 can be non-invasively adjustable, e.g., magnetically-adjustable. The shunt valve 612 can be an umbrella valve, a ball-and-spring valve, a one-way pressure controlled diaphragm valve, etc. The shunt valve 612 can be a slit valve with a predicable opening pressure. The shunt valve 612 can be incorporated into a portion of the cartridge housing and can be provided as part of a kit with multiple modular cartridge housing portions, each having a different shunt valve 612 opening pressure. A cartridge portion having the desired opening pressure can be selected from the kit and assembled to the flusher 600 before use.

Figure 7:
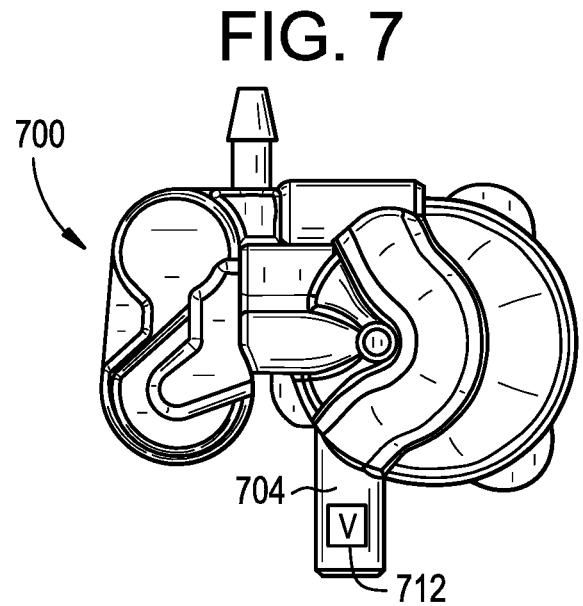
FIG. 7 is a top view of a flusher.

FIG. 7 illustrates an exemplary flusher 700. The flusher 700 is similar to the flusher 200 described above, except that it also includes an integrated shunt valve 712 disposed in-line with the drain port 704. The shunt valve 712 can be non-invasively adjustable, e.g., magnetically-adjustable. The shunt valve 712 can be an umbrella valve, a ball-and-spring valve, a one-way pressure controlled diaphragm valve, etc. The shunt valve 712 can be a slit valve with a predicable opening pressure. The shunt valve 712 can be incorporated into a modular drain port and can be provided as part of a kit with multiple modular drain ports, each having a different shunt valve 712 opening pressure. A drain port having the desired opening pressure can be selected from the kit and assembled to the flusher 700 before use.

Figure 8:
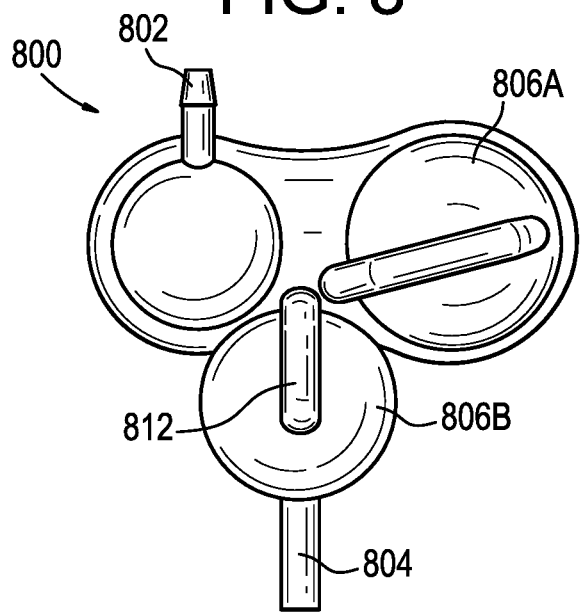
FIG. 8 is a schematic sectional top view of a flusher.

FIG. 8 illustrates an exemplary flusher 800 that includes an upstream or ventricle port 802, a downstream or drain port 804, and a first flush dome or reservoir 806A. The flusher 800 can include a flush valve, a refill valve, a shunt valve, and/or a control of the type described herein. The illustrated flusher 800 includes a shunt valve 812 in-line with the drain port 804. The flusher 800 includes a second flush dome 806B for flushing the drain side of the system, disposed downstream from the shunt valve 812. Actuation of the second flush dome 806B can urge a cough of fluid through the drain side of the system. The shunt valve 812 can be a check valve to prevent the flushing cough from traveling upstream. The second flush dome 806B can act as a shunt tap. For example, the second flush dome 806B can be penetrable by a needle to inject fluid into the system or to withdraw fluid from the system. The second flush dome 806B can include a rigid plate or shield to prevent over-insertion of the shunt tap needle. In some embodiments, the second flush dome 806B can instead be configured to flush the upstream side of the system, but with a flush volume or flush pressure less than that of the first flush dome 806A, such that actuation of the second flush dome 806B does not open auxiliary flow paths through the ventricular catheter. In some embodiments, the direction of the flush generated by the second flush dome 806B can be controlled by a setting, either upon implantation or with a control switched from outside the patient.

Figure 9:
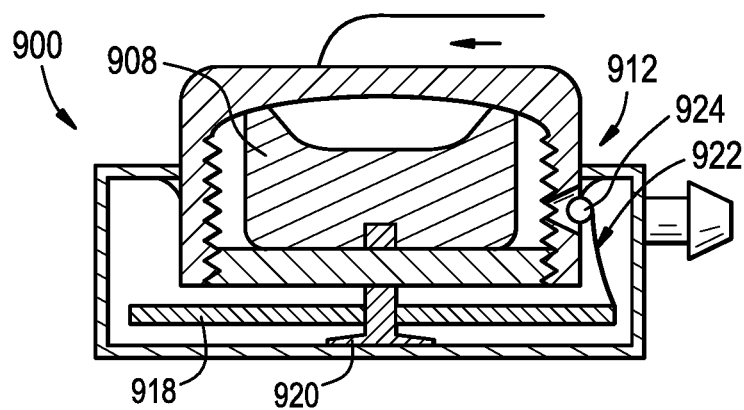
FIG. 9 is a sectional side view of a flusher.

FIG. 9 illustrates a portion of an exemplary flusher 900. The flusher 900 is similar to the flusher 200 described above, except that it also includes an integral shunt valve 912 disposed adjacent to the flush valve 908. A magnetically-movable rotor 918 can be positioned below the flush valve 908. The rotor 918 can be configured to rotate about a spindle 920 to adjust the preload on a spring 922 supporting a ball-in-cone type valve 924. The rotor 918 can define a stepped or ramped surface having a progressively increasing height about the circumference of the rotor. Alternatively, or in addition, the rotor 918 can define a stepped or ramped circumferential surface such that the radius of the rotor changes about the circumference of the rotor. An external magnetic field can be applied to the rotor 918 to turn the rotor and align a specific portion of the rotor with the spring 922. Aligning a taller or radially-larger portion of the rotor 918 with the spring 922 can compress the spring to increase the pressure on the ball 924 and increase the opening pressure of the shunt valve 912. Aligning a shorter or radially-smaller portion of the rotor 918 with the spring 922 can relax the spring to decrease the pressure on the ball 924 and decrease the opening pressure of the shunt valve 912. The shunt valve 912 is disposed to control fluid flow through the passive flow path of the flusher 900.

Figure 10:
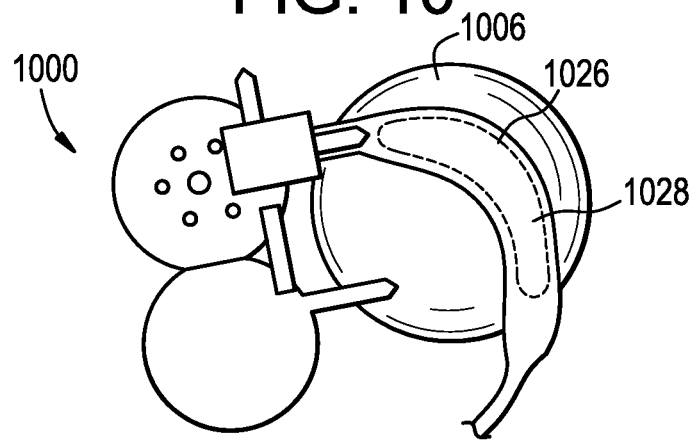
FIG. 10 is a schematic top view of a flusher.

FIG. 10 illustrates an exemplary flusher 1000. The flusher 1000 is similar to the flusher 200 described above, except that the pinch tube can serve as a shunt tap 1026. A needle guard 1028 can be positioned between the pinch tube and the flush dome 1006 to prevent the shunt tap needle from penetrating into the flush dome. The needle guard 1028 can be formed by a rigid plate, e.g., formed from a polymer such as PEEK or a metal such as titanium, stainless steel, or cobalt chromium.

Figure 11A:
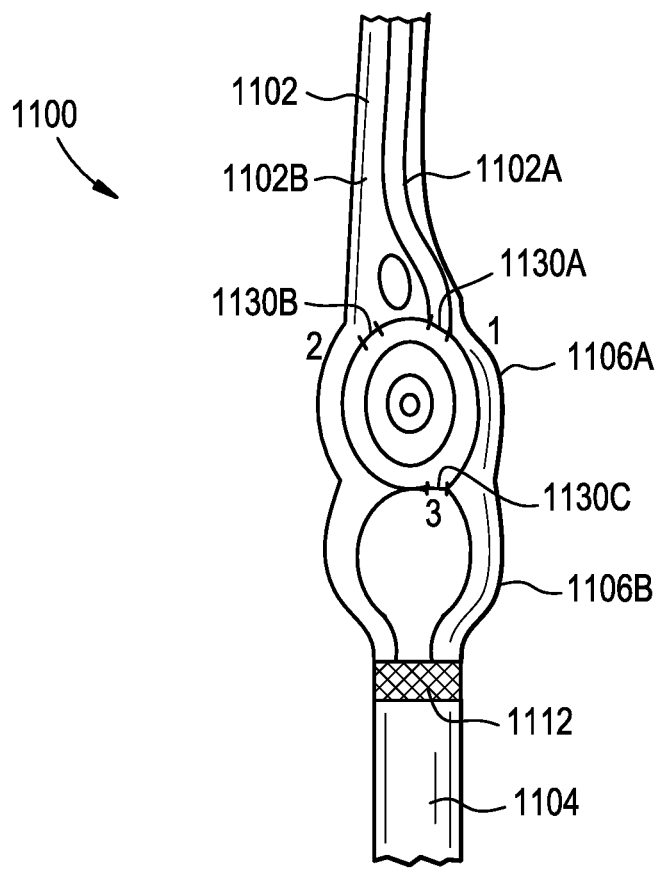
FIG. 11A is a schematic sectional top view of a flusher.

FIG. 11A illustrates an exemplary flusher 1100 that includes an upstream or ventricle port 1102, a downstream or drain port 1104, and a flush dome or reservoir 1106A. The upstream port 1102 is a "Y-entry" port in which first and second fluid lumens 1102A, 1102B of the upstream port are coupled to the flush dome 1106A. The first and second fluid lumens 1102A, 1102B can merge into a single lumen in the housing of the flusher 1100 or in the ventricular catheter.

A first valve 1130A controls fluid communication between the first fluid lumen 1102A and the flush dome 1106A and is normally open, but closes when the flush dome is pressed. A second valve 1130B controls fluid communication between the second fluid lumen 1102B and the flush dome 1106A and is normally closed, but opens when the flush dome is pressed. A third valve 1130C controls fluid communication between the flush dome 1106A and the downstream portion of the flusher and is normally open but closes when the flush dome is pressed. The downstream portion of the flusher 1100 can include a shunt tap dome 1106B and a shunt valve 1112.

In operation, when the flush dome 1106A is not pressed, the first and third valves 1130A, 1130C are open and fluid flows from the ventricle, through the first fluid lumen 1102A, through the flush dome 1106A (refilling the flush dome if applicable), through the shunt tap dome 1106B (refilling the shunt tap dome if applicable), and against the shunt valve 1112 which selectively opens to drain fluid through the drain port 1104 to control pressure in the ventricle. When the flush dome 1106A is pressed, the first and third valves 1130A, 1130C close and the second valve 1130B opens. Accordingly, a flushing cough of fluid flows out of the flush dome 1106A, through the second valve 1130B, and through the second fluid lumen 1102B to flush the upstream side of the system. The closed off third valve 1130C prevents the flush from flowing through the drain side of the system.

Figure 11B:
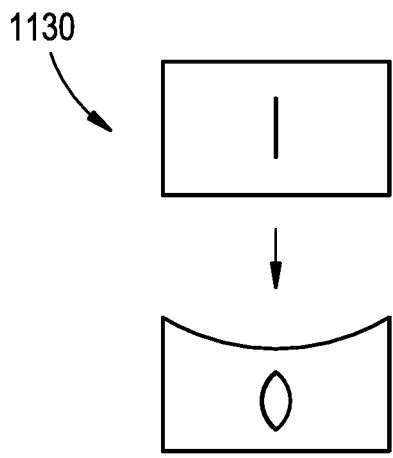
FIG. 11B is a schematic view of a slit valve that opens when pressed.

FIG. 11B illustrates an exemplary valve 1130 that can be used for the second valve 1130B of the flusher 1100. The valve 1130 can be defined by a slit formed in a wall of compressible material. In some embodiments, the wall can be formed from a biocompatible elastomer such as silicone. The slit can have a resting state that is closed as shown in the top part of FIG. 11B to prevent fluid flow therethrough. The slit can have a major axis that is parallel to a force applied to the wall when the flush dome 1106A is pressed. The force can be effective to deform the wall to cause the slit to open as shown in the bottom part of FIG. 11B to allow fluid to flow therethrough. The illustrated valve 1130 is thus normally closed, but opens when pressed.

Figure 11C:
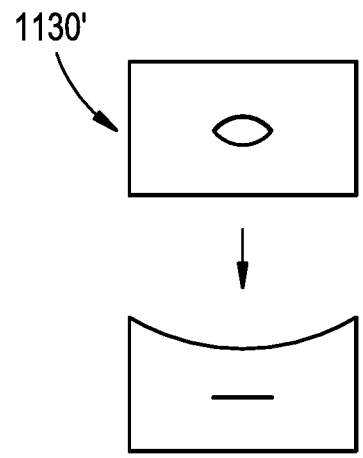
FIG. 11C is a schematic view of a slit valve that closes when pressed.

FIG. 11C illustrates an exemplary valve 1130' that can be used for the first and third valves 1130A, 1130C of the flusher 1100. The valve 1130' can be defined by a slit formed in a wall of compressible material. In some embodiments, the wall can be formed from a biocompatible elastomer such as silicone. The slit can have a resting state that is open as shown in the top part of FIG. 11C to allow fluid flow therethrough. The slit can have a major axis that is perpendicular to a force applied to the wall when the flush dome 1106A is pressed. The force can be effective to deform the wall to cause the slit to close as shown in the bottom part of FIG. 11C to block fluid flow therethrough. The illustrated valve 1130' is thus normally open, but closes when pressed.

FIGS. 12A-12B illustrate an exemplary flusher 1200 that includes an upstream or ventricle port 1202, a downstream or drain port 1204, a first retrograde flush dome or reservoir 1206A, and a second antegrade flush dome or reservoir 1206B. Either of the flush domes can also serve as a shunt tap. The upstream port 1202 is a "Y-entry" port in which first and second fluid lumens 1202A, 1202B of the upstream port are coupled to the first flush dome 1206A. The first and second fluid lumens 1202A, 1202B can merge into a single lumen in the housing of the flusher 1200 or in the ventricular catheter. The downstream port 1204 is a "Y-exit" port in which first and second fluid lumens 1204A, 1204B of the downstream port are coupled to the second flush dome 1206B. The first and second fluid lumens 1204A, 1204B can merge into a single lumen in the housing of the flusher 1200 or in the drain catheter.

A first valve 1230A controls fluid communication between the first fluid lumen 1202A and the first flush dome 1206A and is normally open, but closes when the first flush dome is pressed. A second valve 1230B controls fluid communication between the second fluid lumen 1202B and the first flush dome 1206A and is normally closed, but opens when the first flush dome is pressed. A third valve 1230C controls fluid communication between the first flush dome 1206A and the second flush dome 1206B and is normally open but closes when the first flush dome or the second flush dome is pressed. A fourth valve 1230D controls fluid communication between the second flush dome 1206B and the first fluid lumen 1204A and is normally closed but opens when the second flush dome is pressed. A shunt valve 1212 is disposed in-line with the second fluid lumen 1204B.

In operation, when neither flush dome 1206A, 1206B is pressed, the first and third valves 1230A, 1230C are open and fluid flows from the ventricle, through the first fluid lumen 1202A, through the first flush dome 1206A (refilling the dome if applicable), through the second flush dome 1206B (refilling the dome if applicable), and against the shunt valve 1212 which selectively opens to drain fluid through the drain port 1204 to control pressure in the ventricle. The fourth valve 1230D is closed to prevent passive flow through the first fluid lumen 1204A of the drain port 1204.

When the first flush dome 1206A is pressed, the first and third valves 1230A, 1230C close and the second valve 1230B opens. Accordingly, a flushing cough of fluid flows out of the first flush dome 1206A, through the second valve 1230B, and through the second fluid lumen 1202B of the upstream port 1202 to flush the upstream side of the system. The closed off third valve 1230C prevents the flush from flowing through the drain side of the system.

When the second flush dome 1206B is pressed, the third valve 1230C closes and the fourth valve 1230D opens. Accordingly, a flushing cough of fluid flows out of the second flush dome 1206B, through the fourth valve 1230D, and through the first fluid lumen 1204A of the downstream port 1204 to flush the downstream side of the system. The fourth valve 1230D allows the fluid flush to bypass the shunt valve 1212, which may or may not open during the flushing operation. The closed off third valve 1230C prevents the flush from flowing through the upstream side of the system.

The valves of the flusher 1200 can be slit valves of the type described above of any of a variety of other valve types. In some embodiments, the third valve 1230C can be omitted and the flush domes 1206A, 1206B can be integrated into a single dome. Accordingly, pressing the combined dome would flush both the upstream and the downstream sides of the system.

Figure 13:
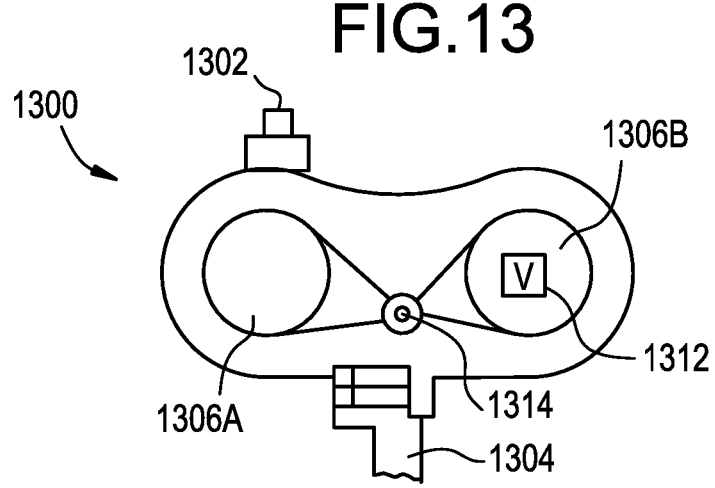
FIG. 13 is a schematic sectional top view of a flusher.

FIG. 13 illustrates an exemplary flusher 1300 that includes an upstream or ventricle port 1302, a downstream or drain port 1304, a flush dome or reservoir 1306A, and a shunt tap dome or reservoir 1306B having a shunt valve 1312 therein. The shunt tap dome 1306B can be pierceable and the flush dome 1306A can be non-pierceable. The flush dome 1306A and the shunt tap dome 1306B can be connected by a control valve 1314 configured to control fluid communication therebetween. The valve 1314 can be normally closed but can be configured to open when the flush dome 1306A is pressed. A slit valve of the type described above or any of a variety of other valve types can be used. In operation, when the flush dome 1306A is not pressed, the control valve 1314 is closed and fluid flows from the upstream port 1302 to the downstream port 1304, with the shunt valve 1312 controlling the flow to regulate the patient's ventricle pressure. When the flush dome 1306A is pressed, the control valve 1314 opens allowing a cough of fluid to flush the upstream and downstream sides of the system.

Figure 14A:
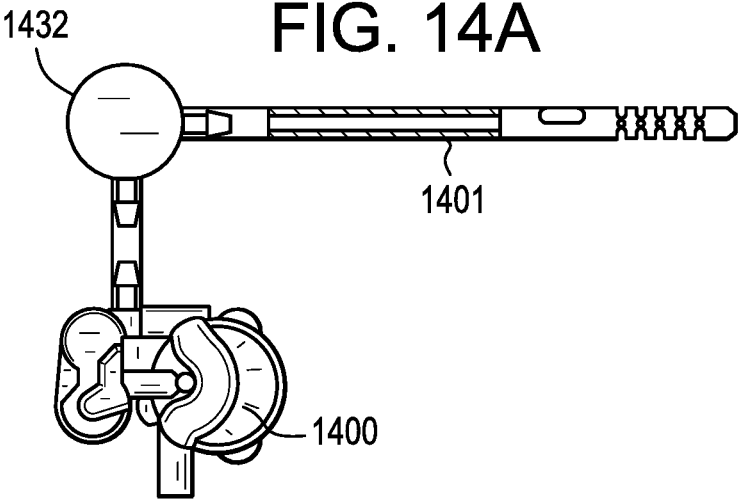
FIG. 14A is a schematic top view of a shunt system.
Figure 14B:
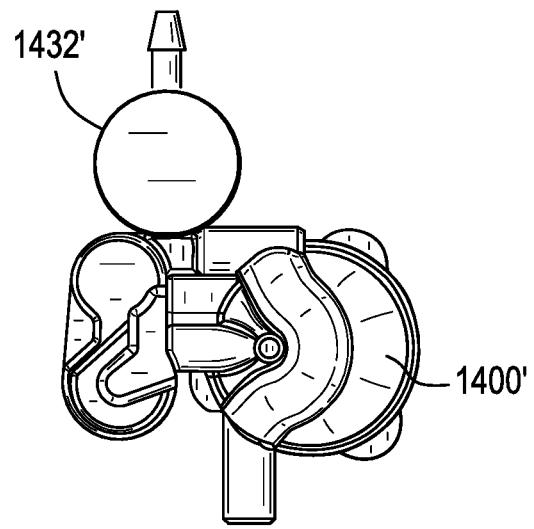
FIG. 14B is a schematic top view of a flusher.

A shunt tap dome or reservoir can be incorporated into any of the shunt systems described herein. For example, as shown in FIG. 14A, a Rickham-style reservoir or burr hole dome 1432 can be placed in-line between the flusher/shunt valve 1400 and the ventricular catheter 1401 and can be used for shunt tapping. As shown in FIG. 14B, the shunt tap dome 1432' can be directly mated to the flusher housing 1400' or can be formed integrally with the flusher housing.

Figure 15A:
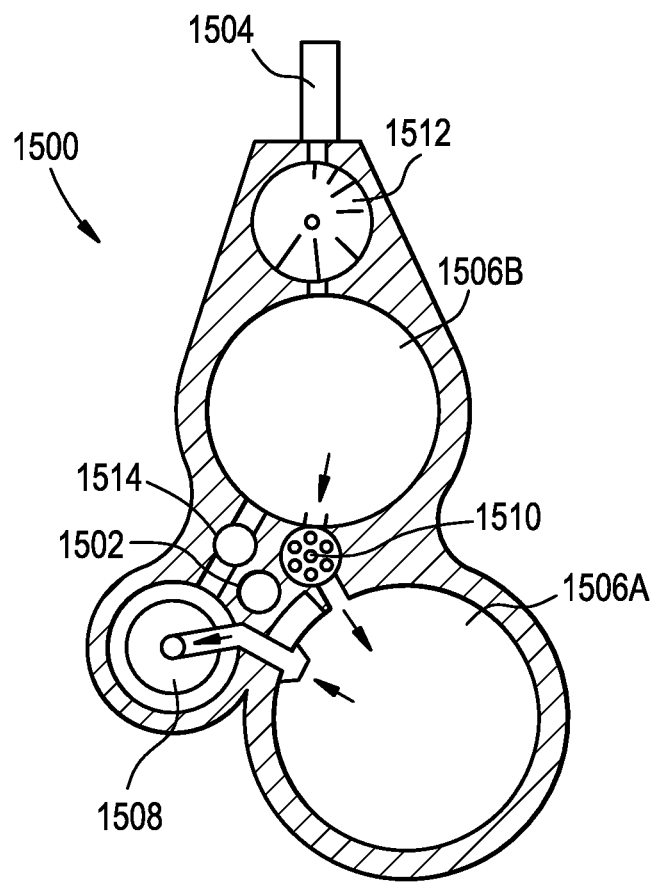
FIG. 15A is a schematic sectional top view of a flusher.
Figure 15B:
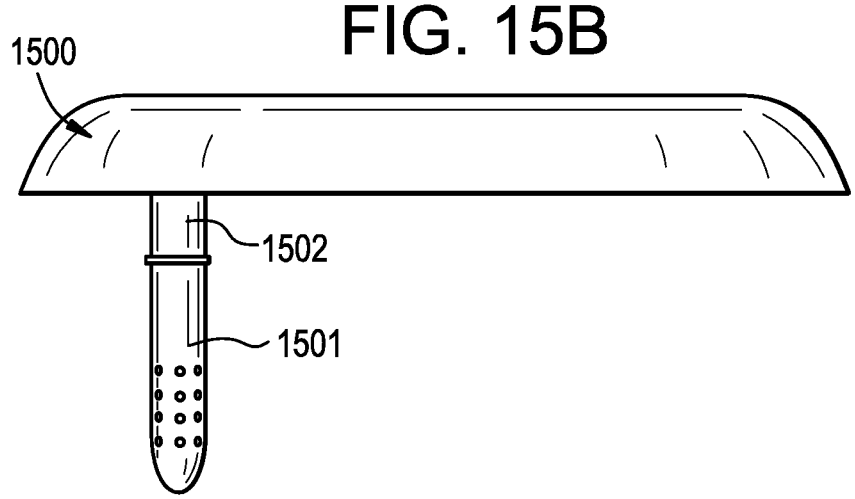
FIG. 15B is a side view of the flusher of FIG. 15A.

FIGS. 15A-15B illustrate an exemplary flusher 1500 that includes an upstream or ventricle port 1502, a downstream or drain port 1504, and a housing that includes a first flush dome or reservoir 1506A and a second shunt tap dome or reservoir 1506B. Either of the domes can serve as a shunt tap dome and can include a needle guard of the type described above. As shown in FIG. 15B, the ventricle port 1502 (and a ventricular catheter 1501 coupled thereto) can be oriented perpendicular to the flusher housing and to the drain port 1504. This can allow the flusher 1500 to be positioned over a burr hole in the patient's skull and to provide a simple 90-degree transition between the ventricular catheter 1501 descending down through the burr hole into the brain and the drain catheter extending along the skull surface beneath the skin.

The drain port 1504 is connected to the second dome 1506B by an adjustable shunt valve and/or occluder 1512. The occluder 1512 can be actuated, e.g., by manual finger pressure exerted thereon through the skin of the patient or by increasing the pressure threshold of the shunt valve to a very high setting, to cut off fluid communication between the second dome 1506B and the drain port 1504. When the occluder 1512 is in a resting state and no force is applied thereto, the drain port 1504 is in fluid communication with the second dome 1506B. Any of the shunt valves described herein can be used for the shunt valve/occluder 1512.

The second dome 1506B is connected to the first dome 1506A by a refill valve 1510. The refill valve 1510 allows one way flow of fluid from the second dome 1506B to the first dome 1506A to refill the first dome, e.g., after a flushing operation is performed. Any of the refill valves disclosed herein can be used for the refill valve 1510.

The first dome 1506A is in selective fluid communication with the ventricle port 1502 via a flush valve 1508. Any of the flush valves disclosed herein can be used for the flush valve 1508. When no force is applied to the flush dome 1506A, the flush valve 1508 is closed to cut off fluid communication between the flush dome 1506A and the ventricle port 1502. When the flush dome 1506A is pressed and a threshold opening pressure is reached, the flush valve 1508 opens to establish fluid communication between the flush dome 1506A and the ventricle port 1502.

A control valve 1514 controls fluid communication between the second dome 1506B and the ventricle port 1502. The control valve 1514 can be remotely or non-invasively actuated. For example, the control valve 1514 can be a magnetically-controlled valve.

The flusher 1500 can operate in a number of different modes.

In a restricted operating mode, the control valve 1514 is open and passive flow occurs when no force is applied to the domes 1506A, 1506B. In passive operation, fluid flows from the ventricle, through the ventricle port 1502, around the flush valve 1508, through the open control valve 1514, through the second dome 1506B and against the shunt valve/occluder 1512, which controls subsequent flow through the drain port 1504 to regulate ventricle pressure. The passive flow refills the second dome 1506B (if refilling is needed) and flows through the refill valve 1510 to refill the first dome 1506A (if refilling is needed).

If the first flush dome 1506A is depressed in the restricted operating mode, the flushing cough will follow the path of least resistance, either clearing obstructions from the primary flow ports of the ventricular catheter 1501 or flowing through the drain port 1504. Typically, both of these paths provide less resistance than required to open an auxiliary flow port of the ventricular catheter 1501. Accordingly, in the restricted operating mode, a user is prevented from opening the auxiliary flow port.

In an unrestricted operating mode, the control valve 1514 is closed. With the control valve 1514 closed, the drain side of the system is blocked and pressing the flush dome 1506A directs the cough of fluid through the ventricle side of the system only. Accordingly, the flush is effective to clear obstructions from a primary flow port of the ventricular catheter, open an auxiliary port of the ventricular catheter, or both. Thus, in the unrestricted operating mode, a user is permitted to open the auxiliary flow port.

When the control valve 1514 is closed, the second dome 1506B and the occluder 1512 can be used to increase the intensity of the flushing cough. By actuating the occluder 1512 to block flow through the drain port 1504 and pressing the second dome 1506B, the pressure in the first dome 1506A can be increased to pre-charge the first dome 1506A. As a result, the initial pressure in the flush dome 1506A is elevated and subsequently pressing the flush dome 1506A increases the pressure even more to generate a high intensity cough of fluid. The user can thus apply a low level flush by pressing the first dome 1506A without pressing the second dome 1506B or closing the occluder 1512. The user can apply a high level flush by closing the occluder 1512 and pressing the second dome 1506B before pressing the first dome 1506A.

When the control valve 1514 is closed and a flushing operating is performed, the closed control valve prevents the flush dome 1506A from refilling from the ventricle side of the system. The flush dome 1506A can thus remain empty after the flushing operation. Typically, a user can discern that the flush dome 1506A is empty by palpating the dome through the patient's skin, and therefore this mode of operation can give the user confidence that a flushing operation was performed when an empty dome is observed. In some embodiments, subsequent flushing operations cannot be performed until the control valve 1514 is opened to allow the dome 1506A to refill. This can help the user ensure that only a single flushing operation is performed at a time, and make it easier to keep track of the number of flushing operations that are performed.

FIG. 15C illustrates a flusher 1500' that is similar to the flusher 1500 described above except that it includes a pinch tube 1534 disposed over the first flush dome 1506A that provides a fluid communication path between the ventricle port 1502 and the second dome 1506B. The pinch tube 1534 can allow passive flow to occur through the flusher even when the control valve 1514 is closed. The pinch tube 1534 collapses to block the drain side of the system when the first dome 1506A is depressed, such that a flushing operation performed while the control valve 1514 is closed is still effective to flow only through the ventricle side of the system.

In some embodiments, a flusher can include a dual flush function. The flusher can be configured to emit a first flush having a pressure P1 and a second flush having a pressure P2 that is greater than P1. Alternatively, or in addition, the first flush can have a volume V1 and the second flush can have a volume V2 that is greater than V1. The first flush can be sufficient to clear debris from a primary flow port of a catheter, but insufficient to open an auxiliary flow port of the catheter. The second flush can be sufficient to open an auxiliary flow port through the catheter. The system can include features to limit use of the second flush, for example, to allow a patient to perform the first flush but to limit use of the second flush to a clinician. In one example, the first flush can have a volume of 0.25 mL and a pressure of 10 psi and the second flush can have a volume of 0.5 mL and a pressure of 30 psi.

Figure 16A:
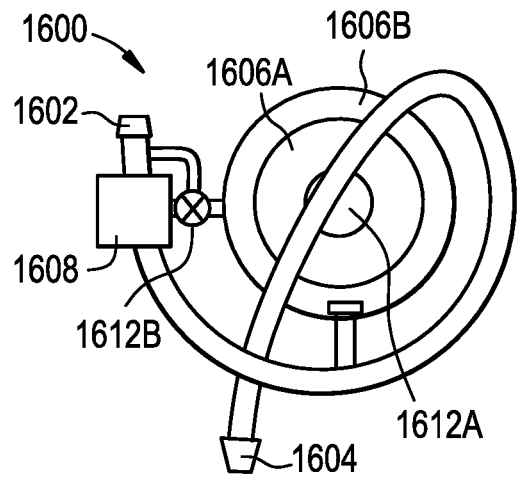
FIG. 16A is a schematic sectional top view of a flusher.
Figure 16B:
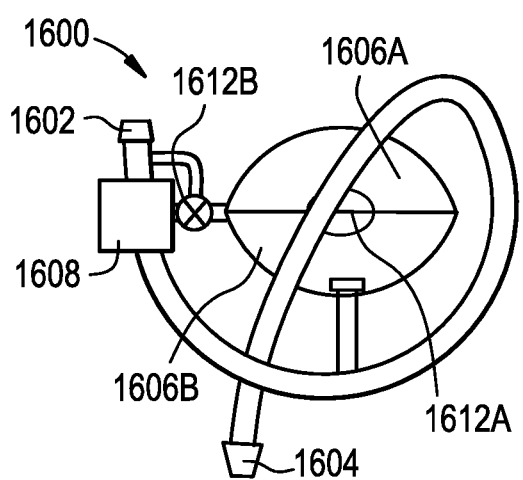
FIG. 16B is a schematic sectional top view of a flusher.
Figure 16C:
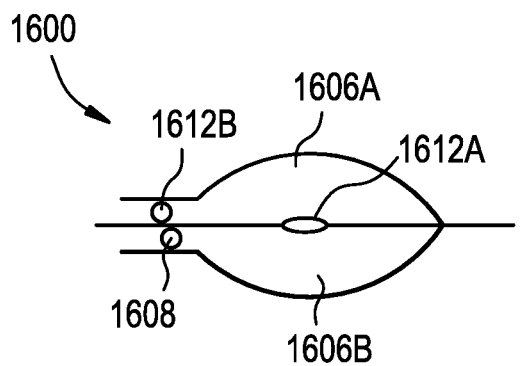
FIG. 16C is a schematic sectional side view of a flusher.

FIGS. 16A-16D illustrate a flusher with a dual flush function. The flusher 1600 includes a first flush dome 1606A and a second flush dome 1606B separated by a first control valve 1612A. The flush domes 1606A, 1606B can be stacked vertically, e.g., as shown in FIG. 16A, or can be positioned side-by-side, e.g., as shown in FIG. 16B. The first flush dome 1606A can be connected to the ventricle port 1602 by a second control valve 1612B. The second flush dome 1606B can be connected to the ventricle port 1602 by a flush valve 1608. The flusher 1600 can include a pinch tube as shown to block the drain port 1604 when the flush domes 1606A, 1606B are pressed. The flusher 1600 can be configured such that pressing on a top surface of the flusher at a single contiguous contact area is effective to collapse the pinch tube and both flush domes 1606A, 1606B.

Figure 16D:
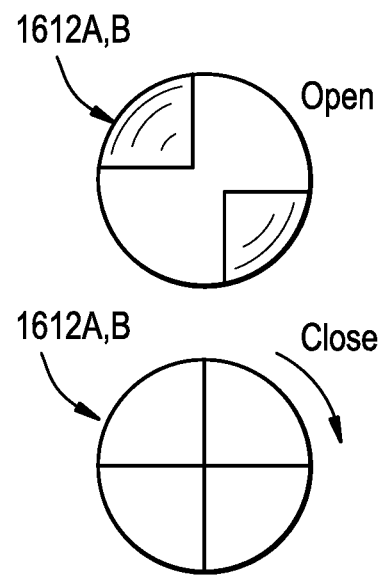
FIG. 16D is a schematic view of a valve.

The first and second control valves 1612A, 1612B can be opened or closed non-invasively. FIG. 16D illustrates an exemplary valve that includes a rotatable magnetic disc. Application of an external magnetic field to the valve can rotate the disc to open or close the valve. Various other non-invasively adjustable valves can be used instead or in addition.

The flusher 1600 is operable in a restricted operating mode in which the first control valve 1612A is closed and the second control valve 1612B is open. In the restricted operating mode, pressing the flusher 1600 collapses the first dome 1606A. Fluid in the first flush dome 1606A escapes through the open second control valve 1612B to the ventricle port 1602 without generating a high pressure cough. Pressing the flusher 1600 also collapses the second dome 1606B, eventually opening the flush valve 1608 to emit a high pressure cough of fluid through the ventricle port 1602. Because the first control valve 1612A is closed, the fluid of the first flush dome 1606A is not included in the cough of fluid and does not contribute to the pressure or volume of the flushing operation. The flushing operation is therefore a first flush of the type described above (e.g., a flush having reduced pressure and/or volume).

The flusher 1600 is also operable in an unrestricted operating mode in which the first control valve 1612A is open and the second control valve 1612B is closed. In the unrestricted operating mode, pressing the flusher 1600 collapses the first dome 1606A. Fluid in the first flush dome 1606A cannot escape through the closed second control valve 1612B and instead flows through the open first control valve 1612A to combine with the fluid in the second flush dome 1606B. Pressing the flusher 1600 also collapses the second dome 1606B, eventually opening the flush valve 1608 to emit a high-pressure cough of fluid through the ventricle port 1602. The resulting cough of fluid includes the fluid from both the first and second flush domes 1606A, 1606B. The flushing operation is therefore a second flush of the type described above (e.g., a flush having increased pressure and/or volume).

FIGS. 17A-17B illustrate an exemplary catheter 1701 that can be used in the shunt systems described herein. The catheter 1701 includes one or more primary flow ports 1703 and one or more auxiliary flow ports 1705. The auxiliary flow port 1705 can be initially closed or blocked and selectively opened to provide an alternative path for fluid to flow through the catheter 1701, e.g., when the primary flow port 1703 becomes clogged. The auxiliary flow port 1705 can be configured to open in response to a non-invasive, extracorporeal input applied thereto. For example, a periphery of the auxiliary flow port 1705 can be defined by a shape memory frame 1707 embedded in or coupled to the sidewall of the catheter. The shape memory frame 1707 can be initially retained as shown in FIG. 17A to hold the auxiliary flow port 1705 closed. The shape memory frame 1707 can be released to allow the shape memory frame to return to a resting state in which the auxiliary flow port 1705 is open, as shown in FIG. 17B. The shape memory frame 1707 can be released by applying an electrical signal to a metallic clip holding the frame closed to melt the clip and release the frame. The shape memory frame 1707 can be released by applying a magnetic field to a metallic or magnetic clip holding the frame closed to move the clip and release the frame. The shape memory frame 1707 can be formed from Nitinol or other materials with resilient or shape memory properties. The frame 1707 can completely surround the auxiliary flow port 1705, or can be formed as one or more discrete leaf springs positioned adjacent to the auxiliary flow port. In some instances, only a qualified clinician is able to apply the input to open the auxiliary flow port 1705. Accordingly, a patient can flush the catheter 1701 as needed without opening the auxiliary flow port 1705.

FIGS. 18A-18B illustrate an exemplary flusher 1800 and extracorporeal flush device 1836 that can be used in the shunt systems described herein. The flusher 1800 includes a first flush dome 1806A and a second flush dome 1806B separated by a control valve 1812 (e.g., a magnetically-actuated control valve). The flush device 1836 has a skin-contacting surface with a recess 1838 formed therein that defines a substantial negative of the flusher 1800, except that the recess includes a projection 1840 configured to bear against and collapse the second flush dome 1806B when the flush device is pressed down over the implanted flusher 1800. The geometry of the projection 1840 can be selected or calibrated to apply the desired force to the second flush dome 1806B or to displace the desired volume of fluid from the second flush dome 1806B. The first flush dome 1806A can have a smaller volume and/or can be coupled to a flush valve having a lower opening pressure. The second flush dome 1806B can have a greater volume and/or be coupled to a flush valve having a greater opening pressure. Accordingly, in some embodiments, actuating the first flush dome 1806A would only be effective to clear a primary flow port of the catheter and would not be effective to open an auxiliary flow port of the catheter, whereas actuating the second flush dome 1806B would be sufficient to open the auxiliary flow port.

The flusher 1800 is operable in a restricted mode in which the control valve 1812 is closed such that only the first flush dome 1806A can be actuated to emit a flushing cough through the ventricle port 1802 of the flusher. The closed control valve 1812 prevents a flushing cough from exiting the second flush dome 1806B if the second flush dome is pressed while in the restricted mode.

The flusher 1800 is operable in an unrestricted mode in which the control valve 1812 is open. In the unrestricted mode, the second flush dome 1806B can be actuated to emit a flushing cough through the ventricle port 1802 of the flusher. As noted above, the cough emitted by the second flush dome 1806B can be greater than that of the first flush dome 1806A, such that the cough is sufficient to open an auxiliary flow port of the ventricular catheter. In use, the flusher 1800 would normally be in the restricted mode. When it is desired to open an auxiliary flow path, a clinician could apply an external magnetic field or other input to switch the flusher 1800 to the unrestricted mode and then place the flush device 1836 over the implanted flusher to emit a calibrated flush that opens the auxiliary flow path. It will be appreciated that the flusher 1800 can be used without the flush device 1836, e.g., using simple manual finger pressure. It will further be appreciated that a flush device such as the illustrated flush device 1836 can be used with any of the flushers disclosed herein.

Figure 19:
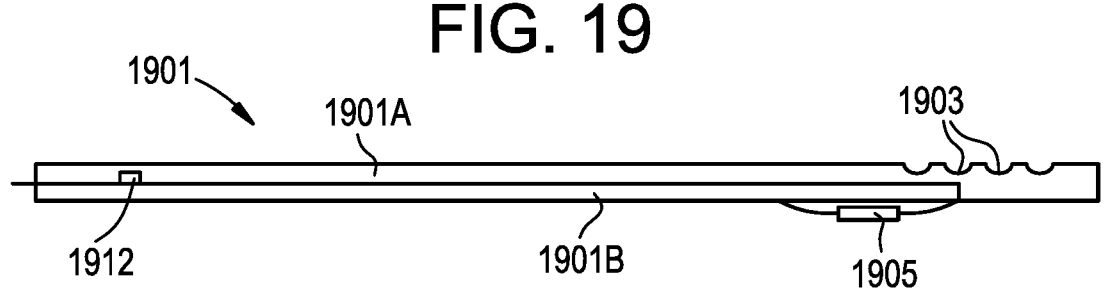
FIG. 19 is a sectional side view of a catheter.

FIG. 19 illustrates an exemplary ventricular catheter 1901 that can be used in the shunt systems described herein. The catheter 1901 includes one or more primary flow ports 1903 and one or more auxiliary flow ports 1905. The auxiliary flow port 1905 can be initially closed or blocked and selectively opened to provide an alternative path for fluid to flow through the catheter 1901, e.g., when the primary flow port 1903 becomes clogged. The catheter 1901 can include first and second lumens 1901A, 1901B, the first lumen being in communication with the primary flow port 1903 and the second lumen being in communication with the auxiliary flow port 1905. The second lumen 1901B can be sealed off from the first lumen 1901A by a one-way pressure-dependent valve 1912. In use, a flushing cough delivered to the catheter 1901 below the opening pressure threshold of the valve 1912 would be directed only towards the primary flow port 1903. A flushing cough delivered to the catheter 1901 at or above the opening pressure threshold of the valve 1912 would cause the valve to open and direct the flushing cough to the auxiliary flow port 1905 to open the auxiliary flow port. The catheter 1901 can be used with flushers of the type described herein having an adjustable cough pressure. For example, the flusher of FIGS. 2A-2J can be used with the catheter 1901. The flush valve can be adjusted (e.g., using an extracorporeal adjustment input such as a magnetic force) to a relatively low opening pressure to place the system in a restricted mode in which flushing coughs emitted by the flusher 200 travel only through the first lumen 1901A of the catheter 1901. The flush valve can be adjusted to a relatively higher opening pressure to place the system in an unrestricted mode in which flushing coughs emitted by the flusher 200 have sufficient pressure to open the valve 1912 of the catheter 1901 and travel through the second fluid lumen 1901B to the auxiliary flow port 1905. As another example, any of the "dual-flush" flushers disclosed herein can be used with the catheter 1901.

Figure 20:
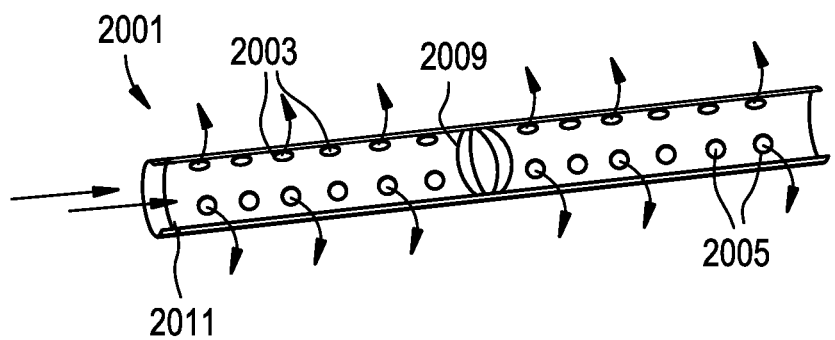
FIG. 20 is a sectional side view of a catheter.

FIG. 20 illustrates an exemplary catheter 2001 that can be used in the shunt systems described herein. The catheter 2001 includes one or more primary flow ports 2003 and one or more auxiliary flow ports 2005. The auxiliary flow port 2005 can be initially closed or blocked and selectively opened to provide an alternative path for fluid to flow through the catheter 2001, e.g., when the primary flow port 2003 becomes clogged. The auxiliary flow port can be covered by a membrane defined between an interior of the catheter and an exterior of the catheter. Alternatively, as shown, a membrane 2009 can partition off a distal portion of the catheter 2001 with auxiliary flow ports 2005 formed therein. When the membrane 2009 is ruptured, fluid can flow through the catheter 2001 via the distal auxiliary flow ports 2005. The catheter 2001 can include a connector 2011 at a proximal end of the catheter for selectively coupling the catheter to various flushers. The catheter 2001 can be provided as a kit with a first flusher (e.g., a patient flusher) and a second flusher (e.g., a clinician flusher). The second flusher can be configured to deliver a flushing cough with a pressure and/or a volume that is greater than that of the first flusher. The pressure and/or volume of the flush emitted by the first flusher can be insufficient to open the auxiliary flow port. Accordingly, when the first flusher is used with the catheter 2001, only the primary flow ports are cleared of obstructions and the auxiliary flow port cannot be opened. When the second flusher is used with the catheter 2001, the pressure and/or volume can be sufficient to open the auxiliary flow port.

Figure 21:
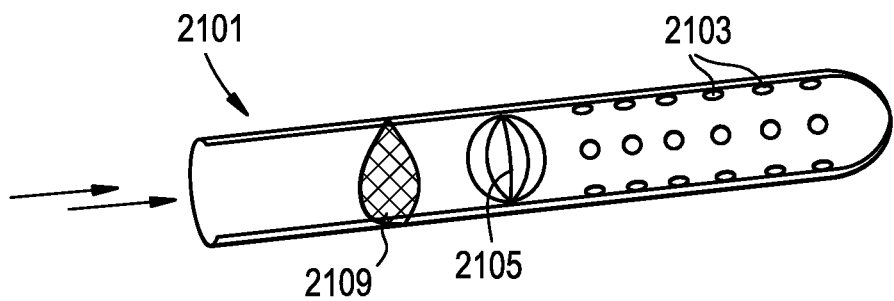
FIG. 21 is a sectional side view of a catheter.

FIG. 21 illustrates an exemplary catheter 2101 that can be used in the shunt systems described herein. The catheter 2101 includes one or more primary flow ports 2103 and one or more auxiliary flow ports 2105. The auxiliary flow port 2105 can be initially closed or blocked and selectively opened to provide an alternative path for fluid to flow through the catheter 2101, e.g., when the primary flow port 2103 becomes clogged. The catheter 2101 can include a partition 2109 with an adjustable aperture size. The aperture size can be adjusted remotely, e.g., using an extracorporeal control device. For example, an external magnetic field or an electrical signal can be applied to adjust the size of the aperture. In some embodiments, the partition 2109 can be an electronically-controlled iris. The partition 2109 can be formed from various materials, including electroactive polymers configured to change shape in response to an electrical signal applied thereto. The catheter 2101 is operable in a restricted mode in which the aperture is closed to seal off open auxiliary flow ports of the catheter disposed distal to the partition 2109, or in which the aperture is open to a relatively small size to limit the volume and/or pressure of a flushing cough passing therethrough such that the force is insufficient to open closed auxiliary flow ports 2105 distal to the partition. The catheter 2101 is operable in an unrestricted mode in which the aperture is open to allow open auxiliary flow ports of the catheter disposed distal to the partition 2109 to be used, or to allow sufficient flushing volume or pressure to pass through the aperture to open closed auxiliary flow ports 2105 distal to the partition.

Figure 22:
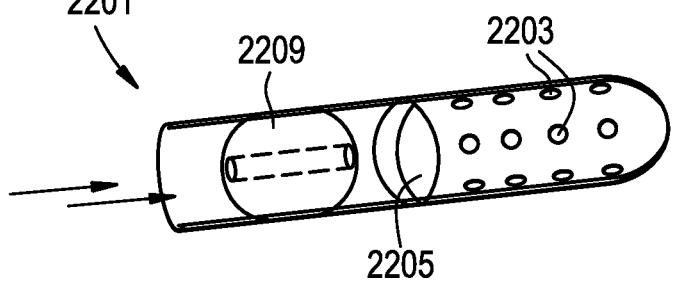
FIG. 22 is a sectional side view of a catheter.

FIG. 22 illustrates an exemplary catheter 2201 that can be used in the shunt systems described herein. The catheter 2201 is similar to the catheter 2101 described above, except that the catheter 2201 includes a pneumatically actuated partition 2209. The partition 2209 can include a balloon with an inflation lumen coupled thereto configured to supply or remove an inflation medium from the balloon. The balloon can include a flow path extending therethrough. In use, the balloon can be inflated to open the otherwise closed flow path. In an alternative arrangement, the balloon can be deflated to open the otherwise closed flow path, or to form a flow path around the balloon through which fluid can flow.

FIG. 23 illustrates an exemplary method of opening an auxiliary flow port 2305 in a catheter 2301. As shown, a syringe 2336 or other device can be used to pierce or puncture a flush dome 2306 of an implanted flusher 2300, e.g., a shunt tap dome of the flusher. The syringe 2336 can be used to aspirate fluid from the shunt system, creating a negative pressure in the system sufficient to open a membrane of an auxiliary flow port 2305 in the catheter 2301. The syringe 2336 can also be used to inject fluid into the shunt system, creating a positive pressure in the system sufficient to open a membrane of an auxiliary flow port 2305 in the catheter 2301.

FIG. 24 illustrates an exemplary flusher 2400 that can be used in the shunt systems herein. The flusher 2400 includes a flush dome 2406A and a negative pressure reservoir 2406B. The negative pressure reservoir 2406B can be disposed within the flush dome 2406A as shown, or elsewhere within the flusher 2400. The negative pressure reservoir 2406B can be vacuum sealed during manufacturing such that a negative pressure is maintained in the reservoir 2406B. In use, the reservoir 2406B can be selectively activated, e.g., by placing the reservoir 2406B in fluid communication with the flush dome 2406A, to expose a catheter 2401 coupled to the flusher 2400 to a negative pressure sufficient to open a membrane of an auxiliary flow port 2405 in the catheter. The reservoir 2406B can be activated in various ways, such as by piercing the reservoir with a needle, applying a magnetic field to open a valve that seals the reservoir, etc.

FIG. 25 illustrates an exemplary flusher 2500 and catheter 2501 that can be used in the shunt systems described herein. The catheter 2501 includes one or more primary flow ports 2503 and one or more auxiliary flow ports 2505. The auxiliary flow port 2505 can be initially closed or blocked and selectively opened to provide an alternative path for fluid to flow through the catheter 2501, e.g., when the primary flow port 2503 becomes clogged. The catheter 2501 can include first and second lumens 2501A, 2501B, the first lumen being in communication with the primary flow port 2503 and the second lumen being in communication with the auxiliary flow port 2505. The second lumen 2501B can be sealed off from the first lumen 2501A by a magnetically-actuated flap or valve 2512. In use, a flushing cough delivered to the catheter 2501, e.g., using a flusher 2500 of the type described herein) is normally directed only towards the primary flow port 2503. When a magnetic field is applied to the flap or valve 2512, e.g., using an extracorporeal device, the valve opens to direct the flushing cough to the auxiliary flow port 2505 to open the auxiliary flow port. The valve 2512 can be disposed in the catheter 2501 as shown to change the fluid path through the catheter, or can be disposed in the flusher 2500 to change the fluid path through the catheter.

FIG. 26 illustrates an exemplary flusher 2600 and catheter 2601 that can be used in the shunt systems described herein. The catheter 2601 includes one or more primary flow ports 2603 and one or more auxiliary flow ports 2605. The auxiliary flow port 2605 can be initially closed or blocked and selectively opened to provide an alternative path for fluid to flow through the catheter 2601, e.g., when the primary flow port 2603 becomes clogged. The catheter 2601 can include first and second lumens 2601A, 2601B, the first lumen being in communication with the primary flow port 2603 and the second lumen being in communication with the auxiliary flow port 2605. The second lumen 2601B can be sealed off from the first lumen 2601A. The first lumen 2601A is in fluid communication with a flush dome 2606A of the flusher 2600. Accordingly, actuation of the flush dome 2606A, e.g., by a patient, can be effective to clear obstructions from the primary flow port 2603. The second lumen 2601B is in fluid communication with a port 2606B of the flusher 2600, which can be formed, for example, as a pierceable membrane. An external flusher or syringe can be coupled to the port 2606B to direct negative vacuum pressure or positive flushing pressure through the second lumen 2601B to open an auxiliary flow port 2605. Typically, only a qualified clinician would couple an external flusher to the port 2606B and be able to open the auxiliary flow port 2605. Flushing the second lumen 2601B can also be effective to open a recirculation flow path 2613 between the first and second lumens 2601A, 2601B. This can allow fluid to be shunted through the auxiliary flow port 2605 and through the flusher 2600 after the flushing operation is performed. The second lumen 2601B of the catheter can be vacuum sealed prior to use to limit or prevent air from entering the system.

Figure 27A:
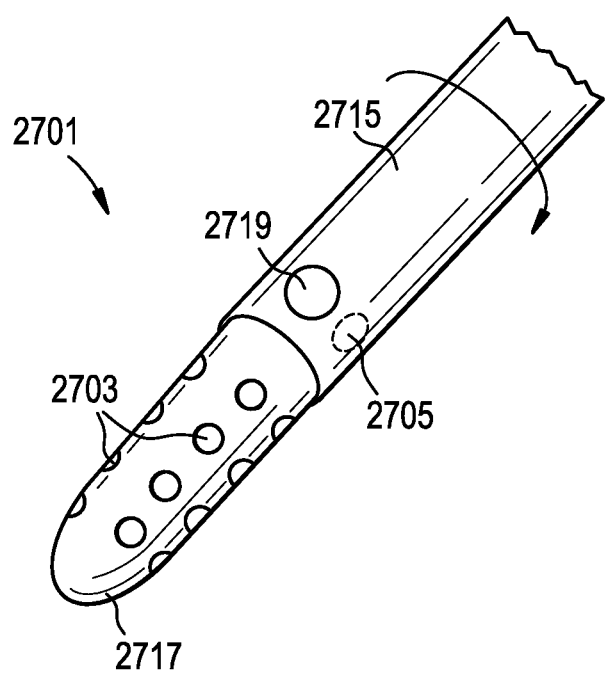
FIG. 27A is a perspective view of a catheter.

FIG. 27A illustrates an exemplary catheter 2701 that can be used in the shunt systems described herein. The catheter 2701 includes one or more primary flow ports 2703 and one or more auxiliary flow ports 2705. The auxiliary flow port 2705 can be initially closed or blocked and selectively opened to provide an alternative path for fluid to flow through the catheter 2701, e.g., when the primary flow port 2703 becomes clogged. The auxiliary flow port 2705 can be initially blocked by an inner or outer sheath 2715 coaxially disposed within or over the catheter body 2717. The sheath 2715 can include one or more openings 2719 formed therein configured to be selectively aligned with the auxiliary flow port 2705 of the catheter. When the opening 2719 of the sheath 2715 is not aligned with the auxiliary flow port 2705, a flushing operation delivered to the catheter is only effective to clear the primary flow port 2703, and does not reach the auxiliary flow port. When the opening 2719 of the sheath 2715 is aligned with the auxiliary flow port 2705, a flushing operation delivered to the catheter reaches the auxiliary flow port and can open the port.

Figure 27B:
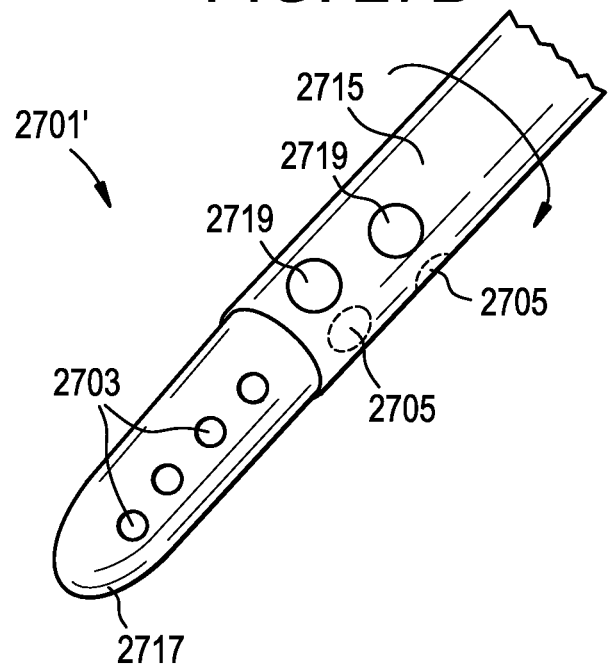
FIG. 27B is a perspective view of a catheter.

The opening 2719 of the sheath 2715 can be aligned with the auxiliary flow port 2705 by rotating the sheath relative to the catheter body 2717 about a longitudinal axis thereof as shown in FIGS. 27A-27B. The sheath 2715 can include multiple openings 2719 spaced along the length of the sheath and staggered about the circumference of the sheath, as shown in the catheter 2701' of FIG. 27B. The catheter body 2717 can include auxiliary flow ports 2705 formed in a corresponding pattern, but staggered by a greater distance about the circumference. This can allow incremental rotation of the sheath 2715 to open additional auxiliary flow ports 2705, allowing the system to be used multiple times to form auxiliary flow paths. For example, rotating the sheath to a first degree can align a first opening of the sheath with a first auxiliary flow port without opening a second auxiliary flow port. Rotating the sheath to a second degree that is greater than the first degree can align a second opening of the sheath with the second auxiliary flow port without opening a third auxiliary flow port, and so on.

As shown in FIGS. 28A-28B, a catheter 2801 can include a sheath 2815 that includes a single, longitudinally-elongated opening 2819 configured to be selectively aligned with one or more of a plurality of auxiliary flow ports 2805 formed in the catheter. The auxiliary flow ports 2805 are spaced along the length of the catheter 2801 and staggered about the circumference of the catheter. The catheter 2801 operates in a manner similar to the catheter 2701 described above.

Rotation of the sheath 2815 relative to the catheter body 2817 can be controlled in various ways. For example, as shown in FIG. 28B, a proximal end of the catheter body 2817 can be coupled to a magnetically-actuated disc 2821 configured to rotate in response to an externally-applied magnetic field. The disc 2821 can rotate relative to a base plate 2823 to which the sheath 2815 is coupled. Accordingly, rotation of the disc 2821 relative to the base plate 2823 is effective to rotate the sheath 2815 relative to the catheter body 2817. The disc 2821 can be configured to lock into one of a plurality of discrete rotational positions. For example, a magnetic field can be applied to lift the disc, rotate it, and then drop it back down into the next successive rotational position. The disc 2821 can include a locking pin projecting therefrom configured to be received in any of a plurality of discrete recesses disposed about a circumference of the base plate 2823. The disc 2821 can be integrated into a burr hole anchor, a Rickham-style reservoir, or a flusher of the type described herein.

As another example, the sheath can be hydraulically-actuated such that fluid pressure, e.g., supplied from an external syringe or from a flusher, acts on the sheath to rotate the sheath relative to the catheter. As another example, the catheter can be used with dual-pressure or dual-volume flushers of the type described herein. Low-pressure or low-volume flushes emitted by such devices can be insufficient to rotate the sheath and therefore would not open an additional auxiliary flow port. High-pressure or high-volume flushes emitted by such devices can be sufficient to rotate the sheath and therefore open an additional auxiliary flow port. As another example, the catheter can be used with a single-volume or single-pressure flusher. When a flushing operation is performed that is sufficient to clear the primary flow port, the pressure in the system remains below a threshold pressure required to rotate the sheath. When the flushing operation is insufficient to clear the primary flow port, the pressure in the system can increase to a level sufficient to cause the sheath to rotate and thereby open an auxiliary flow port. As another example, the sheath can be formed from an electroactive polymer and an electrical signal can be applied thereto to move the sheath or adjust the shape of the sheath. As another example, a stepper motor or other mechanical element can be used to rotationally index the sheath.

FIG. 29 illustrates a catheter 2901 that operates in a manner similar to the catheters 2701, 2801 described above, except that the sheath 2915 translates longitudinally relative to the catheter body 2917 instead of or in addition to rotating relative to the catheter body. The catheter body 2917 includes a plurality of auxiliary flow ports 2905 spaced along a length of the catheter. The sheath 2915 includes an opening 2919 configured to be aligned with each of the auxiliary flow ports 2905 as the sheath translates axially along the catheter body 2917. The sheath 2915 can be initially placed in a distal-most position to align the opening 2919 with a distal auxiliary flow port 2905 of the catheter. When it is desired to open a different auxiliary flow port, the sheath 2915 can be retracted proximally to align the opening 2919 with said flow port. In other embodiments, the sheath 2915 can operate in the opposite direction, e.g., sliding the sheath distally relative to the catheter body 2917 to open successive auxiliary flow ports 2905.

Longitudinal translation of the sheath 2915 can be controlled in various ways. For example, the proximal end of the sheath 2915 can be coupled to a disc having a stepped or tapered surface such that rotation of the disc against a base plate, e.g., via an external magnetic field or via fluid pressure from a syringe or flusher, adjusts a longitudinal position of the sheath 2915 relative to the base plate and relative to the catheter body 2917. The sheath 2915 can be rotatably coupled to the disc such that rotation of the disc does not cause the sheath to rotate. As noted above, the sheath 2915 can be disposed within the catheter body 2917 or can be disposed about an exterior surface of the catheter body. As another example, the sheath 2915 can be formed from an electroactive polymer and an electrical signal can be applied thereto to move the sheath or adjust the shape of the sheath. As another example, a stepper motor or other mechanical element can be used to longitudinally index the sheath 2915.

Figure 30:
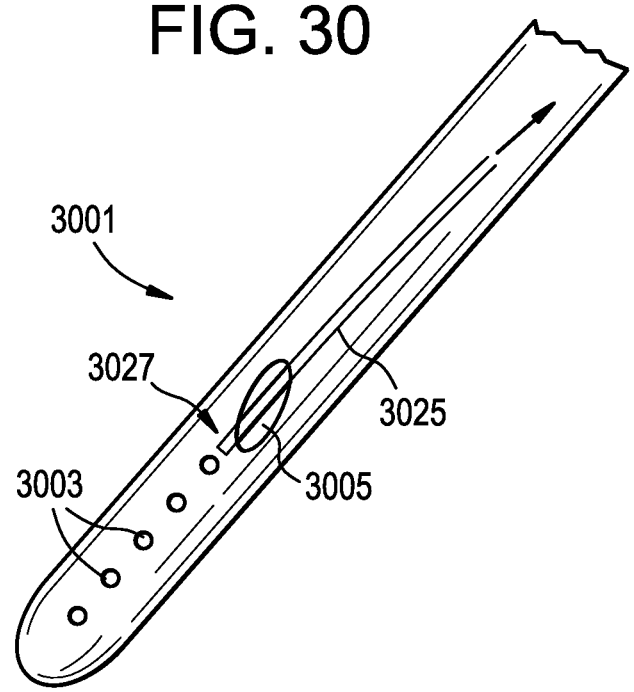
FIG. 30 is a sectional perspective view of a catheter.

FIG. 30 illustrates an exemplary catheter 3001 that can be used in the shunt systems described herein. The catheter 3001 includes one or more primary flow ports 3003 and one or more auxiliary flow ports 3005. The auxiliary flow port 3005 can be initially closed or blocked and selectively opened to provide an alternative path for fluid to flow through the catheter 3001, e.g., when the primary flow port 3003 becomes clogged. A thin wire 3025 is initially disposed across the auxiliary flow port 3005. The wire 3025 can act as a strut to reinforce the membrane of the auxiliary flow port 3005 to prevent it from being opened. Alternatively, or in addition, the wire 3025 can cover a portion of the auxiliary flow port 3005 to limit the surface area of the membrane that is exposed to a flushing operation to prevent the auxiliary flow port from opening. A distal end 3027 of the wire 3025 can be atraumatic or sealed within the catheter to prevent patient injury. In use, the wire 3025 can be severed or retracted proximally to open the auxiliary flow port 3005 or to allow the auxiliary flow port to be opened by a flushing operation. The wire 3025 can also be used to control the threshold pressure required to open the membrane, e.g., by selecting a wire having a thickness or material properties calibrated to the desired opening pressure. The wire can be severed or retracted in various ways. For example, an electric current can be applied to the wire to sever the wire. As another example, an external magnetic field can be applied to the wire to withdraw the wire proximally. As another example, a proximal end of the wire can be disposed around a spool, e.g., formed in a flusher or burr hole cap, that can be rotated by a magnetic field or by fluid pressure to wind up the wire and pull the wire proximally.

Figure 31:
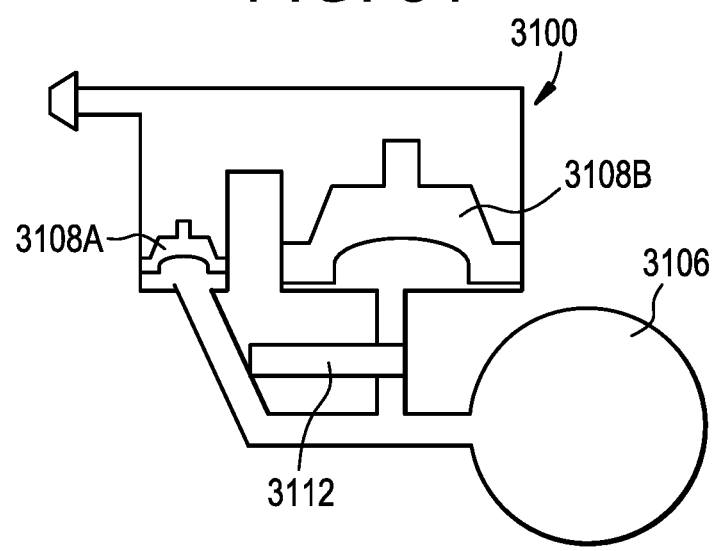
FIG. 31 is a schematic sectional top view of a flusher.

FIG. 31 illustrates an exemplary flusher 3100 that can be used in the shunt systems described herein. The flusher includes a first flush valve 3108A and a second flush valve 3108B that have different opening pressures. For example, the first flush valve 3108A can be configured to open at a lower threshold pressure than the second flush valve 3108B. The flush dome 3106 of the flusher 3100 can be selectively coupled to one of the two flush valves 3108A, 3108B by a diverter 3112. The diverter 3112 can be actuated to connect the flush dome 3106 to the first flush valve 3108A, e.g., to place the flusher in a restricted mode in which flushing pressure is insufficient to open an auxiliary flow port. The diverter 3112 can be actuated to disconnect the flush dome 3106 from the first flush valve 3108A and instead connect the flush dome 3106 to the second flush valve 3108B, e.g., to place the flusher in an unrestricted mode in which flushing pressure is sufficient to open an auxiliary flow port. Typically, the diverter 3112 would be positioned in the restricted mode for patient use and then switched to the unrestricted mode when a clinician or other qualified operator wishes to open an auxiliary flow port. The diverter 3112 can be controlled in various ways. For example, the diverter can be a magnetically or electronically-actuated valve. The diverter can be actuated non-invasively, e.g., using an extracorporeal controller.

Figure 32:
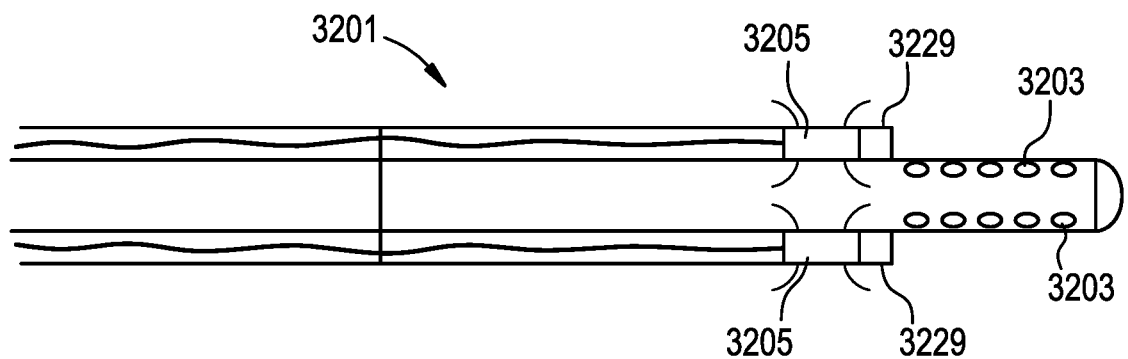
FIG. 32 is a sectional side view of catheter.

FIG. 32 illustrates an exemplary catheter 3201 that can be used in the shunt systems described herein. The catheter 3201 includes one or more primary flow ports 3203 and one or more auxiliary flow ports 3205. The auxiliary flow port 3205 can be initially closed or blocked and selectively opened to provide an alternative path for fluid to flow through the catheter 3201, e.g., when the primary flow port 3203 becomes clogged. The catheter 3201 can include one or more sensors 3229 configured to detect when an auxiliary flow port 3205 is opened and generate a signal in response thereto that can provide feedback to a user as to whether the flow port was opened. Exemplary sensors 3229 include acoustic sensors configured to detect sound waves emitted by a membrane disposed over the auxiliary flow port 3205 when the membrane ruptures. The sensors 3229 can be disposed adjacent to the auxiliary flow ports 3205 as shown, or can be positioned at various other locations along the catheter 3201.

Figure 33:
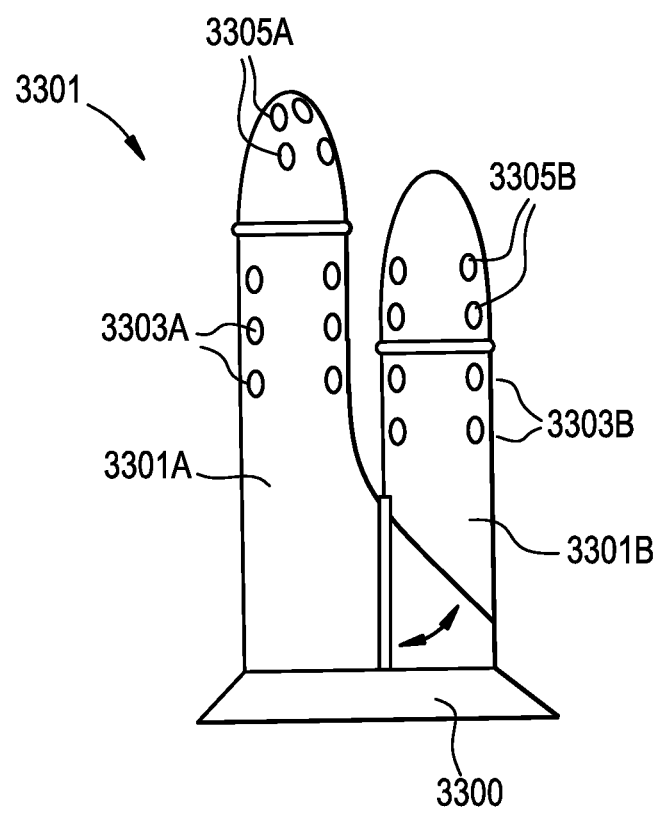
FIG. 33 is a sectional side view of a catheter.

FIG. 33 illustrates an exemplary catheter 3301 that can be used in the shunt systems described herein. The catheter 3301 includes one or more primary flow ports 3303 and one or more auxiliary flow ports 3305. The auxiliary flow port 3305 can be initially closed or blocked and selectively opened to provide an alternative path for fluid to flow through the catheter 3301, e.g., when the primary flow port 3303 becomes clogged. The catheter 3301 can include a first fluid lumen 3301A having a first primary flow port 3303A and a first auxiliary flow port 3305A and a second fluid lumen 3301B having a second primary flow port 3303B and a second auxiliary flow port 3305B. A diverter valve can be disposed between the first and second lumens 3301A, 3301B and a flusher 3300 of the type described herein to control which of the lumens is placed in fluid communication with the flusher.

In use, the valve can be initially configured such that the first lumen 3301A is in fluid communication with the flusher 3300, e.g., by swinging a partition defined by the valve to the right in the drawing. In this configuration, a low pressure flush operation can be used to clear obstructions from the first primary flow port 3303A and a high pressure flush operation can be used to open the first auxiliary flow port 3305A. If it is desired to open additional flow paths, the valve 3312 can be switched to place the second fluid lumen 3301B in fluid communication with the flusher 3300, e.g., by swinging a partition defined by the valve to the left in the drawing. In this switched configuration, the first fluid lumen 3301A is sealed off and fluid is shunted through the second fluid lumen 3301B. A low pressure flush operation can be used to clear obstructions from the second primary flow port 3303B and a high pressure flush operation can be used to open the second auxiliary flow port 3305B. The illustrated catheter 3301 can thus provide at least four different flow paths to provide multiple stages of restoring flow through the system.

In some embodiments, a flusher can include a compliance feature in communication with the flush path through the catheter. The compliance feature can be an expandable compartment, e.g., a balloon, a hydraulic accumulator, etc., that absorbs at least some of the volume and/or pressure of a flushing cough to prevent the flushing cough from opening an auxiliary flow port through the system while still allowing the flushing cough to clear primary flow ports of the system. A non-invasive control of the type described herein can be used to selectively fluidly-isolate the compliance feature from the flush path to allow a flushing operation to open an auxiliary flow port through the system. Exemplary non-invasive controls include remotely-actuated valves, e.g., magnetically-actuated valves.

Figure 34A:
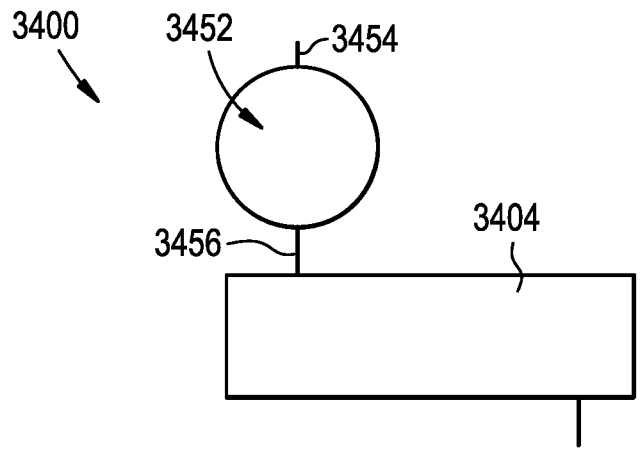
FIG. 34A is a schematic top view of a flusher.
Figure 34B:
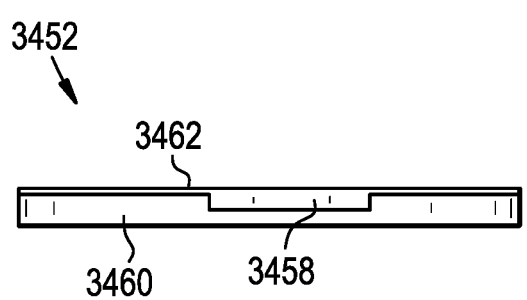
FIG. 34B is a sectional side view of a compliant member of the flusher of FIG. 34A, shown in a collapsed state.
Figure 34C:
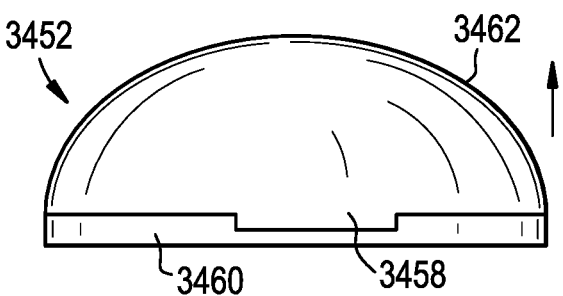
FIG. 34C is a sectional side view of the compliant member of FIG. 34B, shown in an expanded state.

FIGS. 34A-34C illustrate an exemplary flusher 3400 that includes a compliant feature 3452. The compliant feature 3452 can be formed integrally with the flusher 3400, e.g., in the same outer housing or unit as the flush dome 3404, or can be a separate component as shown. The compliant feature 3452 can include an upstream port 3454 in fluid communication with a ventricle or drain catheter, a downstream port 3456 in fluid communication with the flush dome 3404, and a fluid path 3458 connecting the upstream and downstream ports. The fluid path 3458 can be defined at least in part by a groove or recess formed in a base plate 3460 of the compliant feature 3452. The fluid path 3458 can be in fluid communication with the interior of an elastic membrane 3462. The elastic membrane 3462 can normally lay flat against the base plate 3460 as shown in FIG. 34B, but can expand away from the base plate when fluid is supplied thereto under pressure, as shown in FIG. 34C. The flusher 3400 is normally configured in a restricted operating mode. In the restricted operating mode, passive flow through system occurs through the fluid path 3458. In this operating mode, actuation of the flusher 3400 releases a cough of fluid that causes the elastic membrane 3462 to transition from the state shown in FIG. 34B to the state shown in FIG. 34C. In doing so, the elastic membrane 3462 absorbs some or all of the volume and/or pressure of the flush, preventing the flush from being applied to the ventricular catheter or limiting the degree to which the flush is applied to the ventricular catheter. When actuation of the flusher 3400 ceases, the fluid in the compliant feature 3452 can drain out through the passive flow path. The flusher 3400 can also be used in an unrestricted operating mode. In the unrestricted operating mode, a clinician or other user can hold the membrane 3462 in the state shown in FIG. 34B. With the membrane 3462 constrained from expanding, a flushing cough emitted in the unrestricted mode can be communicated to the ventricular catheter, e.g., to open an auxiliary flow port therethrough. The membrane 3462 can be held in the state shown in FIG. 34B by manual finger pressure through the patient's skin, or by pressure applied by a specialized tool positioned over the patient's skin against the upper surface of the compliant feature 3452.

Figure 35:
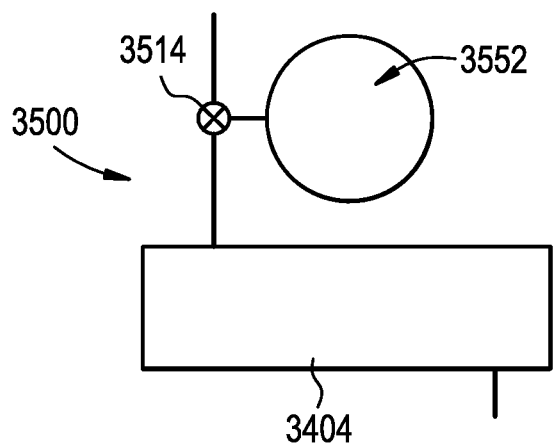
FIG. 35 is a schematic top view of a flusher.

FIG. 35 illustrates an exemplary flusher 3500 that includes a compliant feature 3552. The compliant feature 3552 can be formed integrally with the flusher 3500, e.g., in the same outer housing or unit as the flush dome 3504, or can be a separate component as shown. The compliant feature 3552 can include any of the features of the compliant feature 3452 described above. The flusher 3500 can include a control 3514. The control 3514 can be configured to selectively isolate the compliant feature 3552 from the flush path, and to selectively include the compliant feature in the flush path. Accordingly, the control 3514 can be switched between a restricted mode, in which the compliant feature 3552 is in communication with the flush path and absorbs some or all of a flush emitted from the flusher 3500, and an unrestricted mode, in which the compliant feature is isolated from the flush path such that a flush emitted from the flusher is applied to the catheter, e.g., to open an auxiliary flow path through the catheter. Exemplary controls can include valves, sliding controls, switches, and so forth. The control 3514 can be non-invasively actuated.

In some embodiments, a flusher can include a first flush dome (e.g., a patient flush dome) and a second flush dome (e.g., a clinician flush dome). The pressure and/or volume of the flush emitted from the first flush dome can be less than that of the second flush dome, such that actuating the first flush dome is insufficient to open an auxiliary flow port while actuation of the second flush dome is sufficient to open an auxiliary flow port. A non-invasive control of the type described herein can be used to selectively fluidly-isolate the second flush dome from the flush path to prevent opening of an auxiliary flow port and to fluidly-couple the second flush dome to the flush path to permit opening of an auxiliary flow port. Exemplary non-invasive controls include remotely-actuated valves, e.g., magnetically-actuated valves.

In some embodiments, a flusher can include a first flush valve (e.g., a patient flush valve) and a second flush valve (e.g., a clinician flush valve). The pressure and/or volume of the flush emitted from the first flush valve can be less than that of the second flush valve, such that actuating the first flush valve is insufficient to open an auxiliary flow port while actuation of the second flush valve is sufficient to open an auxiliary flow port. A non-invasive control of the type described herein can be used to selectively fluidly-isolate the second flush valve from the flush path to prevent opening of an auxiliary flow port and to fluidly-couple the second flush valve to the flush path to permit opening of an auxiliary flow port. Exemplary non-invasive controls include remotely-actuated valves, e.g., magnetically-actuated valves.

In some embodiments, a flusher can include a flush dome with an adjustable volume. The volume can be adjusted non-invasively between a first setting (e.g., a patient setting) in which the volume of a flush emitted from the flush dome is insufficient to open an auxiliary flow port and a second setting (e.g., a clinician setting) in which the volume of a flush emitted from the flush dome is sufficient to open an auxiliary flow port. The volume can be adjusted non-invasively using a non-invasive control of the type described herein. In one example, a movable shim can be positioned in the flush dome to reduce the volume. In another example, a threaded component can be threaded into the interior of the flush dome to decrease the volume of the flush dome. In another example, the flush dome can include a needle tap to allow additional fluid to be injected into the flush dome from a syringe.

Figure 36:
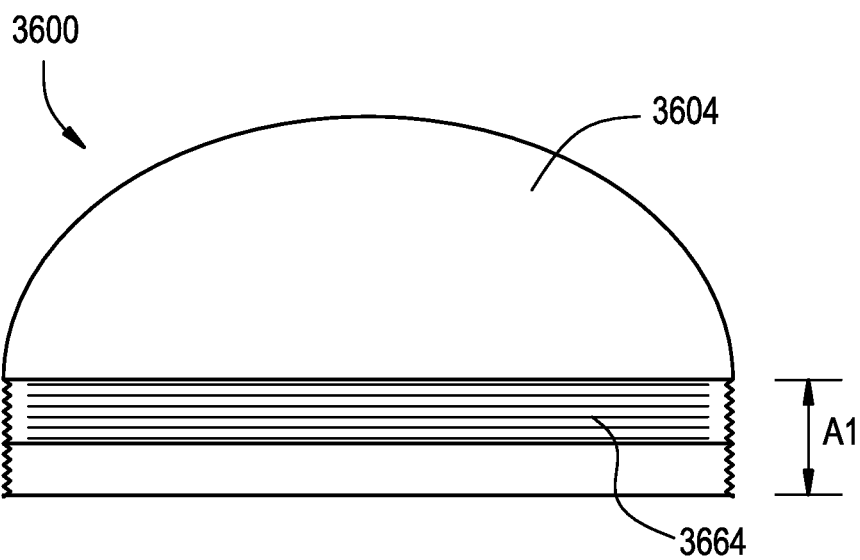
FIG. 36 is a sectional side view of an adjustable-volume flusher.

FIG. 36 illustrates an exemplary flusher 3600 with an adjustable flush volume. One or more surfaces of the flush cavity 3604 can be movable to alter the resting or effective volume of the flush cavity. For example, as shown, the lower surface of the flush cavity 3604 can be defined by a threaded plate 3664 threaded into a recess of the flush cavity. The plate 3664 can be rotated to translate the plate relative to the flush cavity 3604 along an axis A1. In particular, rotation of the plate 3664 in a first direction can move the plate upwards to reduce the volume of the flush cavity 3604, and rotation of the plate in a second, opposite direction can moved the plate downwards to increase the volume of the flush cavity. While a threaded interface is shown, it will be appreciated that various other mechanical couplings can be used to move the plate 3664. The plate 3664 can be actuated remotely, e.g., via an extracorporeal magnetic field. In a restricted mode, the plate 3664 can be raised to limit the volume and/or pressure of the flush. In an unrestricted mode, a control can be actuated to lower the plate 3664 and allow a higher volume and/or higher pressure flush to be generated.

Figure 37:
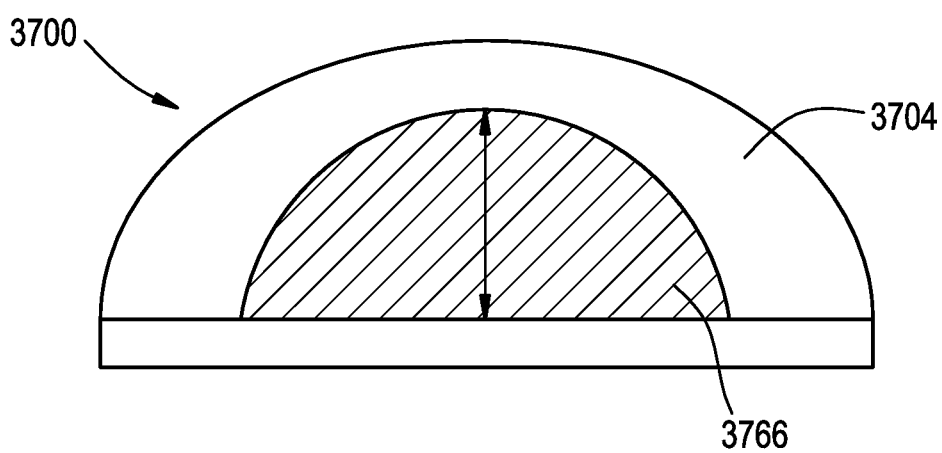
FIG. 37 is a sectional side view of another adjustable-volume flusher.

FIG. 37 illustrates an exemplary flusher 3700 with an adjustable flush volume. An inflatable member 3766 can be disposed within the flush cavity 3704 and can be inflatable or deflatable to adjust the resting or effective volume of the flush cavity. The inflatable member 3766 can be inflated via a non-invasive control. The inflatable member 3766 can include a needle tap to allow the inflatable member to be inflated or deflated with a syringe or other minimally-invasive injector. In a restricted mode, the inflatable member 3766 can be inflated to limit the volume and/or pressure of the flush. In an unrestricted mode, a control can be actuated to deflate the inflatable member 3766 and allow a higher volume and/or higher pressure flush to be generated.

Figure 38:
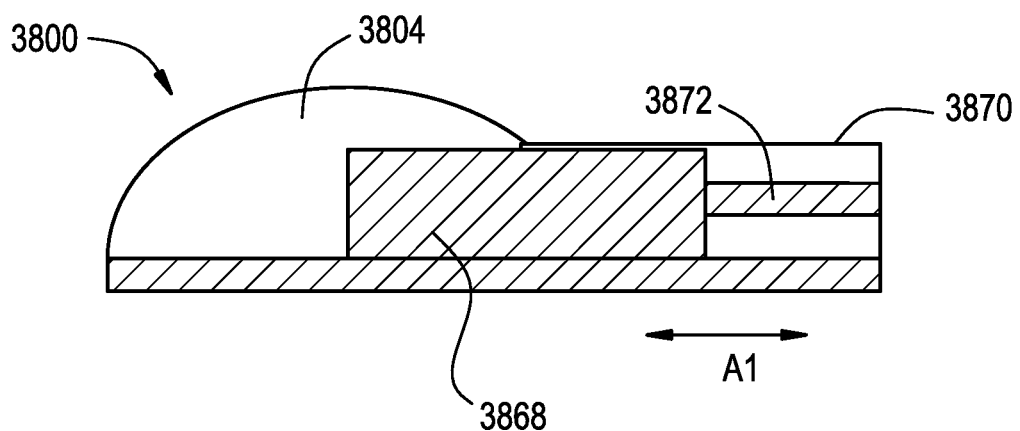
FIG. 38 is a sectional side view of another adjustable-volume flusher.

FIG. 38 illustrates an exemplary flusher 3800 with an adjustable flush volume. A movable member 3868 can be movably mounted in the flusher and can be selectively advanced into the flush cavity 3804 or retracted from the flush cavity to alter the resting or effective volume of the flush cavity. For example, as shown, a block 3868 can be mounted in a side pocket 3870 of the flusher 3800 and can slide along an axis A1 between a fully retracted and a fully advanced position. As the block 3868 is advanced into the flush cavity 3804, the block occupies at least a portion of the flush cavity volume, displacing fluid therefrom and thereby limiting the flush. The block 3868 can be controlled by a magnetically-rotatable threaded shaft, a solenoid actuator, a linear actuator, an injectable volume, or other control 3872. The block 3868 can be non-invasively controlled, e.g., by applying a magnetic field or other force from a location outside the patient in which the flusher 3800 is implanted. In a restricted mode, the movable member 3868 can be advanced into the flush cavity 3804 to limit the volume and/or pressure of the flush. In an unrestricted mode, a control can be actuated to withdraw the movable member 3868 from the flush cavity 3804 and allow a higher volume and/or higher pressure flush to be generated.

In some embodiments, a flusher can include a flush valve with an adjustable opening pressure. The pressure can be adjusted non-invasively between a first setting (e.g., a patient setting) in which the pressure of a flush emitted from the flusher is insufficient to open an auxiliary flow port and a second setting (e.g., a clinician setting) in which the pressure of a flush emitted from the flusher is sufficient to open an auxiliary flow port. The pressure can be adjusted non-invasively using a non-invasive control of the type described herein. In one example, a magnetically-rotatable disc can be rotated to adjust the pre-load on a spring holding the flush valve closed or the pressure on a deformable valve body pressed against a valve seat.

In some embodiments, a catheter can include multiple membranes covering respective auxiliary flow ports, the membranes varying in thickness, composition, dimensions, or other material properties to require progressively higher burst volumes and/or pressures to open their respective flow ports.

In some embodiments, a Rickham-style reservoir or skull anchor can include a tuned compliance feature. The compliance feature can be an expandable compartment, e.g., a balloon, a hydraulic accumulator, etc., that absorbs at least some of the volume and/or pressure of a flushing cough to prevent the flushing cough from opening an auxiliary flow port through the system while still allowing the flushing cough to clear primary flow ports of the system. A specialized extracorporeal tool can be positioned over the compliance feature to block expansion of the compliance feature, thereby limiting or preventing the flush from being absorbed and allowing the flush to instead open an auxiliary flow port. The extracorporeal tool can be a plate with a recess formed therein that forms a negative of the compliance feature when the compliance feature is in an unexpanded state.

A number of flushers are disclosed herein that include a pinch tube to occlude a drain side of the system during a flushing operation. In some embodiments, the pinch tube can be omitted and a non-invasively adjustable valve can be included in the flusher to selectively block the drain side of the system. In some embodiments, the non-invasively adjustable valve can be a shunt valve that in non-flushing conditions regulates flow through the system to regulate the pressure within the patient's ventricle.

It will be appreciated that, in any of the flusher embodiments above, the pinch tube or lumen can be disposed below the flush dome instead of on top of the flush dome as shown.

In any of the flushers disclosed herein, the flush dome can be sized to control the volume of fluid flushed through the shunt system during a flushing operation. In an exemplary embodiment, the flush dome has an interior volume of about 1 mL. In another exemplary embodiment, the flush dome has an interior volume of about 0.5 mL. The volume of the flush dome can be less than about 2 mL, less than about 1 mL, less than about 0.75 mL, and/or less than about 0.5 mL. The volume of the flush dome can be in the range of about 0.25 mL to about 0.75 mL. In any of the flushers disclosed herein, the flush dome can be configured to rebound or return to its un-collapsed configuration at a slow rate to prevent reflux action from sucking debris back into the shunt system. For example, the dome can be formed from a material having low resiliency properties such as polymeric compositions, silicone, nitrile, polyurethane, and so forth. Alternatively, or in addition, the dome can include ribs or other internal or external features for controlling the rebound rate of the dome. For example, the dome can include one or more ribs that extend from the base of the dome to the center peak of the dome. The ribs can extend along the interior surface of the dome. Alternatively, or in addition, the thickness of the dome can vary between the base and the peak. For example, the dome can be thicker at the base than at the peak. While flushers configured to flush only the upstream or ventricular side of the shunt system are disclosed herein, it will be appreciated that the disclosed flushers can be readily modified to flush only the downstream or drain side of the shunt system and/or to flush both sides of the shunt system. A number of flushers disclosed herein include a pinch tube, though it will be appreciated that any collapsible fluid pathway can be used instead or in addition.

Although specific embodiments have been described, it should be understood that numerous changes may be made within the spirit and scope of the concepts described. Accordingly, it is intended that the disclosure not be limited to the described embodiments.

The invention claimed is:

1. A shunt system, comprising:
   a catheter having a primary flow port and an auxiliary flow port; and a flusher configured to emit a flushing cough or pulse of fluid through the catheter;
wherein the shunt system is operable in a restricted mode in which:
(i) a flush generated by the flusher is insufficient to open the auxiliary flow port; or
(ii) the flusher is prevented from emitting the flush;
wherein the shunt system is operable in an unrestricted mode in which:
(i) a flush generated by the flusher is sufficient to open the auxiliary flow port; or
(ii) the flusher is not prevented from emitting the flush; and
wherein the flusher includes a control operable to switch the flusher between the restricted mode and the unrestricted mode; and
wherein the control reduces the pressure of the flush in the restricted mode and increases the pressure of the flush in the unrestricted mode.

2. The system of claim 1, wherein the control reduces the pressure of the flush by placing a flush dome of the flusher in communication with a first flush valve having a lower opening pressure and wherein the control increases the pressure of the flush by placing the flush dome in communication with a second flush valve having a higher opening pressure.

3. The system of claim 1, wherein the control isolates the auxiliary flow port from the flush in the restricted mode and does not isolate the auxiliary flow port from the flush in the unrestricted mode.

4. The system of claim 1, wherein the catheter includes a first fluid lumen in communication with the primary flow port and a second fluid lumen in communication with the auxiliary flow port.

5. The system of claim 4, wherein the control selects which of the first and second fluid lumens of the catheter is in fluid communication with a flush dome of the flusher.

6. The system of claim 1, wherein the control is operable to selectively direct the flush to one or more of an upstream port of the flusher and a downstream port of the flusher.

7. A shunt system, comprising:
a catheter having a primary flow port and an auxiliary flow port; and
a flusher configured to emit a flushing cough or pulse of fluid through the catheter;
wherein the shunt system is operable in a restricted mode in which:
(i) a flush generated by the flusher is insufficient to open the auxiliary flow port; or
(ii) the flusher is prevented from emitting the flush;
wherein the shunt system is operable in an unrestricted mode in which:
(i) a flush generated by the flusher is sufficient to open the auxiliary flow port; or
(ii) the flusher is not prevented from emitting the flush; and
wherein the flusher includes a control operable to switch the flusher between the restricted mode and the unrestricted mode; and
wherein the control reduces the volume of the flush in the restricted mode and increases the volume of the flush in the unrestricted mode.

8. The system of claim 7, wherein the control reduces the volume of the flush by limiting refill of a flush dome of the flusher.

9. The system of claim 7, wherein the control reduces the volume of the flush by decreasing the effective volume of a flush dome of the flusher.

10. The system of claim 9, wherein the control decreases the effective volume by at least one of: moving a divider within the flush dome, moving a volume-occupying object into the flush dome, and expanding a compartment within the flush dome.

11. A shunt system, comprising:
a catheter having a primary flow port and an auxiliary flow port; and
a flusher configured to selectively emit a first flush of fluid through the catheter or a second flush of fluid through the catheter;
wherein the first flush of fluid is not sufficient to open the auxiliary flow port and wherein the second flush of fluid is sufficient to open the auxiliary flow port; and
wherein the flusher includes first and second flush domes.

12. The system of claim 11, wherein the first and second flush domes are actuated simultaneously, the flusher emits the first flush by allowing fluid to escape from the first flush dome without contributing to the flush, and the flusher emits the second flush by including fluid in the first flush dome in the flush.

13. The system of claim 11, wherein the flusher emits the first flush when the first flush dome is collapsed and emits the second flush when the second flush dome is collapsed.

14. The system of claim 13, further comprising a control that isolates the second flush dome from an upstream port of the flusher to restrict opening of the auxiliary flow port.

15. The system of claim 13, wherein the second flush dome has a greater volume than the first flush dome.

* * * * *